(12) United States Patent
Coleman et al.

US007465746B2

(10) Patent No.: US 7,465,746 B2
(45) Date of Patent: Dec. 16, 2008

(54) FLUORINATED 2,4-DIARYL-2,5-DIHYDROPYRROLE INHIBITORS OF THE MITOTIC KINESIN KSP

(75) Inventors: Paul J. Coleman, Wallingford, PA (US); Christopher D. Cox, Harleysville, PA (US); Robert M. Garbaccio, Lansdale, PA (US); George D. Hartman, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 582 days.

(21) Appl. No.: 10/915,743

(22) Filed: Aug. 11, 2004

(65) Prior Publication Data

US 2005/0043357 A1     Feb. 24, 2005

Related U.S. Application Data

(60) Provisional application No. 60/563,580, filed on Apr. 19, 2004, provisional application No. 60/495,637, filed on Aug. 15, 2003.

(51) Int. Cl.
*A61K 31/4468* (2006.01)
(52) U.S. Cl. ..................................... 514/326; 546/187
(58) Field of Classification Search ................ 546/208, 546/187; 514/326
See application file for complete search history.

(56) References Cited

U.S. PATENT DOCUMENTS

| | | | | |
|---|---|---|---|---|
| 3,142,699 | A * | 7/1964 | Wagner et al. | 560/26 |
| 4,477,389 | A * | 10/1984 | Chen et al. | 560/347 |
| 6,057,342 | A | 5/2000 | Fevig et al. | |
| 6,440,686 | B1 | 8/2002 | Sakowicz | |
| 2005/0038074 | A1* | 2/2005 | Coleman et al. | 514/326 |
| 2005/0043357 | A1* | 2/2005 | Coleman et al. | 514/326 |
| 2005/0119484 | A1* | 6/2005 | Breslin et al. | 544/371 |
| 2005/0176776 | A1* | 8/2005 | Coleman et al. | 514/340 |
| 2005/0203110 | A1* | 9/2005 | Coleman et al. | 514/264.1 |
| 2005/0234080 | A1* | 10/2005 | Coleman et al. | 514/269 |
| 2006/0100191 | A1* | 5/2006 | Breslin et al. | 514/210.2 |
| 2006/0135594 | A1* | 6/2006 | Fraley et al. | 514/422 |
| 2006/0142278 | A1* | 6/2006 | Coleman et al. | 514/224.2 |
| 2006/0223844 | A1* | 10/2006 | Coleman | 514/301 |
| 2006/0287302 | A1* | 12/2006 | Coleman et al. | 514/227.5 |

FOREIGN PATENT DOCUMENTS

| | | |
|---|---|---|
| WO | WO 93/20099 | 10/1993 |
| WO | WO 98/06694 | 2/1998 |
| WO | WO 03/049527 | 6/2003 |
| WO | WO 03/105855 | 12/2003 |
| WO | WO 03/106417 | 12/2003 |
| WO | WO 2004/037171 | 5/2004 |

OTHER PUBLICATIONS

Commercial Boronic Acids (created by examiner).*
Commercial 1-1 (created by examiner).*
Commercial 4-piperidinones (created by examiner).*
Hutchins, R.O. et. al. J. Org. Chem. 1977, 42, 82-91.*
Dorwald F. A. Side Reactions in Organic Synthesis, 2005, Wiley: VCH, Weinheim Preface p. IX, Chapter 8, pp. 279-309.*
("Lithium Aluminum Hydride" Paquette, L. in Encyclopedia of Reagents for Organic Synthesis Online Posting Date: Oct. 15, 2004 John Wiley & Sons, Ltd. "http://www.mrw.interscience.wiley.com/eros/articles/rl036/frame.html".*
Bachmann et. al. Macromolecular Chemistry and Physics 2001, 202, 3410-3419.*
Mark E. Fraley, et. al. "Kinesin spindle protein (KSP) inhibitors. Part 2: The design, synthesis, and characterization of 2,4-diaryl-2,5-dihydropyrrole inhibitors of the mitotic kinesin KSP" Bioorganic & Medicinal Chemistry Letters 2006, 16, 1775-1779.*
Cox et. al. "Kinesin spindle protein (KSP) inhibitors. Part 1: The discovery of 3,5-diaryl-4,5-dihydropyrazoles as potent and selective inhibitors of the mitotic kinesin KSP" Bioorganic & Medicinal Chemistry Letters 2005, 15, 2041-2045.*
Henry R. Henze and Charles M. Blair "The Number of Structurally Isomeric Alcohols of the Methanol Series" Journal of the American Chemical Society 1931, 3042.*
Patani et. al. "Bioisosterism: A Rational Approach in Drug Design" Chemical Reviews 1996, 96, 3147-3176.*
C. Sonesson, et al., J. Org. Chem. 1996, vol. 61, p. 4756-4763.
N. Iwasawa, et al., J. Org. Chem. 1998, vol. 63, p. 3164-3165.
N. Iwasawa, et al., J. Org. Chem. 1997, vol. 62, p. 1918-1919.
R. Mison, et al., J. Chem. Research(S), 1989, 126-127.
O. Yebdri, et al., Bulletin De La Societe Chimique de France, 1983, p. 195-201.
A. Ranjon, Bulletin De La Societe Chimique de France, 1971, p. 2068-2072.
M. Bujard, et al., Tetrahedron Letters, vol. 40, 1999, p. 8785-8788.
M. Carpes, et al., Synlett, No. 7, 2000, p. 1037-1039.
A. Boukhari, et al., J. Cryst. Spect. Res., vol. 19, Iss. 3, 1989, p. 603-621.
C. Cox, et al., Bioorganic & Medicinal Chem Ltrs. vol. 15, pp. 2041-2045 (2005), "Kinesin spindle protein (KSP) inhibitors. Part 1: The discovery of 3,5-diaryl-4,5-dihydropyrazoles as potent and selective inhibitors of the mitotic kinesin KSP".
W. Tao, Cell Cycle, vol. 4(11), pp. 1495-1499 (2005), "The mitotic checkpoint in cancer therapy".

(Continued)

*Primary Examiner*—Rita Desai
*Assistant Examiner*—David K O'Dell
(74) *Attorney, Agent, or Firm*—Nicole M. Beeler; David A. Muthard

(57) ABSTRACT

The present invention relates to dihydropyrrole compounds that are useful for treating cellular proliferative diseases, for treating disorders associated with KSP kinesin activity, and for inhibiting KSP kinesin. The invention is also related to compositions which comprise these compounds, and methods of using them to treat cancer in mammals.

14 Claims, 2 Drawing Sheets

OTHER PUBLICATIONS

K. D. Chu, et al., Proc. Am. Soc. Clin. Oncol., abstract 525, p. 131 (2003), "A phase I study to determine the safety and pharmacokinetics of IV administered SB-715992, a novel kinesin spindle protein (KSP) inhibitor, in patients (pts) with solid tumors".

R. Sakowicz, et al., Cancer Research, vol. 64, pp. 3276-3280 (2004), "Antitumor activity of a kinesin inhibitor".

W. Tao, et al., Cancer Cell, vol. 8, pp. 49-59 (2005), "Induction of apoptosis by an inhibitor of the mitotic kinesin KSP requires both activation of the spindle assembly checkpoint and mitotic slippage".

M. Fraley, et al., Bioorganic & Medicinal Chem Ltrs., vol. 16, pp. 1775-1779 (2006), "Kinesin spindle protein (KSP) inhibitors. Part 2: The design, synthesis and characterization of 2,4-diaryl-2,5-dihydropyrrole inhibitors of the mitiotic kinesin KSP".

R. Garbaccio, et al., Bioorganic & Medicinal Chem Ltrs., vol. 16, pp. 1780-1783 (2006), "Kinesin spindle protein (KSP) inhibitors. Part 3: Synthesis and evaluation of phenolic 2,4-diaryl-2,5-dihydropyrroles with reduced hERG binding and employment of a phosphate prodrug strategy for aqueous solubility".

C. Cox, et al., Bioorganic & Medicinal Chem Ltrs., vol. 16, pp. 3175-3179 (2006), "Kinesin spindle protein (KSP) inhibitors. Part 4:1 Structure-based design of 5-alkylamino-3,5-diaryl-4,5-dihydropyrazoles as potent, water-soluble inhibitors of the mitotic kinesin KSP".

* cited by examiner

FLUORINATED 2,4-DIARYL-2,5-DIHYDROPYRROLE INHIBITORS OF THE MITOTIC KINESIN KSP

This application claims priority to U.S. Provisional Applications 60/563,580 filed Apr. 19, 2004 and 60/495,637 filed Aug. 15, 2003.

BACKGROUND OF THE INVENTION

This invention relates to 2,2-disubstituted 2,5-dihydropyrrole derivatives that are inhibitors of mitotic kinesins, in particular the mitotic kinesin KSP, and are useful in the treatment of cellular proliferative diseases, for example cancer, hyperplasias, restenosis, cardiac hypertrophy, immune disorders and inflammation.

Among the therapeutic agents used to treat cancer are the taxanes and vinca alkaloids. Taxanes and vinca alkaloids act on microtubules, which are present in a variety of cellular structures. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle . microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is KSP. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described [Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J Biol. Chem., 272:19418-24 (1997); Blangy, et al., Cell Motil Cytoskeleton, 40:174-82 (1998); Whitehead and Rattner, J. Cell Sci., 111:2551-61 (1998); Kaiser, et al., JBC 274:18925-31 (1999); GenBank accession numbers: X85137, NM004523 and U37426], and a fragment of the KSP gene (TRIP5) has been described [Lee, et al., Mol Endocrinol., 9:243-54 (1995); GenBank accession number L40372]. *Xenopus* KSP homologs (Eg5), as well as *Drosophila* K-LP61 F/KRP 130 have been reported.

Certain quinazolinones have recently been described as being inhibitors of KSP (PCT Publ. WO 01/30768, May 3, 2001).

Mitotic kinesins are attractive targets for the discovery and development of novel mitotic chemotherapeutics. Accordingly, it is an object of the present invention to provide compounds, methods and compositions useful in the inhibition of KSP, a mitotic kinesin.

SUMMARY OF THE INVENTION

The present invention relates to dihydropyrrole derivatives, that are useful for treating cellular proliferative diseases, for treating disorders associated with KSP kinesin activity, and for inhibiting KSP kinesin. The compounds of the invention may be illustrated by the Formula I:

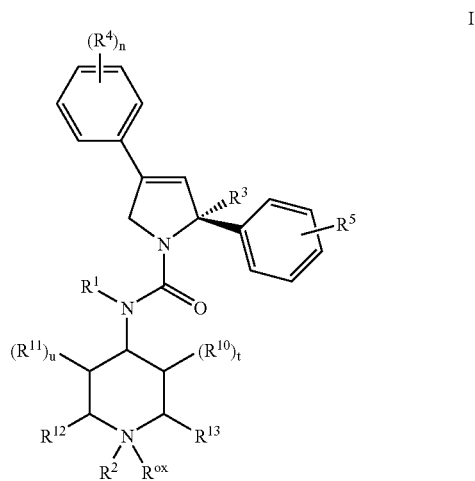

DETAILED DESCRIPTION OF THE INVENTION

Figure 1:
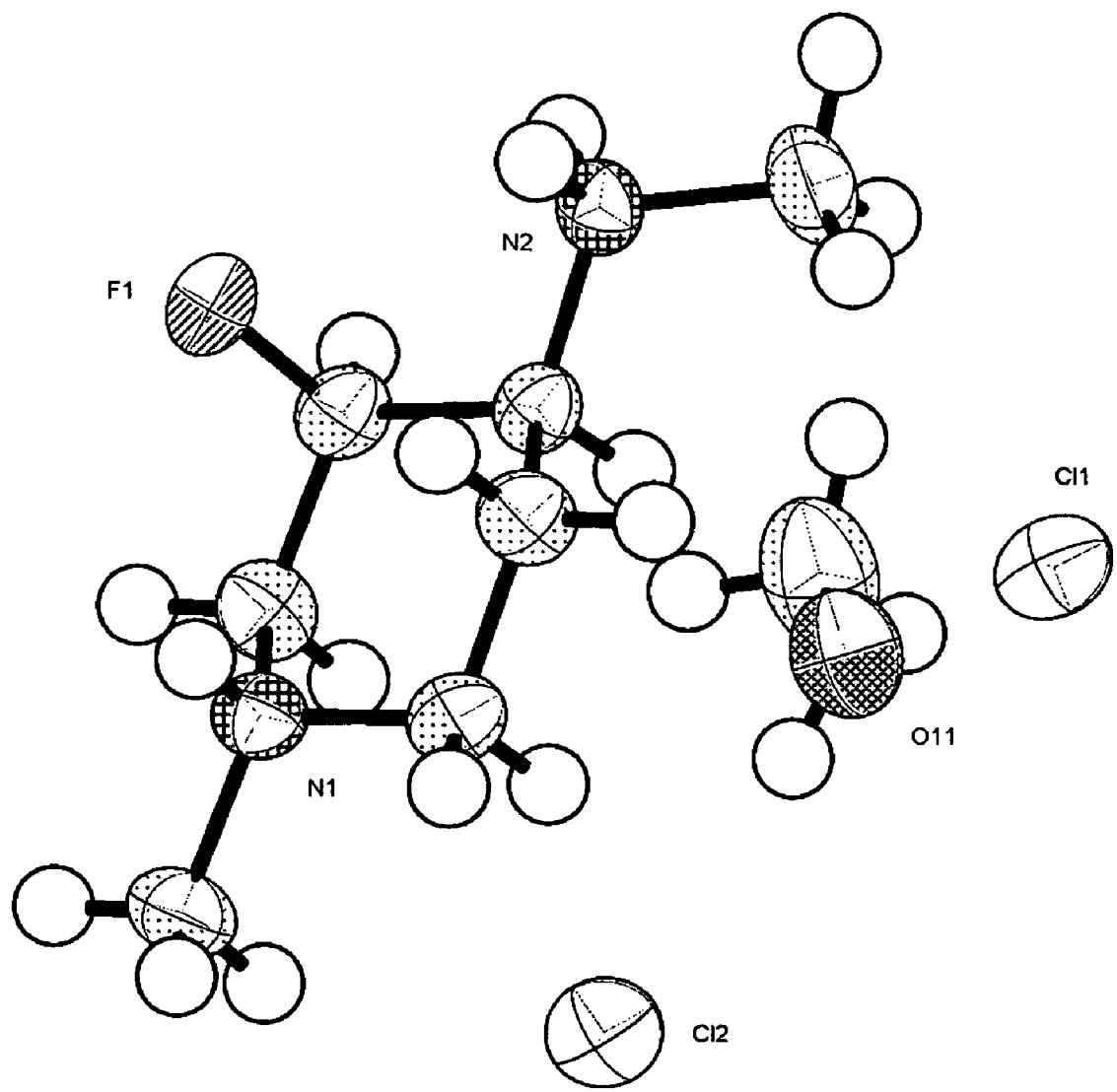
FIG. 1 An ORTEP drawing of Compound 2-5

The compounds of this invention are useful in the inhibition of mitotic kinesins and are illustrated by a compound of Formula I:

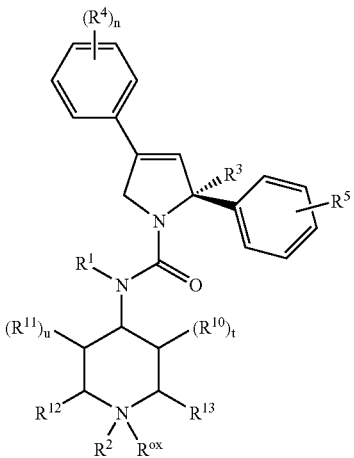

or a pharmaceutically acceptable salt or stereoisomer thereof, wherein:
a is 0 or 1;
b is 0 or 1;
m is 0, 1, or 2;
n is 0, 1, 2 or 3;
r is 0 or 1;
s is 0 or 1;
t is 0, 1 or 2;
u is 0 or 1;
$R^1$ and $R^2$ are independently selected from: H, ($C_1$-$C_6$)alkyl, aryl, heterocyclyl and ($C_3$-$C_6$)cycloalkyl, optionally substituted with one, two or three substituents selected from $R^7$;
$R^3$ is selected from:
  1) hydrogen;
  2) $C_1$-$C_{10}$ alkyl;
  3) $C_1$-$C_{10}$ alkyl-O—$R^d$,
  4) $C_2$-$C_{10}$ alkenyl-O—$R^d$,
  5) $C_2$-$C_{10}$ alkynyl-O—$R^d$,
  6) ($C_1$-$C_6$-alkylene)$_n$$C_3$-$C_8$ cycloalkyl-O—$R^d$,
  7) $C_1$-$C_{10}$ alkyl-(C=O)$_b$—NR$^c$R$^{c1}$,
  8) $C_2$-$C_{10}$ alkenyl-(C=O)$_b$NR$^c$R$^{c1}$,
  9) $C_2$-$C_{10}$ alkynyl-(C=O)$_b$NR$^c$R$^{c1}$,
  10) ($C_1$-$C_6$-alkylene)$_n$$C_3$-$C_8$ cycloalkyl-(C=O)$_b$NR$^c$R$^{c1}$,
  11) $C_1$-$C_{10}$ alkyl-S(O)$_m$—$R^d$,
  12) $C_2$-$C_{10}$ alkenyl-S(O)$_m$—$R^d$,
  13) $C_2$-$C_{10}$ alkynyl-S(O)$_m$—$R^d$,
  14) ($C_1$-$C_6$-alkylene)$_n$$C_3$-$C_8$ cycloalkyl-S(O)$_m$—$R^d$, said alkyl, alkenyl, alkynyl and cycloalkyl are optionally substituted with one or more substituents selected from $R^6$;
$R^4$ is independently selected from:
  1) (C=O)$_a$O$_b$$C_1$-$C_{10}$ alkyl,
  2) (C=O)$_a$O$_b$aryl,
  3) CO$_2$H,
  4) halo,
  5) CN,
  6) OH,
  7) O$_b$$C_1$-$C_6$ perfluoroalkyl,
  8) O$_a$(C=O)$_b$NR$^8$R$^9$,
  9) S(O)$_m$R$^a$,
  10) S(O)$_2$NR$^8$R$^9$, and
  11) —OPO(OH)$_2$;

said alkyl, aryl, alkenyl, alkynyl, heterocyclyl, and cycloalkyl optionally substituted with one, two or three substituents selected from $R^7$;
$R^5$ is selected from:
  1) hydrogen;
  2) (C=O)$_a$O$_b$$C_1$-$C_{10}$ alkyl,
  3) (C=O)$_a$O$_b$aryl,
  4) CO$_2$H,
  5) halo,
  6) CN,
  7) OH,
  8) O$_b$$C_1$-$C_6$ perfluoroalkyl,
  9) O$_a$(C=O)$_b$NR$^8$R$^9$,
  10) S(O)$_m$R$^a$,
  11) S(O)$_2$NR$^8$R$^9$, and
  12) —OPO(OH)$_2$;

said alkyl, aryl, alkenyl, alkynyl, heterocyclyl, and cycloalkyl optionally substituted with one, two or three substituents selected from $R^7$;
$R^6$ is independently selected from:
  1) (C=O)$_a$O$_b$$C_1$-$C_{10}$ alkyl,
  2) (C=O)$_a$O$_b$aryl,
  3) $C_2$-$C_{10}$ alkenyl,
  4) $C_2$-$C_{10}$ alkynyl,
  5) (C=O)$_a$O$_b$ heterocyclyl,
  6) CO$_2$H,
  7) halo,
  8) CN,
  9) OH,
  10) O$_b$$C_1$-$C_6$ perfluoroalkyl,
  11) O$_a$(C=O)$_b$NR$^8$R$^9$,
  12) S(O)$_m$R$^a$,
  13) S(O)$_2$NR$^8$R$^9$,
  14) oxo,
  15) CHO,
  16) (N=O)R$^8$R$^9$,
  17) (C=O)$_a$O$_b$$C_3$-$C_8$ cycloalkyl, and
  18) —OPO(OH)$_2$;

said alkyl, aryl, alkenyl, alkynyl, heterocyclyl, and cycloalkyl optionally substituted with one, two or three substituents selected from $R^7$;
$R^7$ is selected from:
  1) (C=O)$_r$O$_s$($C_1$-$C_{10}$)alkyl,
  2) O$_r$($C_1$-$C_3$)perfluoroalkyl,
  3) oxo,
  4) OH,
  5) halo,
  6) CN,
  7) ($C_2$-$C_{10}$)alkenyl,
  8) ($C_2$-$C_{10}$)alkynyl,
  9) (C=O)$_r$O$_s$($C_3$-$C_6$)cycloalkyl,
  10) (C=O)$_r$O$_s$($C_0$-$C_6$)alkylene-aryl,
  11) (C=O)$_r$O$_s$($C_0$-$C_6$)alkylene-heterocyclyl,
  12) (C=O)$_r$O$_s$($C_0$-$C_6$)alkylene-N(R$^b$)$_2$,
  13) C(O)R$^a$,
  14) ($C_0$-$C_6$)alkylene-CO$_2$R$^a$,
  15) C(O)H,
  16) ($C_0$-$C_6$)alkylene-CO$_2$H, and
  17) (C=O)$_r$N(R$^b$)$_2$,
  18) S(O)$_m$R$^a$,
  19) S(O)$_2$N(R$^b$)$_2$; and
  20) —OPO(OH)$_2$;

said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, $NO_2$ and $N(R^b)_2$;

$R^8$ and $R^9$ are independently selected from:
 1) H,
 2) $(C=O)O_bC_1-C_{10}$ alkyl,
 3) $(C=O)O_bC_3-C_8$ cycloalkyl,
 4) $(C=O)O_b$aryl,
 5) $(C=O)O_b$heterocyclyl,
 6) $C_1-C_{10}$ alkyl,
 7) aryl,
 8) $C_2-C_{10}$ alkenyl,
 9) $C_2-C_{10}$ alkynyl,
 10) heterocyclyl,
 11) $C_3-C_8$ cycloalkyl,
 12) $SO_2R^a$, and
 13) $(C=O)NR^b_2$, said alkyl, cycloalkyl, aryl, heterocylyl, alkenyl, and alkynyl is optionally substituted with one, two or three substituents selected from $R^7$, or $R^8$ and $R^9$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;

$R^{10}$ and $R^{11}$ are independently selected from: F and $—CH_2F$;
$R^{12}$ and $R^{13}$ are independently selected from: H and $—CH_2F$;
$R^{ox}$ is absent or is oxo;

$R^a$ is independently selected from: $(C_1-C_6)$alkyl, $(C_3-C_6)$cycloalkyl, aryl, or heterocyclyl, optionally substituted with one, two or three substituents selected from $R^7$;

$R^b$ is independently selected from: H, $(C_1-C_6)$alkyl, aryl, heterocyclyl, $(C_3-C_6)$cycloalkyl, $(C=O)OC_1-C_6$ alkyl, $(C=O)C_1-C_6$ alkyl, $(C=O)$aryl, $(C=O)$heterocyclyl, $(C=O)NR^eR^{e_1}$ or $S(O)_2R^a$, optionally substituted with one, two or three substituents selected from $R^7$;

$R^c$ and $R^{c_1}$ are independently selected from: H, $(C_1-C_6)$alkyl, aryl, $NH_2$, OH, $OR^a$, $—(C_1-C_6)$alkyl-OH, $—(C_1-C_6)$alkyl-O—$(C_1-C_6)$alkyl, $(C=O)OC_1-C_6$ alkyl, $(C=O)C_1-C_6$ alkyl, $(C=O)$aryl, $(C=O)$heterocyclyl, $(C=O)NR^eR^{e_1}$, $S(O)^2R^a$ and $—(C_1-C_6)$alkyl-$N(R^b)_2$, wherein the alkyl is optionally substituted with one, two or three substituents selected from $R^7$; or $R^c$ and $R^{c_1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;

$R^d$ is selected from: H, $(C_1-C_6)$alkyl, $—(C_2-C_6)$alkyl-OH, $—(C_1-C_6)$alkyl-O—$(C_1-C_6)$alkyl and $—(C_1-C_6)$alkyl-N$(R^b)_2$, wherein the alkyl is optionally substituted with one, two or three substituents selected from $R^7$;;

$R^e$ and $R^{e_1}$ are independently selected from: H, $(C_1-C_6)$alkyl, aryl, heterocyclyl and $(C_3-C_6)$cycloalkyl, optionally substituted with one, two or three substituents selected from $R^7$; or $R^e$ and $R^{e_1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$.

The compounds of this invention are useful in the inhibition of mitotic kinesins and are illustrated by a compound of Formula II:

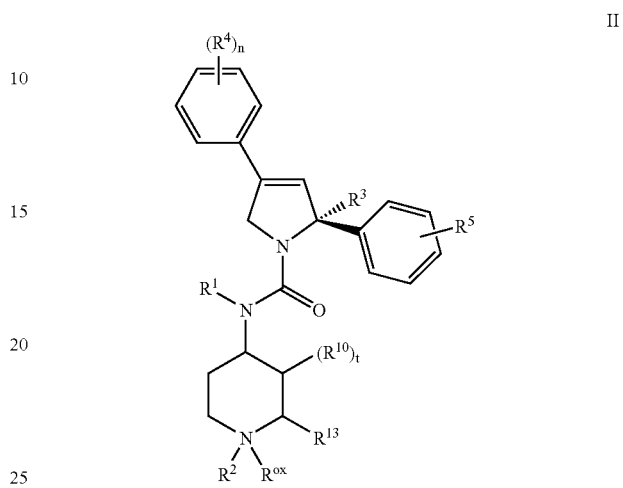

II or a pharmaceutically acceptable salt or stereoisomer thereof, wherein:
a is 0 or 1;
b is 0 or 1;
m is 0, 1, or 2;
n is 0, 1, 2 or 3;
r is 0 or 1;
s is 0 or 1;
t is 0 or 1;

$R^1$ and $R^2$ are independently selected from: H, $(C_1-C_6)$alkyl, aryl, heterocyclyl and $(C_3-C_6)$cycloalkyl, optionally substituted with one, two or three substituents selected from $R^7$;

$R^3$ is selected from:
 1) hydrogen;
 2) $C_1-C_{10}$ alkyl;
 3) $C_1-C_{10}$ alkyl-O—$R^d$,
 4) $C_2-C_{10}$ alkenyl-O—$R^d$,
 5) $C_2-C_{10}$ alkynyl-O—$R^d$,
 6) $(C_1-C_6$-alkylene$)_nC_3-C_8$ cycloalkyl-O—$R^d$,
 7) $C_1-C_{10}$ alkyl-$(C=O)_b$—$NR^cR^{c_1}$,
 8) $C_2-C_{10}$ alkenyl-$(C=O)_b$$NR^cR^{c_1}$,
 9) $C_2-C_{10}$ alkynyl-$(C=O)_b$$NR^cR^{c_1}$,
 10) $(C_1-C_6$-alkylene$)_nC_3-C_8$ cycloalkyl-$(C=O)_bNR^cR^{c_1}$,
 11) $C_1-C_{10}$ alkyl-$S(O)_m$—$R^d$,
 12) $C_2-C_{10}$ alkenyl-$S(O)_m$—$R^d$,
 13) $C_2-C_{10}$ alkynyl-$S(O)_m$—$R^d$,
 14) $(C_1-C_6$-alkylene$)_nC_3-C_8$ cycloalkyl-$S(O)_m$—$R^d$, said alkyl, alkenyl, alkynyl and cycloalkyl are optionally substituted with one or more substituents selected from $R^6$;

$R^4$ is independently selected from:
 1) $(C=O)_aO_bC_1-C_{10}$ alkyl,
 2) $(C=O)_aO_b$aryl,
 3) $CO_2H$,
 4) halo,
 5) CN,
 6) OH,
 7) $O_bC_1-C_6$ perfluoroalkyl,
 8) $O_a(C=O)_bNR^8R^9$, 9) $S(O)_m R^a$,
10) $S(O)_2 NR^8 R^9$, said alkyl, aryl, alkenyl, alkynyl, heterocyclyl, and cycloalkyl optionally substituted with one, two or three substituents selected from $R^7$;

$R^5$ is selected from:
1) hydrogen;
2) $(C=O)_a O_b C_1$-$C_{10}$ alkyl,
3) $(C=O)_a O_b$aryl,
4) $CO_2 H$,
5) halo,
6) CN,
7) OH,
8) $O_b C_1$-$C_6$ perfluoroalkyl,
9) $O_a(C=O)_b NR^8 R^9$,
10) $S(O)_m R^a$,
11) $S(O)_2 NR^8 R^9$, and
12) $-OPO(OH)_2$;

said alkyl, aryl, alkenyl, alkynyl, heterocyclyl, and cycloalkyl optionally substituted with one, two or three substituents selected from $R^7$;

$R^6$ is independently selected from:
1) $(C=O)_a O_b C_1$-$C_{10}$ alkyl,
2) $(C=O)_a O_b$aryl,
3) $C_2$-$C_{10}$ alkenyl,
4) $C_2$-$C_{10}$ alkynyl,
5) $(C=O)_a O_b$ heterocyclyl,
6) $CO_2 H$,
7) halo,
8) CN,
9) OH,
10) $O_b C_1$-$C_6$ perfluoroalkyl,
11) $O_a(C=O)_b NR^8 R^9$,
12) $S(O)_m R^a$,
13) $S(O)_2 NR^8 R^9$,
14) oxo,
15) CHO,
16) $(N=O)R^8 R^9$,
17) $(C=O)_a O_b C_3$-$C_8$ cycloalkyl, and
18) $-OPO(OH)_2$;

said alkyl, aryl, alkenyl, alkynyl, heterocyclyl, and cycloalkyl optionally substituted with one, two or three substituents selected from $R^7$;

$R^7$ is selected from:
1) $(C=O)_r O_s(C_1$-$C_{10})$alkyl,
2) $O_r(C_1$-$C_3)$perfluoroalkyl,
3) oxo,
4) OH,
5) halo,
6) CN,
7) $(C_2$-$C_{10})$alkenyl,
8) $(C_2$-$C_{10})$alkynyl,
9) $(C=O)_r O_s(C_3$-$C_6)$cycloalkyl,
10) $(C=O)_r O_s(C_0$-$C_6)$alkylene-aryl,
11) $(C=O)_r O_s(C_0$-$C_6)$alkylene-heterocyclyl,
12) $(C=O)_r O_s(C_0$-$C_6)$alkylene-N$(R^b)_2$,
13) $C(O)R^a$,
14) $(C_0$-$C_6)$alkylene-$CO_2 R^a$,
15) $C(O)H$,
16) $(C_0$-$C_6)$alkylene-$CO_2 H$,
17) $C(O)N(R^b)_2$,
18) $S(O)_m R^a$,
19) $S(O)_2 N(R^b)_2$; and
20) $-OPO(OH)_2$;

said alkyl, alkenyl, alkynyl, cycloalkyl, aryl, alkylene and heterocyclyl is optionally substituted with up to three substituents selected from $R^b$, OH, $(C_1$-$C_6)$alkoxy, halogen, $CO_2 H$, CN, $O(C=O)C_1$-$C_6$ alkyl, oxo, $NO_2$ and $N(R^b)_2$;

$R^8$ and $R^9$ are independently selected from:
1) H,
2) $(C=O)O_b C_1$-$C_{10}$ alkyl,
3) $(C=O)O_b C_3$-$C_8$ cycloalkyl,
4) $(C=O)O_b$aryl,
5) $(C=O)O_b$heterocyclyl,
6) $C_1$-$C_{10}$ alkyl,
7) aryl,
8) $C_2$-$C_{10}$ alkenyl,
9) $C_2$-$C_{10}$ alkynyl,
10) heterocyclyl,
11) $C_3$-$C_8$ cycloalkyl,
12) $SO_2 R^a$, and
13) $(C=O)NR^b{}_2$, said alkyl, cycloalkyl, aryl, heterocylyl, alkenyl, and alkynyl is optionally substituted with one, two or three substituents selected from $R^7$, or $R^8$ and $R^9$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;

$R^{10}$ is selected from: F and $-CH_2 F$;
$R^{13}$ is selected from: H and $-CH_2 F$, provided that if t is 1, $R^{13}$ is H;
$R^{ox}$ is absent or is oxo;
$R^a$ is independently selected from: $(C_1$-$C_6)$alkyl, $(C_3$-$C_6)$cycloalkyl, aryl, or heterocyclyl, optionally substituted with one, two or three substituents selected from $R^7$;
$R^b$ is independently selected from: H, $(C_1$-$C_6)$alkyl, aryl, heterocyclyl, $(C_3$-$C_6)$cycloalkyl, $(C=O)OC_1$-$C_6$ alkyl, $(C=O)C_1$-$C_6$ alkyl, $(C=O)$aryl, $(C=O)$heterocyclyl, $(C=O)NR^c R^{c'}$ or $S(O)_2 R^a$, optionally substituted with one, two or three substituents selected from $R^7$;
$R^c$ and $R^{c'}$ are independently selected from: H, $(C_1$-$C_6)$alkyl, aryl, $NH_2$, OH, $OR^a$, $-(C_1$-$C_6)$alkyl-OH, $-(C_1$-$C_6)$alkyl-O$-(C_1$-$C_6)$alkyl, $(C=O)OC_1$-$C_6$ alkyl, $(C=O)C_1$-$C_6$ alkyl, $(C=O)$aryl, $(C=O)$heterocyclyl, $(C=O)NR^e R^{e'}$, $S(O)_2 R^a$ and $-(C_1$-$C_6)$alkyl-N$(R^b)_2$, wherein the alkyl is optionally substituted with one, two or three substituents selected from $R^7$; or
$R^c$ and $R^{c'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;
$R^d$ is selected from: H, $(C_1$-$C_6)$alkyl, $-(C_2$-$C_6)$alkyl-OH, $-(C_1$-$C_6)$alkyl-O$-(C_1$-$C_6)$alkyl and $-(C_1$-$C_6)$alkyl-N$(R^b)_2$, wherein the alkyl is optionally substituted with one, two or three substituents selected from $R^7$;;
$R^e$ and $R^{e'}$ are independently selected from: H, $(C_1$-$C_6)$alkyl, aryl, heterocyclyl and $(C_3$-$C_6)$cycloalkyl, optionally substituted with one, two or three substituents selected from $R^7$; or
$R^e$ and $R^{e'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$.

In an embodiment of the invention the compounds are illustrated by a compound of Formula m:

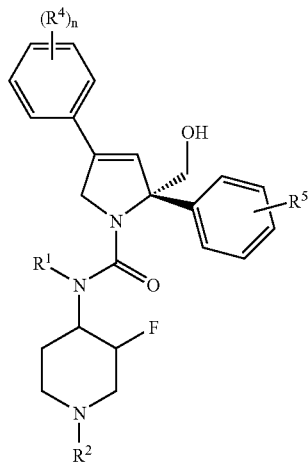

III or a pharmaceutically acceptable salt or stereoisomer thereof, wherein:

a is 0 or 1;
b is 0 or 1;
m is 0,1, or 2;
n is 0, 1 or 2;
r is 0 or 1;
s is 0 or 1;
$R^1$ and $R^2$ are independently selected from: H, $(C_1-C_6)$alkyl, aryl and $(C_3-C_6)$cycloalkyl, optionally substituted with one, two or three substituents selected from $R^7$;
$R^4$ is independently selected from:
1) halo,
2) OH,
3) $O_bC_1-C_6$ perfluoroalkyl,
$R^5$ is selected from:
1) hydrogen,
2) halo,
3) OH,
4) $O_bC_1-C_6$ perfluoroalkyl,
$R^7$ is selected from:
1) $(C=O)_rO_s(C_1-C_{10})$alkyl,
2) $O_r(C_1-C_3)$perfluoroalkyl,
3) oxo,
4) OH,
5) halo,
6) CN,
7) $(C_2-C_{10})$alkenyl,
8) $(C_2-C_{10})$alkynyl,
9) $(C=O)_rO_s(C_3-C_6)$cycloalkyl,
10) $(C=O)_rO_s(C_0-C_6)$alkylene-aryl,
11) $(C=O)_rO_s(C_0-C_6)$alkylene-heterocyclyl,
12) $(C=O)_rO_s(C_0-C_6)$alkylene-$N(R^b)_2$,
13) $C(O)R^a$,
14) $(C_0-C_6)$alkylene-$CO_2R^a$,
15) C(O)H,
16) $(C_0-C_6)$alkylene-$CO_2H$, and
17) $C(O)N(R^b)_2$,
18) $S(O)_mR^a$, and
19) $S(O)_2N(R^b)_2$;
said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, $NO_2$ and $N(R^b)_2$;
$R^8$ and $R^9$ are independently selected from:
1) H,
2) $(C=O)O_bC_1-C_{10}$ alkyl,
3) $(C=O)O_bC_3-C_8$ cycloalkyl,
4) $(C=O)O_b$aryl,
5) $(C=O)O_b$heterocyclyl,
6) $C_1-C_{10}$ alkyl,
7) aryl,
8) $C_2-C_{10}$ alkenyl,
9) $C_2-C_{10}$ alkynyl,
10) heterocyclyl,
11) $C_3-C_8$ cycloalkyl,
12) $SO_2R^a$, and
13) $(C=O)NR^b_2$, said alkyl, cycloalkyl, aryl, heterocylyl, alkenyl, and alkynyl is optionally substituted with one, two or three substituents selected from $R^7$, or $R^8$ and $R^9$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;

$R^a$ is independently selected from: $(C_1-C_6)$alkyl, $(C_3-C_6)$cycloalkyl, aryl, or heterocyclyl, optionally substituted with one, two or three substituents selected from $R^7$;

$R^b$ is independently selected from: H, $(C_1-C_6)$alkyl, aryl, heterocyclyl, $(C_3-C_6)$cycloalkyl, $(C=O)OC_1-C_6$ alkyl, $(C=O)C_1-C_6$ alkyl, $(C=O)$aryl, $(C=O)$heterocyclyl, $(C=O)NR^eR^{e1}$ or $S(O)_2R^a$, optionally substituted with one, two or three substituents selected from $R^7$;

$R^c$ and $R^{c1}$ are independently selected from: H, $(C_1-C_6)$alkyl, aryl, $NH_2$, OH, $OR^a$, —$(C_1-C_6)$alkyl-OH, —$(C_1-C_6)$alkyl-O—$(C_1-C_6)$alkyl, $(C=O)OC_1-C_6$ alkyl, $(C=O)C_1-C_6$ alkyl, $(C=O)$aryl, $(C=O)$heterocyclyl, $(C=O)NR^eR^{e1}$, $S(O)^yR^a$ and —$(C_1-C_6)$alkyl-$N(R^b)_2$, wherein the alkyl is optionally substituted with one, two or three substituents selected from $R^7$; or $R^c$ and $R^{c1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;

$R^e$ and $R^{e1}$ are independently selected from: H, $(C_1-C_6)$alkyl, aryl, heterocyclyl and $(C_3-C_6)$cycloalkyl, optionally substituted with one, two or three substituents selected from $R^7$; or $R^e$ and $R^{e1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$.

Another embodiment of the present invention is illustrated by a compound of Formula

IV

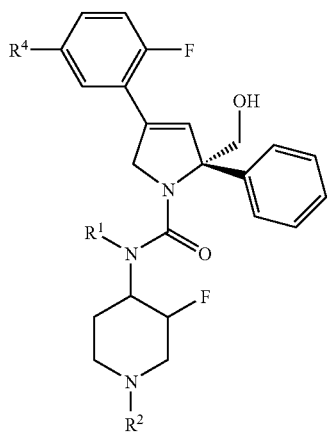

or a pharmaceutically acceptable salt or stereoisomer thereof, wherein:
a is 0 or 1;
b is 0 or 1;
m is 0, 1, or 2;
r is 0 or 1;
s is 0 or 1;
$R^1$ and $R^2$ are independently selected from: H and $(C_1-C_6)$ alkyl, optionally substituted with one, two or three substituents selected from $R^7$;
$R^4$ is independently selected from:
  1) halo,
  2) OH,
  3) $O_bC_1-C_6$ perfluoroalkyl,
$R^7$ is selected from:
  1) $(C=O)_rO_s(C_1-C_{10})$alkyl,
  2) $O_r(C_1-C_3)$perfluoroalkyl,
  3) oxo,
  4) OH,
  5) halo,
  6) CN,
  7) $(C_2-C_{10})$alkenyl,
  8) $(C_2-C_{10})$alkynyl,
  9) $(C=O)_rO_s(C_3-C_6)$cycloalkyl,
  10) $(C=O)_rO_s(C_0-C_6)$alkylene-aryl,
  11) $(C=O)_rO_s(C_0-C_6)$alkylene-heterocyclyl,
  12) $(C=O)_rO_s(C_0-C_6)$alkylene-N$(R^b)_2$,
  13) $C(O)R^a$,
  14) $(C_0-C_6)$alkylene-$CO_2R^a$,
  15) C(O)H,
  16) $(C_0-C_6)$alkylene-$CO_2H$, and
  17) $C(O)N(R^b)_2$,
  18) $S(O)_mR^a$, and
  19) $S(O)_2N(R^b)_2$;
said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, $NO_2$ and $N(R^b)_2$;
$R^8$ and $R^9$ are independently selected from:
  1) H,
  2) $(C=O)O_bC_1-C_{10}$ alkyl,
  3) $(C=O)O_bC_3-C_8$ cycloalkyl,
  4) $(C=O)O_b$aryl,
  5) $(C=O)O_b$heterocyclyl,
  6) $C_1-C_{10}$ alkyl,
  7) aryl,
  8) $C_2-C_{10}$ alkenyl,
  9) $C_2-C_{10}$ alkynyl,
  10) heterocyclyl,
  11) $C_3-C_8$ cycloalkyl,
  12) $SO_2R^a$, and
  13) $(C=O)NR^b_2$,
said alkyl, cycloalkyl, aryl, heterocylyl, alkenyl, and alkynyl is optionally substituted with one, two or three substituents selected from $R^7$, or
$R^8$ and $R^9$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;
$R^a$ is independently selected from: $(C_1-C_6)$alkyl, $(C_3-C_6)$cycloalkyl, aryl, or heterocyclyl, optionally substituted with one, two or three substituents selected from $R^7$;
$R^b$ is independently selected from: H, $(C_1-C_6)$alkyl, aryl, heterocyclyl, $(C_3-C_6)$cycloalkyl, $(C=O)OC_1-C_6$ alkyl, $(C=O)C_1-C_6$ alkyl, $(C=O)$aryl, $(C=O)$heterocyclyl, $(C=O)NR^eR^{e'}$ or $S(O)_2R^a$, optionally substituted with one, two or three substituents selected from $R^7$;
$R^c$ and $R^{c'}$ are independently selected from: H, $(C_1-C_6)$alkyl, aryl, $NH_2$, OH, $OR^a$, $-(C_1-C_6)$alkyl-OH, $-(C_1-C_6)$alkyl-O-$(C_1-C_6)$alkyl, $(C=O)OC_1-C_6$ alkyl, $(C=O)C_1-C_6$ alkyl, $(C=O)$aryl, $(C=O)$heterocyclyl, $(C=O)NR^eR^{e'}$, $S(O)^yR^a$ and $-(C_1-C_6)$alkyl-N$(R^b)_2$, wherein the alkyl is optionally substituted with one, two or three substituents selected from $R^7$; or
$R^c$ and $R^{c'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;
$R^e$ and $R^{e'}$ are independently selected from: H, $(C_1-C_6)$alkyl, aryl, heterocyclyl and $(C_3-C_6)$cycloalkyl, optionally substituted with one, two or three substituents selected from $R^7$; or
$R^e$ and $R^{e'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$.

A further embodiment of the present invention is illustrated by a compound of Formula V:

V

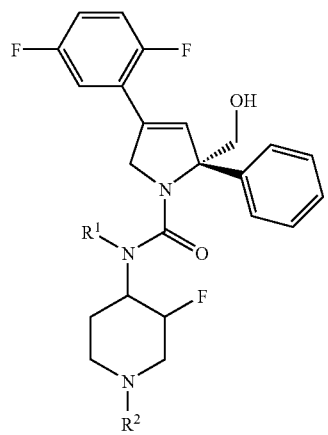

or a pharmaceutically acceptable salt or stereoisomer thereof, wherein:

R¹ and R² are independently selected from: H and (C₁-C₆) alkyl.

A further embodiment of the present invention is illustrated by a compound of Formula VI:

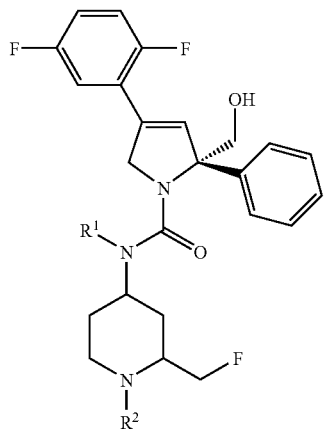

VI or a pharmaceutically acceptable salt or stereoisomer thereof, wherein:

R¹ and R² are independently selected from: H and (C₁-C₆) alkyl.

Specific examples of the compounds of the instant invention include:

(2S)-4-(2,5-Difluorophenyl)-N-[(3S,4R)-3-fluoro-1-methylpiperidin-4-yl]-2-(hydroxymethyl)-N-methyl-2-phenyl-2,5-dihydro-1H-pyrrole-1-carboxamide (2S)-4-(2,5-Difluorophenyl)-N-[(3R,4S)-3-fluoro-1-methylpiperidin-4-yl]-2-(hydroxymethyl)-N-methyl-2-phenyl-2,5-dihydro-1H-pyrrole-1-carboxamide (2S)-4-(2,5-Difluorophenyl)-N-[(3R,4R)-3-fluoro-1-methylpiperidin-4-yl]-2-(hydroxymethyl)-N-methyl-2-phenyl-2,5dihydro-1H-pyrrole-1-carboxamide (2S)-4-(2,5-Difluorophenyl)-N-[(3S,4S)-3-fluoro-1-methylpiperidin-4-yl]-2-(hydroxymethyl)-N-methyl-2-phenyl-2,5-dihydro-1H-pyrrole-1-carboxamide (2S)-4-(2,5-Difluorophenyl)-N-[(3S,4R)-3-fluoro-1-methylpiperidin-4-yl]-N-methyl-2-phenyl-2,5-dihydro-1H-pyrrole-1-carboxamide (2S)-4-(2,5-Difluorophenyl)-N-[(3R,4S)-3-fluoro-1-methylpiperidin-4-yl]-N-methyl-2-phenyl-2,5-dihydro-1H-pyrrole-1-carboxamide (2S)-4-(2,5-Difluorophenyl)-N-[(3R,4R)-3-fluoro-1-methylpiperidin-4-yl]-N-methyl-2-phenyl-2,5-dihydro-1H-pyrrole-1-carboxamide (2S)-4-(2,5-Difluorophenyl)-N-[(2R,4R)-2-(fluoromethyl)-1-methylpiperidin-4-yl]-2-(hydroxymethyl)-N-methyl-2-phenyl-2,5-dihydro-1H-pyrrole-1-carboxamide (2S)-4-(2,5-Difluorophenyl)-N-[(2S,4S)-2-(fluoromethyl)-1-methylpiperidin-4-yl]-2-(hydroxymethyl)-N-methyl-2-phenyl-2,5-dihydro-1H-pyrrole-1-carboxamide (2S)-4-(2,5-Difluorophenyl)-N-[(3S,4R)-3-fluoro-1-methyl-1-oxidopiperidin-4-yl]-2-(hydroxymethyl)-N-methyl-2-phenyl-2,5-dihydro-1H-pyrrole-1-carboxamide (2S)-4-(2,5-Difluorophenyl)-N-[(3S,4R)-3-fluoropiperidin-4-yl]-2-(hydroxymethyl)-N-methyl-2-phenyl-2,5-dihydro-1H-pyrrole-1-carboxamide (2S)-4-(2,5-Difluorophenyl)-N-[(3S,4R)-3-fluoro-1-isopropylpiperidin-4-yl]-2-(hydroxymethyl)-N-methyl-2-phenyl-2,5-dihydro-1H-pyrrole-1-carboxamide (2S)-4-(2,5-Difluorophenyl)-N-[(3S,4S)-3-fluoropiperidin-4-yl]-2-(hydroxymethyl)-N-methyl-2-phenyl-2,5-dihydro-1H-pyrrole-1-carboxamide or a pharmaceutically acceptable salt or stereoisomer thereof.

Particular examples of the compounds of the instant invention are:

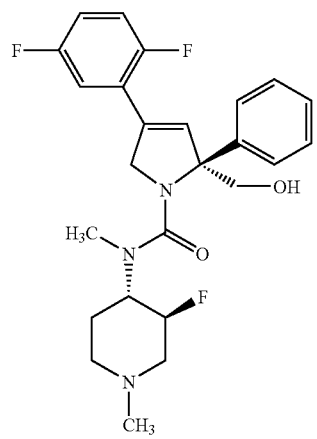

(2S)-4-(2,5-Difluorophenyl)-N-[(3S,4S)-3-fluoro-1-methylpiperidin-4-yl]-2-(hydroxymethyl)-N-methyl-2-phenyl-2,5-dihydro-1H-pyrrole-1-carboxamide

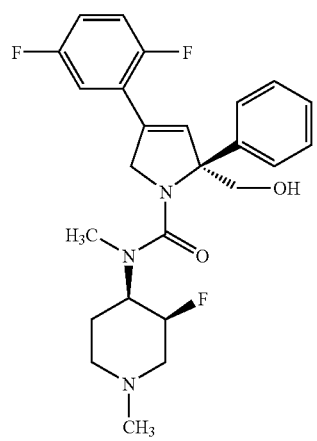

(2S)-4-(2,5-Difluorophenyl)-N-[(3S,4R)-3-fluoro-1-methylpiperidin-4-yl]-2-(hydroxymethyl)-N-methyl-2-phenyl-2,5-dihydro-1H-pyrrole-1-carboxamide

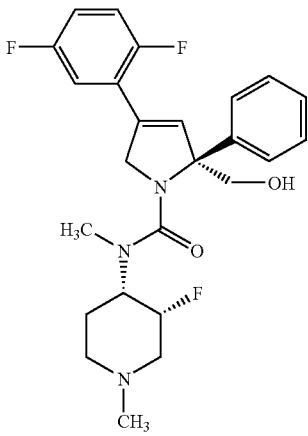

(2S)-4-(2,5-Difluorophenyl)-N-[(3R,4S)-3-fluoro-1-methylpiperidin-4-yl]-2-(hydroxymethyl)-N-methyl-2-phenyl-2,5-dihydro-1H-pyrrole-1-carboxamide

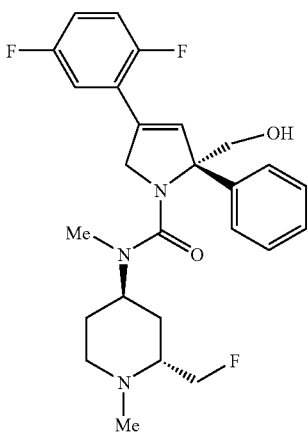

(2S)-4-(2,5-Difluorophenyl)-N-[(2R,4R)-2-(fluoromethyl)-1-methylpiperidin-4-yl]-2-(hydroxymethyl)-N-methyl-2-phenyl-2,5-dihydro-1H-pyrrole-1-carboxamide

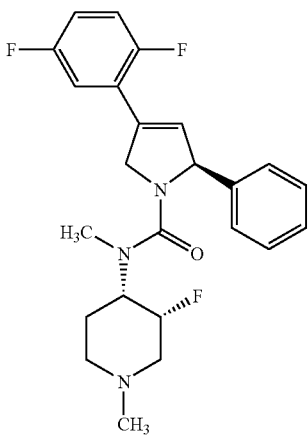

(2S)-4-(2,5-Difluorophenyl)-N-[(3R,4S)-3-fluoro-1-methylpiperidin-4-yl]-N-methyl-2-phenyl-2,5-dihydro-1H-pyrrole-1-carboxamide or a pharmaceutically acceptable salt or stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

When any variable (e.g. $R^4$, $R^7$, $R^{10}$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "alkylene" means a hydrocarbon diradical group having the specified number of carbon atoms. For example, "alkylene" includes —$CH_2$—, —$CH_2CH_2$— and the like.

When used in the phrases "$C_1$-$C_6$ aralkyl" and "$C_1$-$C_6$ heteroaralkyl" the term "$C_1$-$C_6$" refers to the alkyl portion of the moiety and does not describe the number of atoms in the aryl and heteroaryl portion of the moiety.

"Alkoxy" represents either a cyclic or nonyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

Preferably, heterocycle is selected from 2-azepinone, benzimidazolyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl.

As appreciated by those of skill in the art, "halo" or "halogen" as used herein is intended to include chloro, fluoro, bromo and iodo.

The alkyl, alkenyl, alkynyl, cycloalkyl, aryl, heteroaryl and heterocyclyl substituents may be substituted or unsubstituted, unless specifically defined otherwise. For example, a ($C_1$-$C_6$) alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —C(=O)$CH_2$CH(OH)$CH_3$, —(C=O)OH, —$CH_2$(OH)$CH_2$CH(O), and so on.

In certain instances, $R^8$ and $R^9$, $R^c$ and $R^{c1}$ and $R^f$ and $R^{f1}$ are defined such that they can be taken together with the nitrogen to which they are attached to form a monocyclic or bicyclic heterocycle with 5-7 members in each ring and optionally containing, in addition to the nitrogen, one or two additional heteroatoms selected from N, O and S, said heterocycle optionally substituted with one or more substituents selected from $R^7$. Examples of the heterocycles that can thus be formed include, but are not limited to the following, keeping in mind that the heterocycle is optionally substituted with one or more (and in an embodiment, one, two or three) substituents chosen from $R^7$:

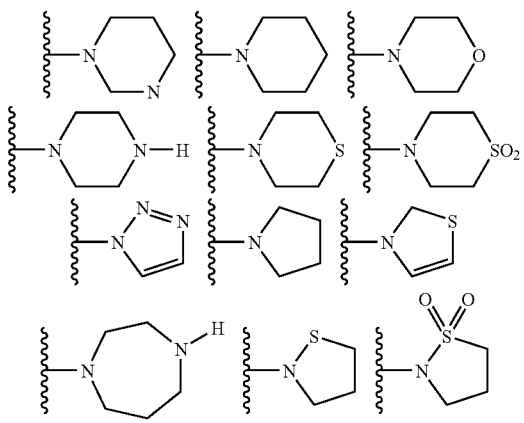

-continued

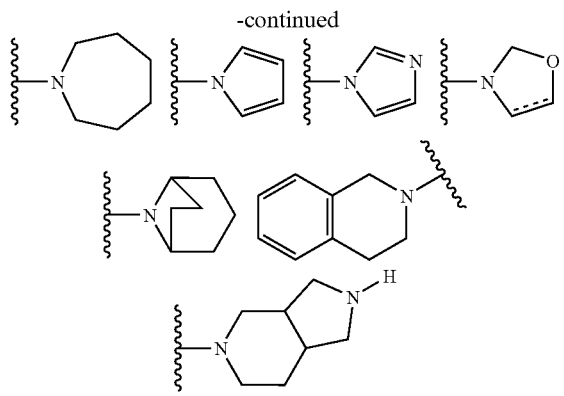

In certain instances, $R^d$ and $R^{d_1}$ are defined such that they can be taken together with the phosphorous to which they are attached to form a monocyclic heterocycle with 5-7 members in the ring and optionally containing, in addition to the nitrogen, one or two additional heteroatoms selected from $NR^e$, O and S, said heterocycle optionally substituted with one or more substituents selected from $R^7$. Examples of the heterocycles that can thus be formed include, but are not limited to the following, keeping in mind that the heterocycle is optionally substituted with one or more (and in an embodiment, one or two) substituents chosen from $R^7$:

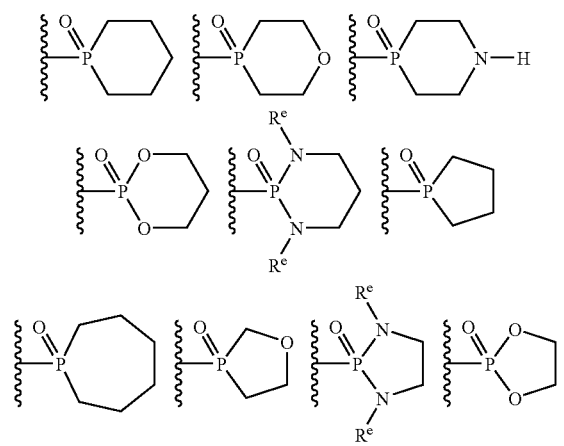

In an embodiment, $R^1$ is selected from H and $C_1$-$C_6$ alkyl.
In an embodiment, $R^2$ is selected from H and $C_1$-$C_6$ alkyl.
In an embodiment, $R^{12}$ is H.
In an embodiment, $R^3$ is selected from —$C_1$-$C_{10}$ alkyl-O—Rg and —$C_1$-$C_{10}$ alkyl-$NR^f R^{f_1}$, optionally substituted with one to two substituents selected from $R^{10}$.
In an embodiment, $R^4$ is independently selected from halogen and OH. In a further embodiment, n is 2 and $R^4$ is independently selected from halogen.
In an embodiment, $R^5$ is independently selected from H, halogen and OH.
In an embodiment, u is 0.
In an embodiment, t is 1, $R^{10}$ is fluoro and $R^{13}$ is H.
In another embodiment, t is 0 and $R^{13}$ is fluoromethyl.
In an embodiment, $R^{ox}$ is absent.
Included in the instant invention is the free form of compounds of Formula I, as well as the pharmaceutically acceptable salts and stereoisomers thereof. Some of the specific compounds exemplified herein are the protonated salts of amine compounds. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamnic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabarnine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharr. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The following abbreviations, used in the Schemes and Examples, are defined below:

| | |
|---|---|
| CDI | 1,1'-carbonyldiimidazole |
| CSP HPLC | Chiral stationary phase high performance liquid chromatography |
| DAST | (diethylamino)sulfur trifluoride |
| DCE | 1,2-dichloroethane |
| DCM | Dichloromethane |
| DMF | Dimethylformamide |
| DMSO | Dimethyl sulfoxide |
| EtOAc | Ethyl acetate |
| IPAC | Isopropyl acetate |
| LAH | Lithium aluminum hydride |
| LiHMDS | Lithium hexamethyldisilazide |
| MsCl | Methanesulfonylchloride |
| NaHMDS | Sodium hexamethyldisilazide |
| NOE | Nuclear Overhauser Effect |
| PTC | Phase transfer catalyst |
| TBSCl | tert-butyldimethylsilyl chloride |
| TEA | Triethylamine |
| TFA | Trifluoroacetic acid |
| THF | Tetrahydrofuran |

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of Formula I hereinabove.

SCHEMES

As shown in Scheme A, key 2,2-disubstituted dihydropyrrole intermediate A-8 may be obtained from readily available suitably substituted α-phenylglycines. Following the procedure described by Van Betsbrugge et. al. (*Tetrahedron*, 1997, 53, 9233-9240) the α-allyl-α-phenylglycine A-3 is prepared. Reduction of the ester and cyclization with carbonyldiimidazole provides intermediate A-4. Ruthenium oxidation of the allylic olefin, followed by ester formation and alkylation of the nitrogen provides intermediate A-5. Cyclization and decarboxylation results in intermediate A-6. The ring carbonyl can then be utilized to incorporate a suitably substituted phenyl moiety. Subsequent saponification and oxygen protection leads to the protected intermediate A-8. The enantiomers of A-8 may often be separated utilizing chiral chromatographic techniques. The ring nitrogen may then be reacted with triphosgene to prepare the activated carbonyl chloride A-9.

Scheme B illustrates the preparation of the fluorinated aminopiperidine B-5, starting with the N-protected piperidone. The cis and trans diastereomeric pairs may often be separated by silica gel chromatography and the enantiomers may often be separated utilizing chiral chromatographic techniques.

As shown in Scheme C, such a fluorinated aminopiperidine may then be reacted with the dihydropyrrole intermediate A-9 to provide the instant compound C-1.

Scheme D illustrates preparation of 2-fluoromethyl-4-aminopiperidine compounds and incorporation of those groups into the compounds of the instant invention. It should be noted that fluoride displacement of the sidechain hydroxyl in intermediate D-3 often leads to both the desired intermediate D4 and the ring homologous compound D-5. These intermediate compounds may be separated by silica gel chromatography.

Scheme E illustrates an alternative preparation of the 2-fluoromethyl-3-aminopiperidine compounds in which the seven-membered ring isomer is not produced.

As shown in Schemes F and G, the hydroxyl moiety of A-9 may undergo alkylation with a variety of reagents.

As illustrated in Scheme H, replacement of the hydroxyl moiety of compound C-1 with a suitably substituted amine proceeds through the corresponding aldehyde H-1, followed by reductive alkylation, resulting in the instant compound H-2.

Scheme I illustrates the synthesis of 2-monosubstituted dihyropyrrole compounds of the instant invention. Preparation and displacement of the methylimidazolyl moiety in intermediate I-7 with the aminopiperidine provides the instant compound 1-8.

Scheme J illustrates homologation of the 2-alkyl sidechain to provide the instant compounds J-3 and J-4.

Schemes K to M illustrate further modifications of the C-2 alkyl sidechain starting with the intermediate aldehyde H-1. Thus in Scheme K, the aldehyde H-1 is treated with a Grignard reagent, such as an alkyl Grignard, to provide the hydroxy compound K-1.

Scheme L illustrates homologation of the C-2 side chain. The aldehyde H-1 is treated with a phosphonoacetate and the conjugated double bond is then reduced to provide the ester L-1. Subsequent reduction of the ester and oxidation of the alcohol provides the aldehyde L-3, which can reductively alkylate a suitably substituted amine to provide the instant compound L-4. Further alkylation of L-4 is also illustrated.

Scheme M illustrates fluorination of the C-2 sidechain and subsequent conversion of the hydroxyl moiety to an amine via displacement of the corresponding triflate with sodium azide.

Scheme N illustrates incorporation of a difluoromethyl moiety into the C-2 sidechain.

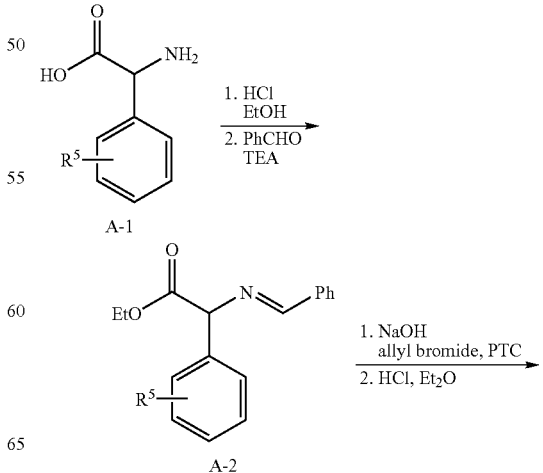

SCHEME A

-continued
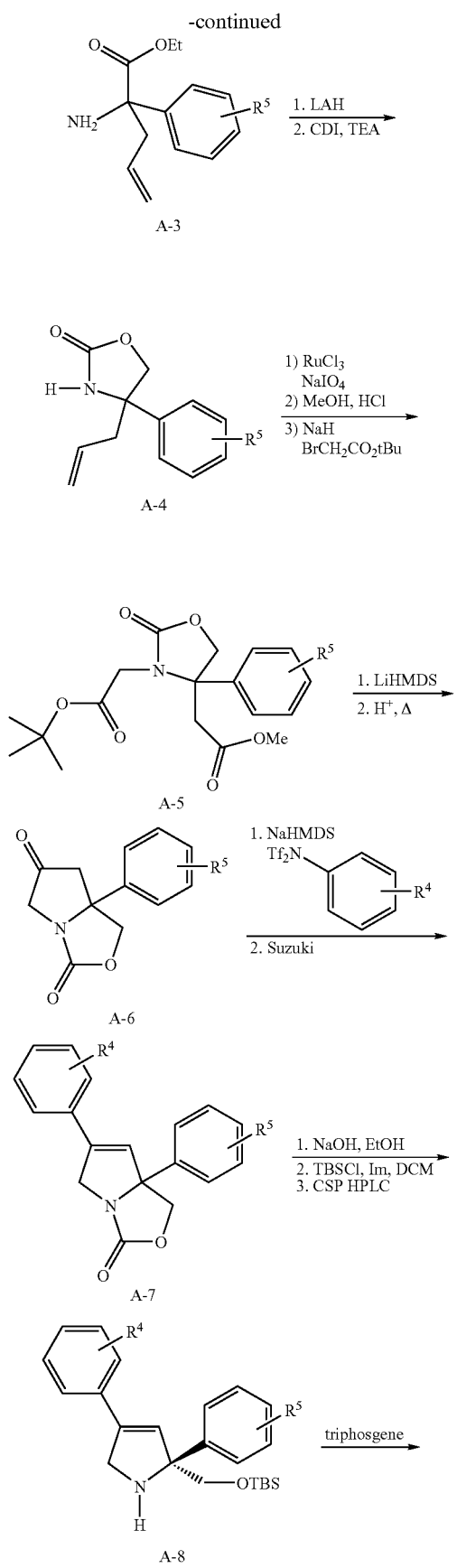
SCHEME B
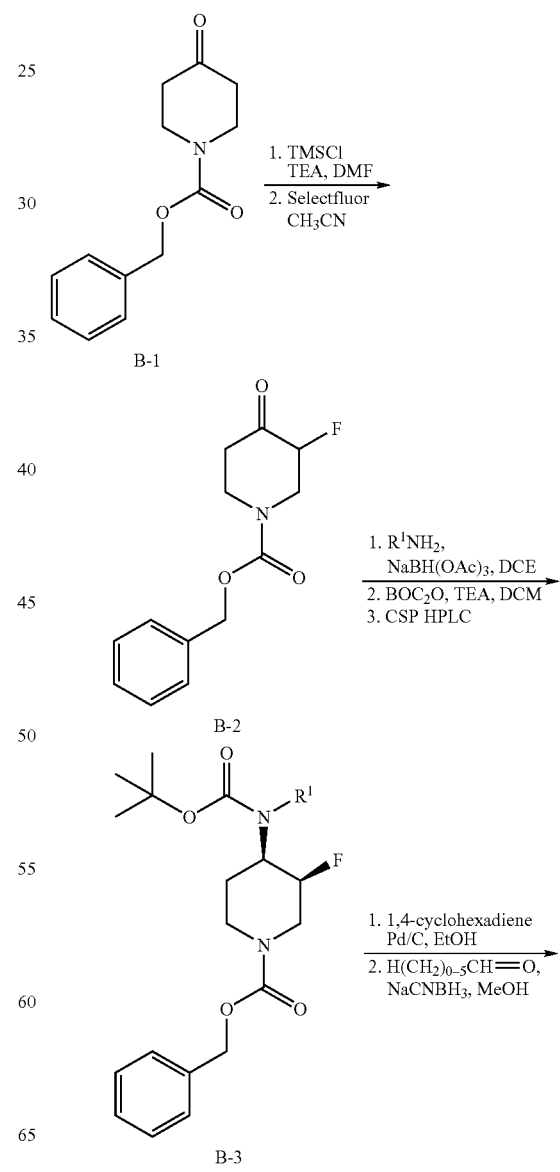

-continued
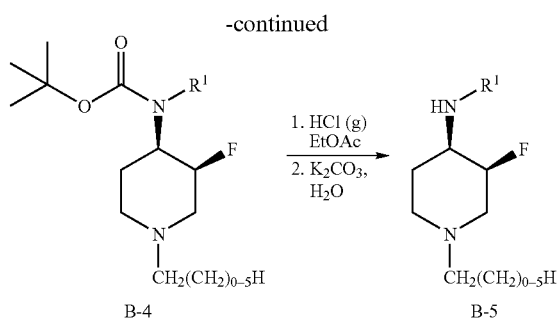
B-4
1. HCl (g) EtOAc
2. K₂CO₃, H₂O
B-5
SCHEME D
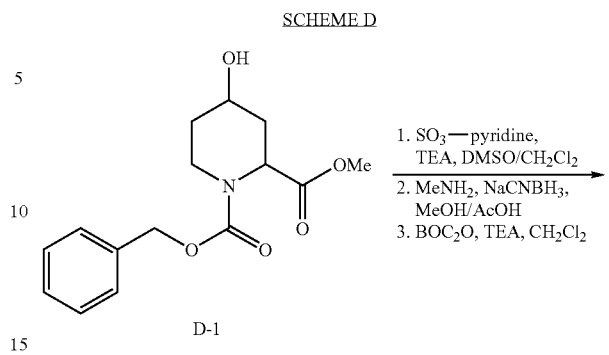
D-1
1. SO₃—pyridine, TEA, DMSO/CH₂Cl₂
2. MeNH₂, NaCNBH₃, MeOH/AcOH
3. BOC₂O, TEA, CH₂Cl₂
SCHEME C
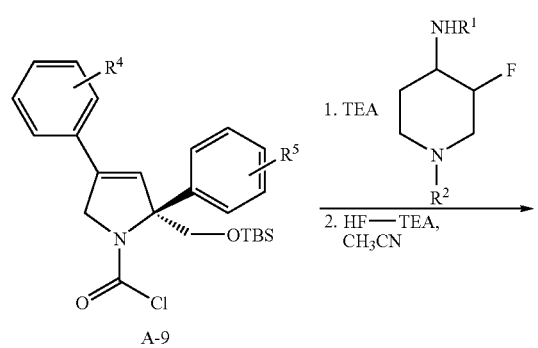
A-9
1. TEA
2. HF—TEA, CH₃CN
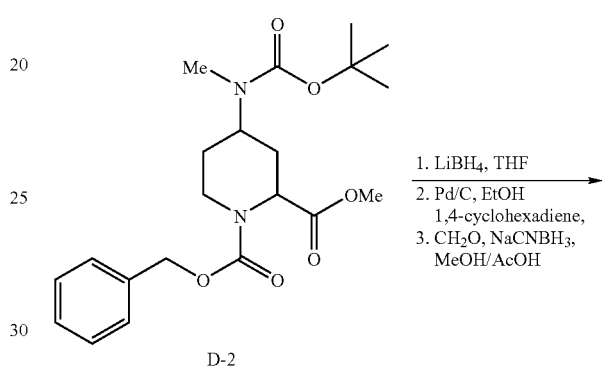
D-2
1. LiBH₄, THF
2. Pd/C, EtOH 1,4-cyclohexadiene
3. CH₂O, NaCNBH₃, MeOH/AcOH
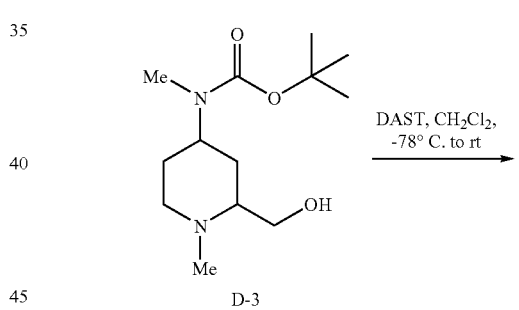
D-3
DAST, CH₂Cl₂, −78° C. to rt
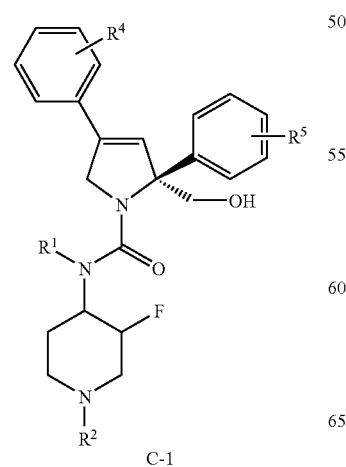
C-1
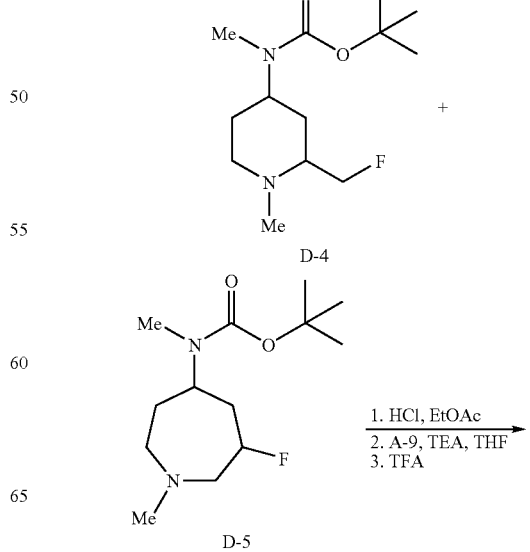
D-4
D-5
1. HCl, EtOAc
2. A-9, TEA, THF
3. TFA -continued
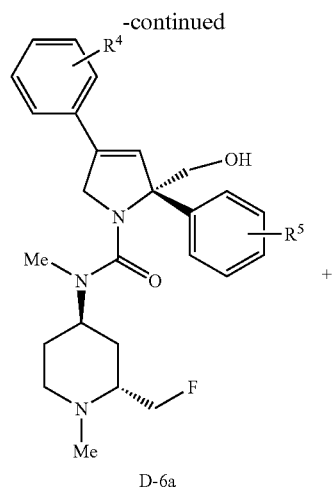
D-6a
+
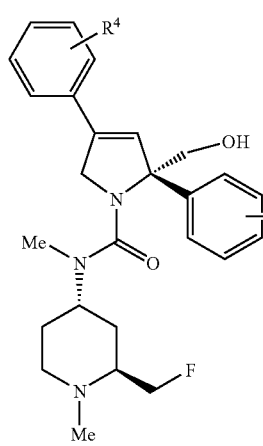
D-6b
SCHEME E
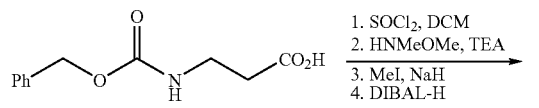
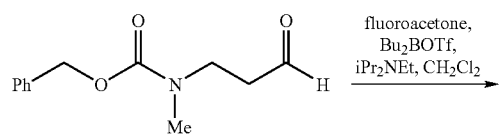
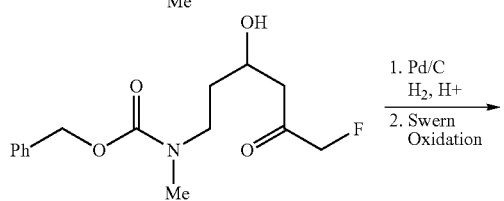
-continued
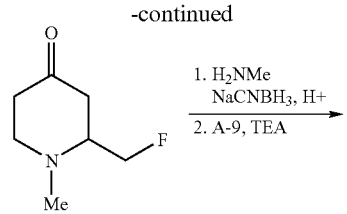
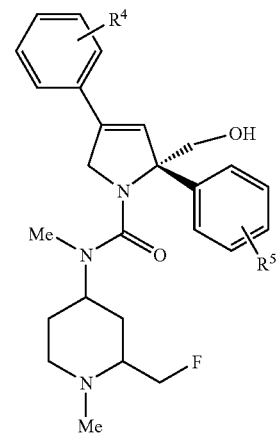
SCHEME F
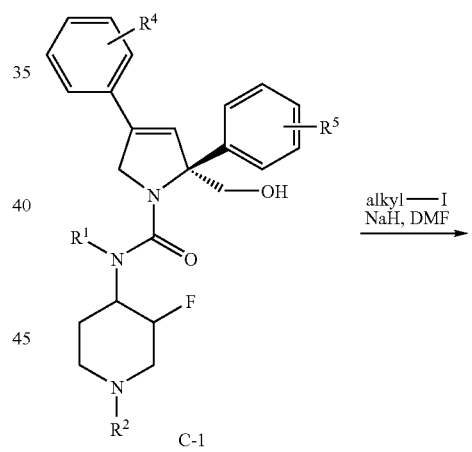
C-1
alkyl—I
NaH, DMF
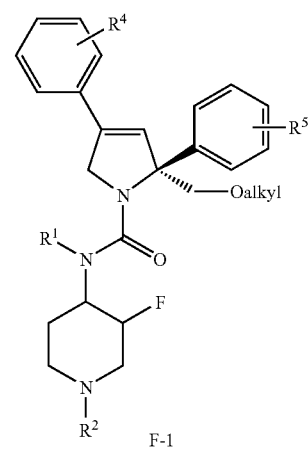
F-1

SCHEME G
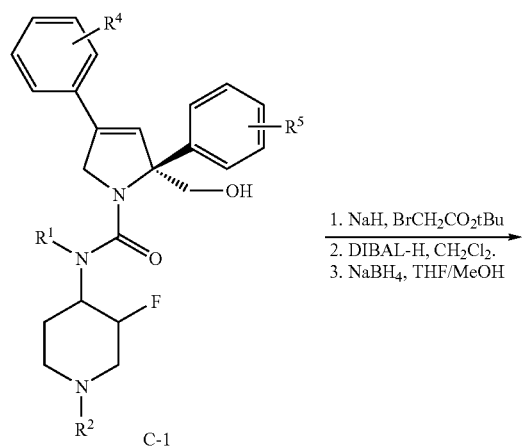
1. NaH, BrCH₂CO₂tBu
2. DIBAL-H, CH₂Cl₂.
3. NaBH₄, THF/MeOH
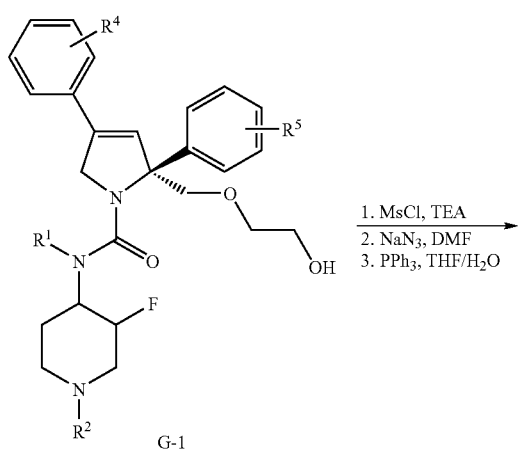
1. MsCl, TEA
2. NaN₃, DMF
3. PPh₃, THF/H₂O
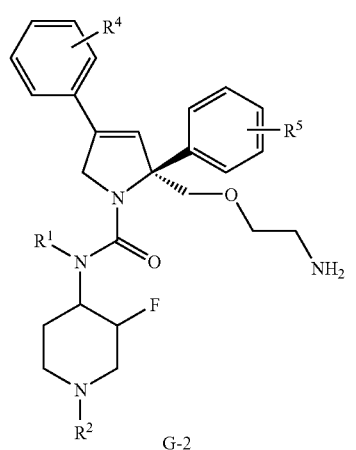
SCHEME H
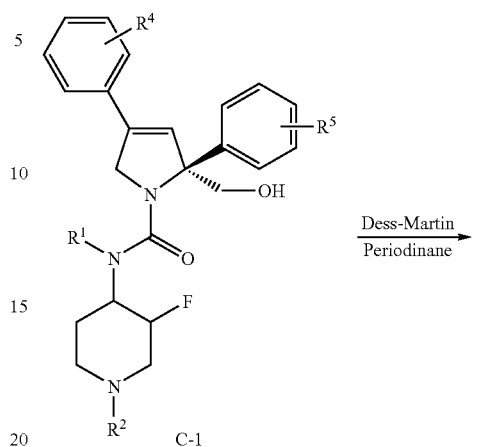
Dess-Martin Periodinane
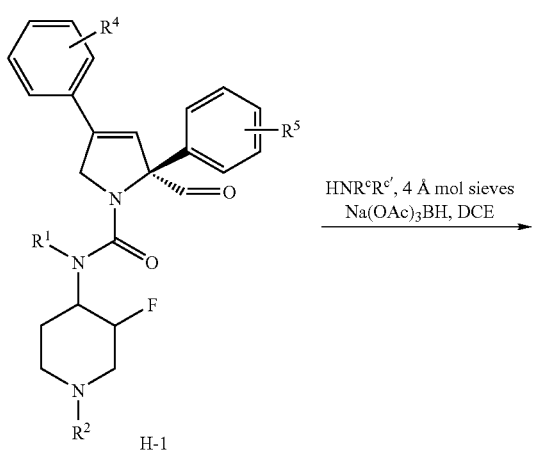
HNR$^c$R$^{c'}$, 4 Å mol sieves
Na(OAc)₃BH, DCE
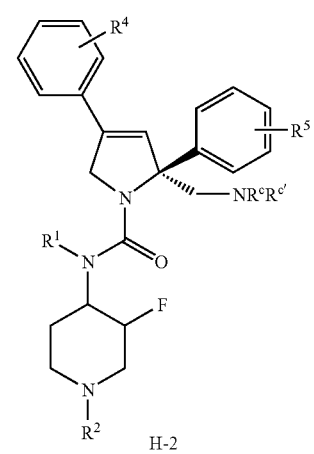

SCHEME I
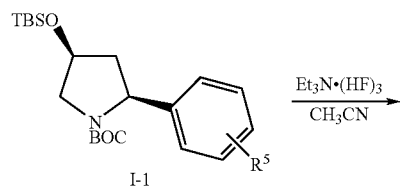
I-1
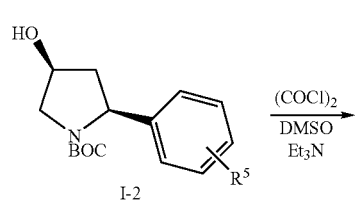
I-2
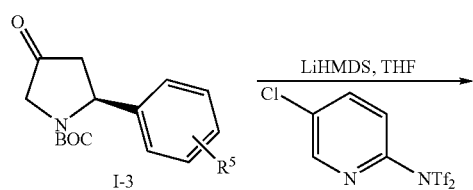
I-3
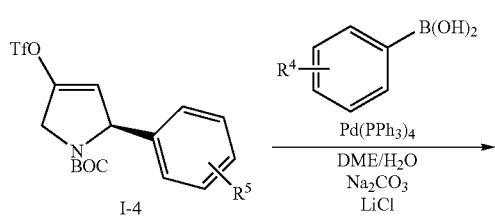
I-4
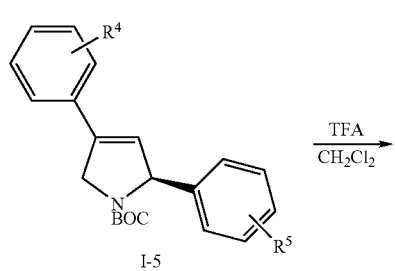
I-5
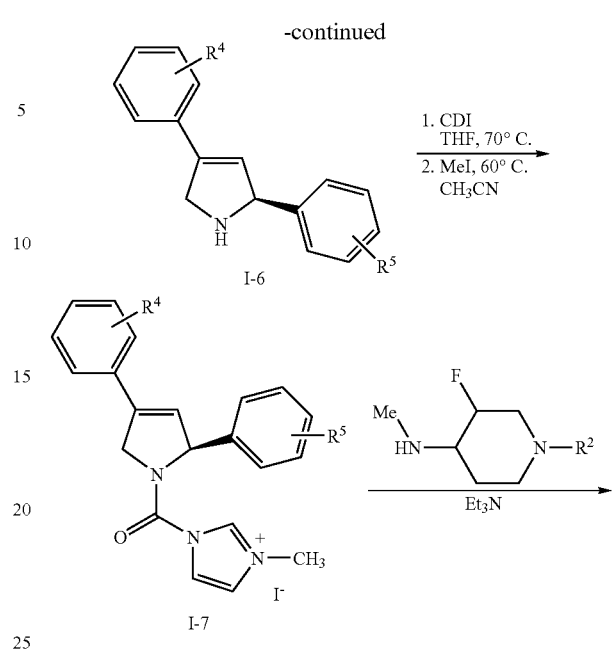
I-6
I-7
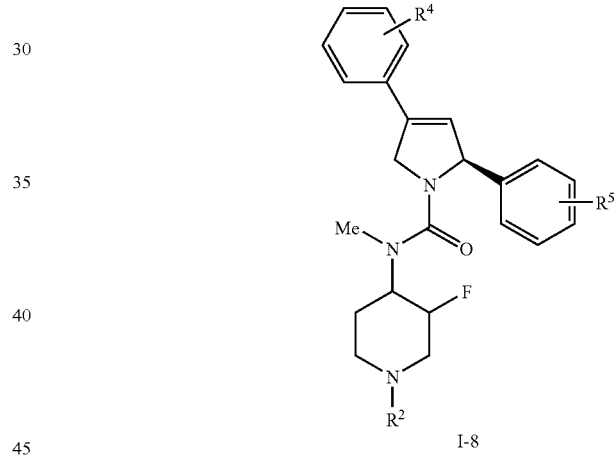
I-8
SCHEME J
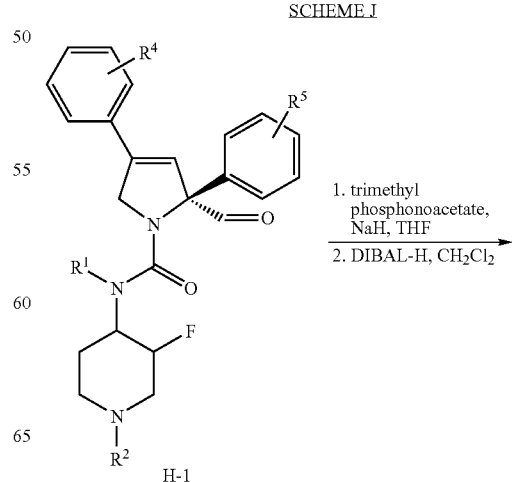
H-1

33
-continued
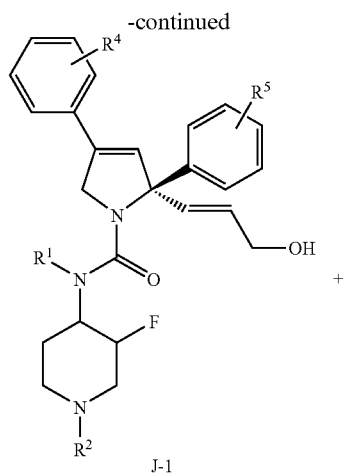
J-1
+
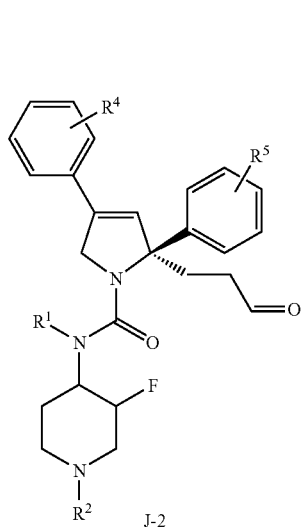
J-2
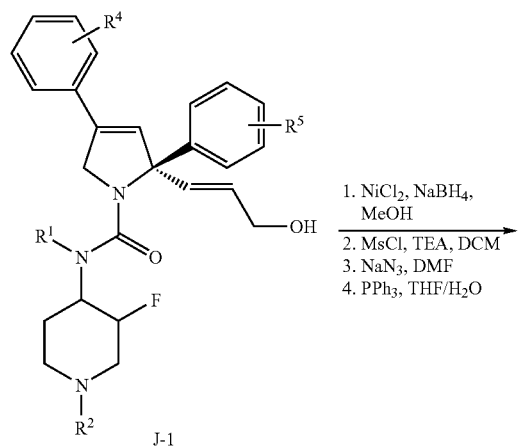
J-1
1. NiCl$_2$, NaBH$_4$, MeOH
2. MsCl, TEA, DCM
3. NaN$_3$, DMF
4. PPh$_3$, THF/H$_2$O
34
-continued
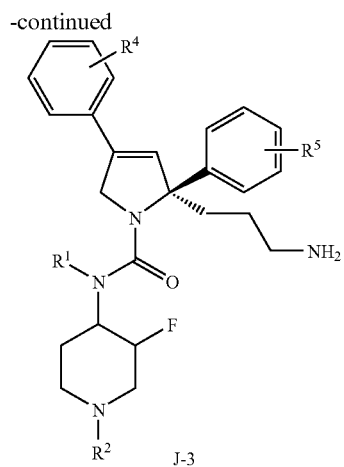
J-3
R$^c$R$^{c'}$NH—HCl, 4Å MS
Na(OAc)$_3$BH, DCE
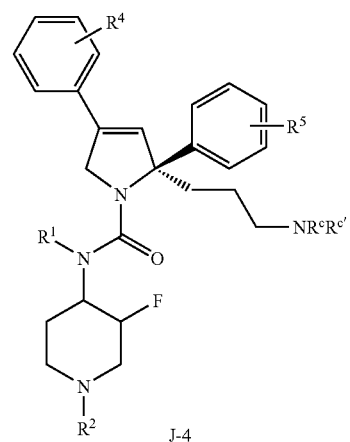
J-4

SCHEME K
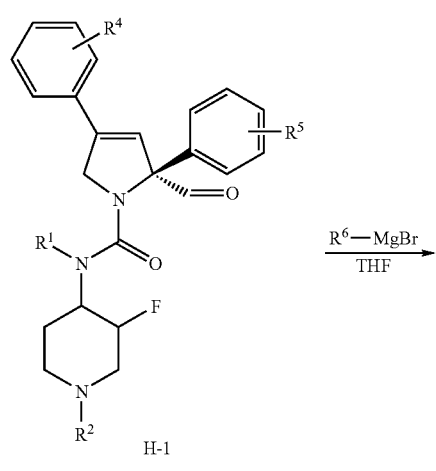
H-1
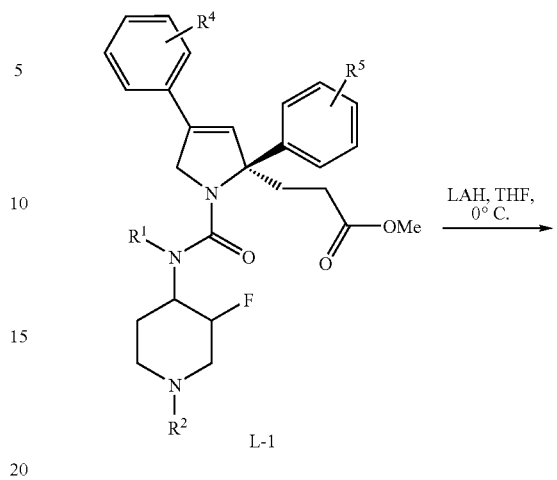
L-1
K-1
L-2
SCHEME L
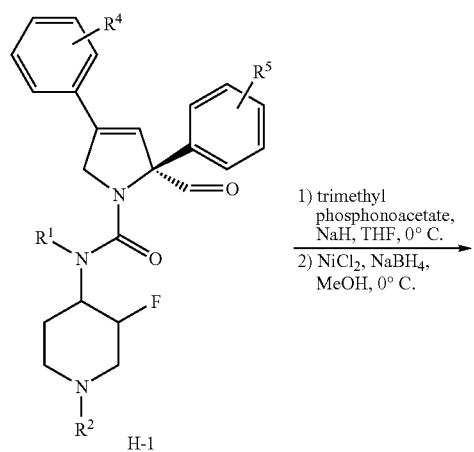
H-1
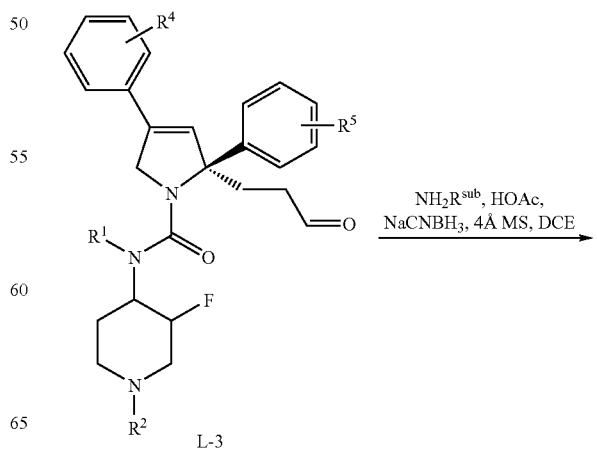
L-3

-continued
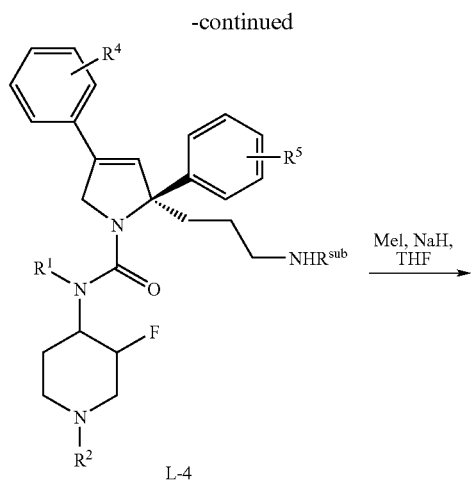
L-4
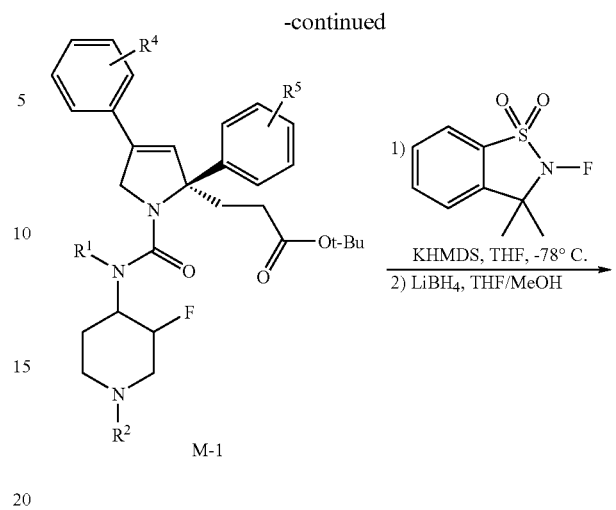
M-1
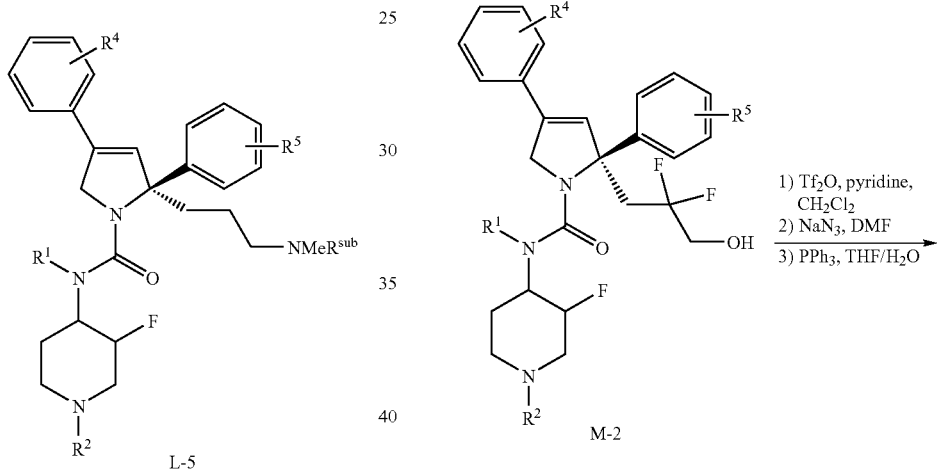
L-5
M-2
SCHEME M
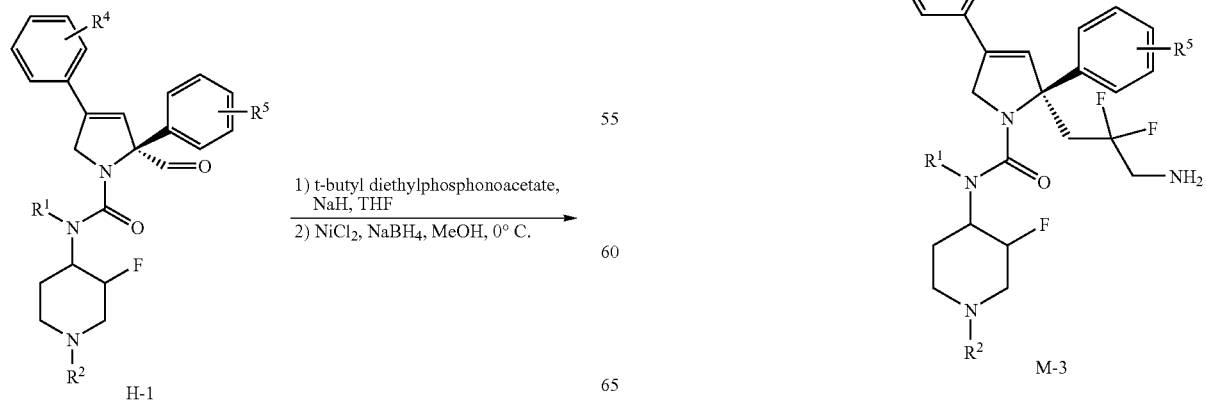
H-1
M-3

SCHEME N

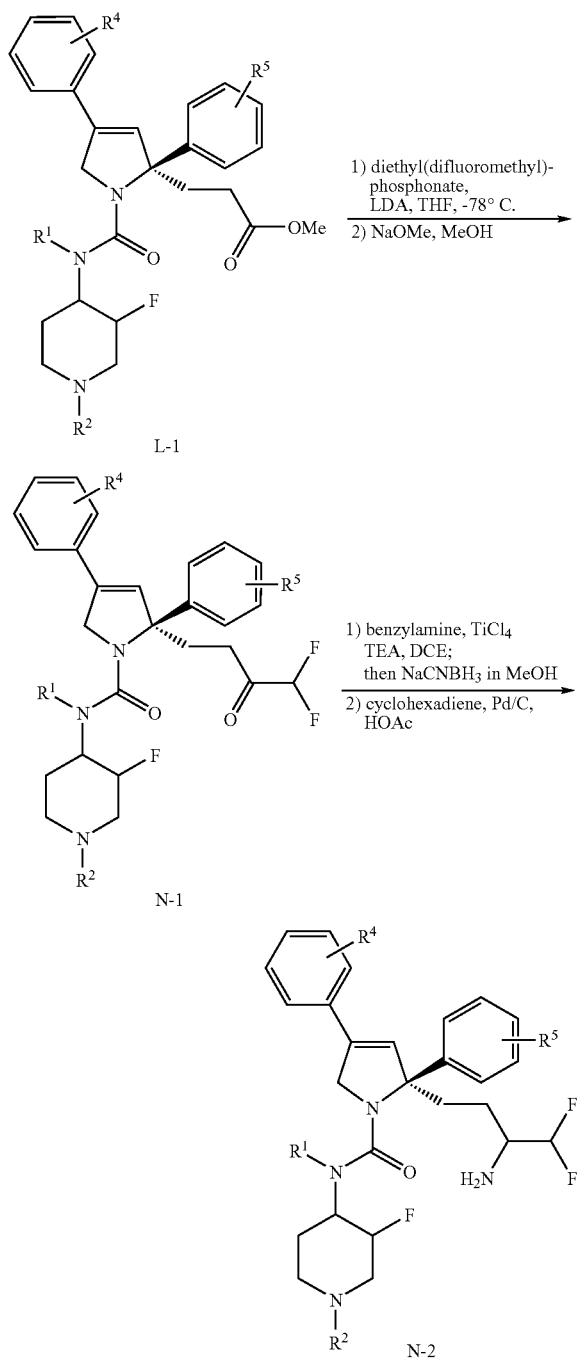

UTILITIES

The compounds of the invention find use in a variety of applications. As will be appreciated by those skilled in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In a preferred embodiment, the compounds of the invention are used to modulate mitotic spindle formation, thus causing prolonged cell cycle arrest in mitosis. By "modulate" herein is meant altering mitotic spindle formation, including increasing and decreasing spindle formation. By "mitotic spindle formation" herein is meant organization of microtubules into bipolar structures by mitotic kinesins. By "mitotic spindle dysfunction" herein is meant mitotic arrest and monopolar spindle formation.

The compounds of the invention are useful to bind to and/or modulate the activity of a mitotic kinesin. In a preferred embodiment, the mitotic kinesin is a member of the bimC subfamily of mitotic kinesins (as described in U.S. Pat. No. 6,284,480, column 5). In a further preferred embodiment, the mitotic kinesin is human KSP, although the activity of mitotic kinesins from other organisms may also be modulated by the compounds of the present invention. In this context, modulate means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. In addition, other mitotic kinesins may be inhibited by the compounds of the present invention.

The compounds of the invention are used to treat cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

The compounds, compositions and methods provided herein are particularly deemed useful for the treatment of cancer including solid tumors such as skin, breast, brain, cervical carcinomas, testicular carcinomas, etc. More particularly, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematoloiic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

The compounds of the instant invention may also be useful as antifungal agents, by modulating the activity of the fungal members of the bimC kinesin subgroup, as is described in U.S. Pat. No. 6,284,480.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

As used herein, the term "composition" is intended to encompass a product comprising the specified ingredients in the specific amounts, as well as any product which results, directly or indirectly, from combination of the specific ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anticancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, LX23-7553, trans-N-(4'-hydroxyphenyl) retinamide, and N4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl4-methylsulphonyl-daunorubicin (see WO 00/50032).

An example of a hypoxia activatable compound is tirapazamine.

Examples of proteasome inhibitors include but are not limited to lactacystin and bortezomib Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro4-methoxyphenyl) benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydroOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis [(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1'-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768 and WO 01/98278, WO 03/050, 064 (Jun. 19, 2003), WO 03/050,122 (Jun. 19, 2003), WO 03/049,527 (Jun. 19, 2003), WO 03/049,679 (Jun. 19, 2003), WO 03/049,678 (Jun. 19, 2003) and WO 03/39460 (May 15, 2003) and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4. 1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2arboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

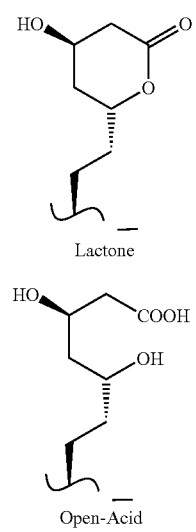

Lactone

Open-Acid

In HMG-CoA reductase inhibitors where an open-acid form can exist, salt and ester forms may be formed from the open-acid, and all such forms are included within the meaning of the term "HMG-CoA reductase inhibitor" as used herein. In an embodiment, the HMG-CoA reductase inhibitor is selected from lovastatin and simvastatin, and in a further embodiment, simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-pchlorobenzyl-2-pyrrolidine-1'-yl-methylbenz-imidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)quinolinone, (−)-6-[amino(4-chlorophenyl)(1-methyl-1H-imidazol-5-yl) methyl]-4-(3-chlorophenyl)-1-methyl-2(1H)-quinolinone, (+)-6-[amino(4-chlorophenyl)(1-methyl-1H-imidazol-5-yl) methyl]-4-(3-chlorophenyl)-1-methyl-2(1H)-quinolinone, 5(S)-n-butyl-1-(2,3-dimethylphenyl)-4-[1-(4-cyanobenzyl)-5-imnidazolylmethyl]-2-piperazinone, (S)-1-(3-chlorophenyl)-4-[1-(4-cyanobenzyl)-5-imidazolylmethyl]-5-[2-(ethanesulfonyl) methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{-[4-hydroxymethyl-4-(4-chloropyridin-2-ylmethyl)-piperidine-1-ylmethyl]-2-methylimidazol-1-ylmethyl}benzonitrile, 4-{-5-[4-hydroxymethyl-4-(3-chlorobenzyl)-piperidine-1-ylmethyl]-2-methylimnidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-ylmethyl}benzonitrile, 4-{3-[4-(2-oxo-2H-[1,2']bipyridin-5'-ylmethyl]-3H-imidazol4-ylmethyl}benzonitrile, 4-{3-(2-oxo-1-phenyl-1,2-dihydropyridin-4-ylmethyl)-3H-imidazol-4-ylmethyl}benzonitrile, 18,19-dihydro-19-oxo-5H, 17H-6,10:12,16-dimetheno-1H-imidazo[4,3-c][1,11,4] dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo [d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No.

5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Patent No. 5,532,359.

For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A4, squalamine, 6-O-chloroacetylcarbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U,S, Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

"Apoptosis inducing agents" include activators of TNF receptor family members (including the TRAIL receptors).

The combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Inhibitors of COX-2 that are particularly useful in the instant method of treatment are:

3-phenyl-4-(4-(methylsulfonyl)phenyl)-2-(5H)-furanone;

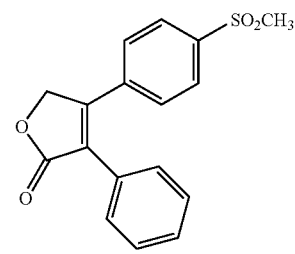

and 5-chloro-3-(4-methylsulfonyl)phenyl-2-(2-methyl-5-pyridinyl)pyridine;

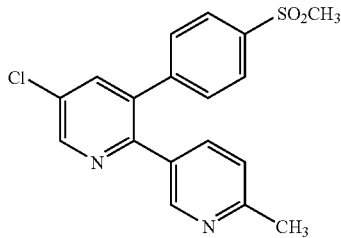

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

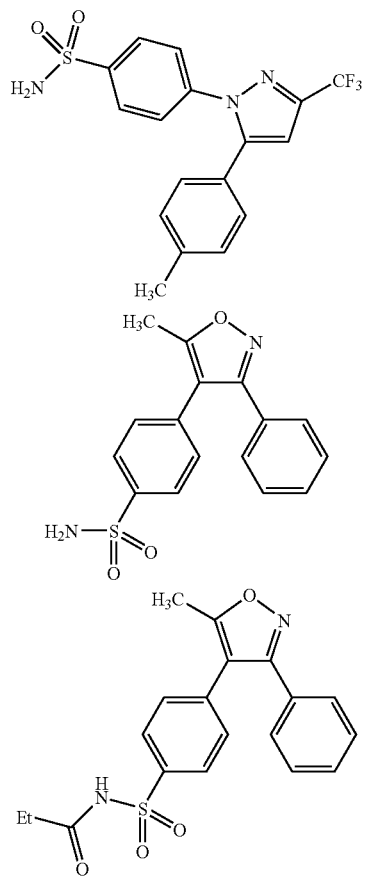

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20,1998.

Other examples of angiogenesis inhibitors include, but are not limited to, endostatin, ukrain, ranpirnase, IM862, 5-methoxy4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or cQunteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$, integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ intergrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999;274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine,* 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998;5(8):1105-13), and interferon gamma (*J Immunol* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. For the treatment or prevention of emesis that may result upon administration of the instant compounds, conjunctive therapy with an anti-emesis agent selected from a neurokinin-1 receptor antagonist, a 5HT3 receptor antagonist and a corticosteroid is preferred.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0498 069, 0499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

Thus, the scope of the instant invention encompasses the use of the instantly claimed compounds in combination with a second compound selected from: 1) an estrogen receptor modulator, 2) an androgen receptor modulator, 3) retinoid receptor modulator, 4) a cytotoxic/cytostatic agent, 5) an antiproliferative agent, 6) a prenyl-protein transferase inhibitor, 7) an HMG-CoA reductase inhibitor, 8) an HIV protease inhibitor, 9) a reverse transcriptase inhibitor, 10) an angiogenesis inhibitor, 11) a PPAR-γ agonists, 12) a PPAR-δ agonists, 13) an inhibitor of inherent multidrug resistance, 14) an anti-emetic agent, 15) an agent useful in the treatment of anemia, 16) an agent useful in the treatment of neutropenia, 17) an immunologic-enhancing drug, 18) an inhibitor of cell proliferation and survival signaling, 19) an agent that interfers with a cell cycle checkpoint, and 20) an apoptosis inducing agent.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: 1) an estrogen receptor modulator, 2) an androgen receptor modulator, 3) retinoid receptor modulator, 4) a cytotoxic/cytostatic agent, 5) an antiproliferative agent, 6) a prenyl-protein transferase inhibitor, 7) an HMG-CoA reductase inhibitor, 8) an HIV protease inhibitor, 9) a reverse transcriptase inhibitor, 10) an angiogenesis inhibitor, 11) a PPAR-γ agonists, 12) a PPAR-δ agonists, 13) an inhibitor of inherent multidrug resistance, 14) an anti-emetic agent, 15) an agent useful in the treatment of anemia, 16) an agent useful in the treatment of neutropenia, 17) an immunologic-enhancing drug, 18) an inhibitor of cell proliferation and survival signaling, 19) an agent that interfers with a cell cycle checkpoint, and 20) an apoptosis inducing agent.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: 1) an estrogen receptor modulator, 2) an androgen receptor modulator, 3) a retinoid receptor modulator, 4) a cytotoxic/cytostatic agent, 5) an antiproliferative agent, 6) a prenyl-protein transferase inhibitor, 7) an HMG-CoA reductase inhibitor, 8) an HIV protease inhibitor, 9) a reverse transcriptase inhibitor, 10) an angiogenesis inhibitor, 11) a PPAR-γ agonist, 12) a PPAR-δ agonists; 13) an inhibitor of cell proliferation and survival signaling, 14) an agent that interfers with a cell cycle checkpoint, and 15) an apoptosis inducing agent.

The invention further comprises the use of the instant compounds in a method to screen for other compounds that bind to KSP. To employ the compounds of the invention in a method of screening for compounds that bind to KSP kinesin, the KSP is bound to a support, and a compound of the invention (which is a mitotic agent) is added to the assay. Alternatively, the compound of the invention is bound to the support and KSP is added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the mitotic agent to KSP may be done in a number of ways. In a preferred embodiment, the mitotic agent (the compound of the invention) is labeled, for example, with a fluorescent or radioactive moiety and binding determined directly. For example, this may be done by attaching all or a portion of KSP to a solid support, adding a labeled mitotic agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific-binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}$I, or with fluorophores. Alternatively, more than one component may be labeled with different labels; using $^{125}$I for the proteins, for example, and a fluorophor for the mitotic agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, preferred embodiments exclude molecules already known to bind to that particular protein, for example, polymer structures such as microtubules, and energy sources such as ATP. Preferred embodiments of assays herein include candidate agents which do not bind the cellular proliferation protein in its endogenous native state termed herein as "exogenous" agents. In another preferred embodiment, exogenous agents further exclude antibodies to KSP.

Candidate agents can encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Competitive screening assays may be done by combining KSP and a drug candidate in a first sample. A second sample comprises a mitotic agent, KSP and a drug candidate. This may be performed in either the presence or absence of microtubules. The binding of the drug candidate is determined for both samples, and a change, or difference in binding between the two samples indicates the presence of an agent capable of binding to KSP and potentially modulating its activity. That is, if the binding of the drug candidate is different in the second sample relative to the first sample, the drug candidate is capable of binding to KSP.

In a preferred embodiment, the binding of the candidate agent is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations may be performed at any temperature which facilitates optimal activity, typically between about 4 and about 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to KSP and thus is capable of binding to, and potentially modulating, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the.candidate agent is labeled, the presence of the label on the support, coupled with a lack of competitor binding, may indicate the candidate agent is capable of binding to KSP.

It may be of value to identify the binding site of KSP. This can be done in a variety of ways. In one embodiment, once KSP has been identified as binding to the mitotic agent, KSP is fragmented or modified and the assays repeated to identify the necessary components for binding.

Modulation is tested by screening for candidate agents capable of modulating the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morphology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non- specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

These and other aspects of the invention will be apparent from the teachings contained herein.

ASSAYS

The compounds of the instant invention described in the Examples were tested by the assays described below and were found to have kinase inhibitory activity. Other assays are known in the literature and could be readily performed by those of skill in the art.

I. Kinesin ATPase In Vitro Assay

Cloning and Expression of Human Poly-Histidine Tagged KSP Motor Domain (KSP(367H))

Plasmids for the expression of the human KSP motor domain construct were cloned by PCR using a pBluescript full length human KSP construct (Blangy et al., Cell, vol. 83, pp1159-1169, 1995) as a template. The N-terminal primer 5'-GCAACGATTAATATGGCGTCGCAGC-CAAATTCGTCTGCGAAG (SEQ.ID.NO.: 1) and the C-terminal primer 5'-GCAACGCTCGAGTCAGTGAT GATG-GTGGTGATGCTGATTCACTTCAGGCTTATTCAATAT (SEQ.ID.NO.: 2) were used to amplify the motor domain and the neck linker region. The PCR products were digested with AseI and XhoI, ligated into the NdeI/XhoI digestion product of pRSETa (Invitrogen) and transformed into $E.\ coli$ vol. BL21 (DE3).

Cells were grown at 37° C. to an $OD_{600}$ of 0.5. After cooling the culture to room temperature expression of KSP was induced with 100 µM IPTG and incubation was continued overnight. Cells were pelleted by centrifugation and washed once with ice-cold PBS. Pellets were flash-frozen and stored –80° C.

Protein Purification

Cell pellets were thawed on ice and resuspended in lysis buffer (50 mM K-HEPES, pH 8.0, 250 mM KCl, 0.1% Tween, 10 mM imidazole, 0.5 mM Mg-ATP, 1 mM PMSF, 2 mM benzimidine, 1× complete protease inhibitor cocktail (Roche)). Cell suspensions were incubated with 1 mg/ml lysozyme and 5 mM β-mercaptoethanol on ice for 10 minutes, followed by sonication (3×30sec). All subsequent procedures were performed at 4° C. Lysates were centrifuged at 40,000×g for 40 minutes. Supernatants were diluted and loaded onto an SP Sepharose column (Pharmacia, 5 ml cartridge) in buffer A (50 mM K-HEPES, pH 6.8, 1 mM MgCl$_2$, 1 mM EGTA, 10 µM Mg-ATP, 1 mM DTT) and eluted with a 0 to 750 mM KCl gradient in buffer A. Fractions containing KSP were pooled and incubated with Ni-NTA resin (Qiagen) for one hour. The resin was washed three times with buffer B (Lysis buffer minus PMSF and protease inhibitor cocktail), followed by three 15-minute incubations and washes with buffer B. Finally, the resin was incubated and washed for 15 minutes three times with buffer C (same as buffer B except for pH 6.0) and poured into a column. KSP was eluted with elution buffer (identical to buffer B except for 150 mM KCl and 250 mM imidazole). KSP-containing fractions were pooled, made 10% in sucrose, and stored at –80° C.

Microtubules are prepared from tubulin isolated from bovine brain. Purified tubulin (>97% MAP-free) at 1 mg/ml is polymerized at 37° C. in the presence of 10 µM paclitaxel, 1 mM DTT, 1 mM GTP in BRB80 buffer (80 mM K-PIPES, 1 mM EGTA, 1 mM MgCl$_2$ at pH 6.8). The resulting microtubules are separated from non-polymerized tubulin by ultracentrifugation and removal of the supernatant. The pellet, containing the microtubules, is gently resuspended in 10 µM paclitaxel, 1 mM DTT, 50 µg/mil ampicillin, and 5 µg/ml chloramphenicol in BRB80.

The kinesin motor domain is incubated with microtubules, 1 mM ATP (1:1 MgCl$_2$: Na-ATP), and compound at 23° C. in buffer containing 80 mM K-HEPES (pH 7.0), 1 mM EGTA, 1 mM DTT, 1 mM MgCl$_2$, and 50 mM KCl. The reaction is terminated by a 2-10 fold dilution with a final buffer composition of 80 mM HEPES and 50 mM EDTA. Free phosphate from the ATP hydrolysis reaction is measured via a quinaldine red/ammonium molybdate assay by adding 150 µl of quench C buffer containing a 2:1 ratio of quench A:quench B. Quench A contains 0.1 mg/ml quinaldine red and 0.14% polyvinyl alcohol; quench B contains 12.3 mM ammonium molybdate tetrahydrate in 1.15 M sulfuric acid. The reaction is incubated for 10 minutes at 23° C., and the absorbance of the phospho-molybdate complex is measured at 540 nm.

The compounds 3-1, 4-2, 5-3, 54, 7-1, 7-2, 7-3, 8-6a/8-6b, 9-1, 10-2, 11-1, 12-1, 12-2 and 12-3 in the Examples were tested in the above assay and found to have an $IC_{50} \leqq 50$ µM.

II. Cell Proliferation Assay

Cells are plated in 96-well tissue culture dishes at densities that allow for logarithmic growth over the course of 24, 48, and 72 hours and allowed to adhere overnight. The following day, compounds are added in a 10-point, one-half log titration to all plates. Each titration series is performed in triplicate, and a constant DMSO concentration of 0.1% is maintained throughout the assay. Controls of 0.1% DMSO alone are also included. Each compound dilution series is made in media without serum. The final concentration of serum in the assay is 5% in a 200 µL volume of media. Twenty microliters of Alamar blue staining reagent is added to each sample and control well on the titration plate at 24, 48, or 72 hours following the addition of drug and returned to incubation at 37° C. Alamar blue fluorescence is analyzed 6-12 hours later on a CytoFluor II plate reader using 530-560 nanometer wavelength excitation, 590 nanometer emission.

A cytotoxic $EC_{50}$ is derived by plotting compound concentration on the x-axis and average percent inhibition of cell growth for each titration point on the y-axis. Growth of cells in control wells that have been treated with vehicle alone is defined as 100% growth for the assay, and the growth of cells treated with compounds is compared to this value. Proprietary in-house software is used to calculate percent cytotoxicity values and inflection points using logistic 4-parameter curve fitting. Percent cytotoxicity is defined as:

$$\% \text{ cytotoxicity:} (\text{Fluorescence}_{control}) - (\text{Flourescence}_{sample}) \times 100 \times (\text{Fluorescence}_{control})^{-1}$$

The inflection point is reported as the cytotoxic $EC_{50}$.

III. Evaluation of Mitotic Arrest and Apoptosis by FACS

FACS analysis is used to evaluate the ability of a compound to arrest cells in mitosis and to induce apoptosis by measuring DNA content in a treated population of cells. Cells are seeded at a density of 1.4×10$^6$ cells per 6 cm$^2$ tissue culture dish and allowed to adhere overnight. Cells are then treated with vehicle (0.1% DMSO) or a titration series of compound for 8-16 hours. Following treatment, cells are harvested by trypsinization at the indicated times and pelleted by centrifugation. Cell pellets are rinsed in PBS and fixed in 70% ethanol and stored at 4° C. overnight or longer.

For FACS analysis, at least 500,000 fixed cells are pelleted and the 70% ethanol is removed by aspiration. Cells are then incubated for 30 min at 4° C. with RNase A (50 Kunitz units/ml) and propidium iodide (50 µg/ml), and analyzed using a Becton Dickinson FACSCaliber. Data (from 10,000 cells) is analyzed using the Modfit cell cycle analysis modeling software (Verity Inc.).

An $EC_{50}$ for mitotic arrest is derived by plotting compound concentration on the x-axis and percentage of cells in the G2/M phase of the cell cycle for each titration point (as measured by propidium iodide fluorescence) on the y-axis. Data analysis is performed using the SigmaPlot program to calculate an inflection point using logistic 4-parameter curve fitting. The inflection point is reported as the $EC_{50}$ for mitotic arrest. A similar method is used to determine the compound $EC_{50}$ for apoptosis. Here, the percentage of apoptotic cells at each titration point (as determined by propidium iodide fluorescence) is plotted on the y-axis, and a similar analysis is carried out as described above.

VI. Immunofluorescence Microscopy to Detect Monopolar Spindles

Methods for immunofluorescence staining of DNA, tubulin, and pericentrin are essentially as described in Kapoor et al. (2000) J. Cell Biol. 150: 975-988. For cell culture studies, cells are plated on tissue culture treated glass chamber slides and allowed to adhere overnight. Cells are then incubated with the compound of interest for 4 to 16 hours. After incubation is complete, media and drug are aspirated and the chamber and gasket are removed from the glass slide. Cells are then permeabilized, fixed, washed, and blocked for non-specific antibody binding according to the referenced protocol. Paraffin-embedded tumor sections are deparaffinized with xylene and rehydrated through an ethanol series prior to blocking. Slides are incubated in primary antibodies (mouse monoclonal anti-ot-tubulin antibody, clone DM1A from Sigma diluted 1:500; rabbit polyclonal anti-pericentrin antibody from Covance, diluted 1:2000) overnight at 4° C. After washing, slides are incubated with conjugated secondary antibodies (FITC-conjugated donkey anti-mouse IgG for tubulin; Texas red-conjugated donkey anti-rabbit IgG for pericentrin) diluted to 15 µg/ml for one hour at room temperature. Slides are then washed and counterstained with Hoechst 33342 to visualize DNA. Immunostained samples are imaged with a 100× oil immersion objective on a Nikon epifluorescence microscope using Metamorph deconvolution and imaging software.

EXAMPLES

Examples provided are intended to assist in a further understanding of the invention. Particular materials employed, species and conditions are intended to be illustrative of the invention and not limiting of the reasonable scope thereof.

SCHEME 1

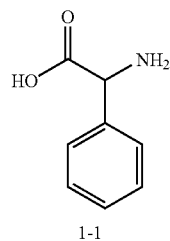
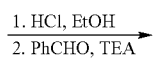

1-1

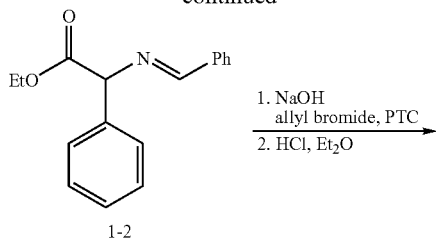
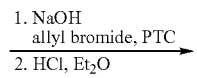

1-2

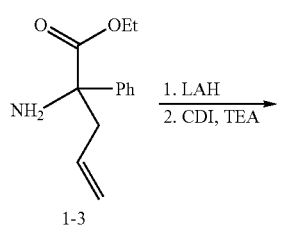

1-3

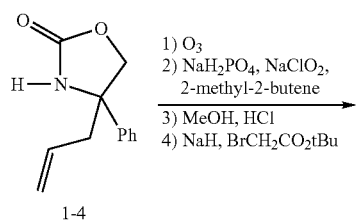
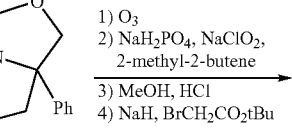

1-4

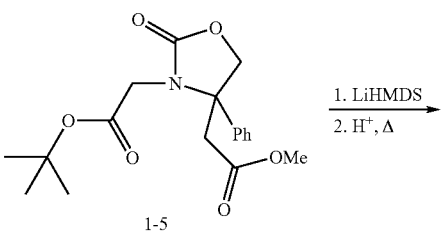

1-5

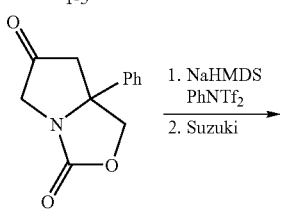
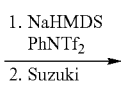

1-6

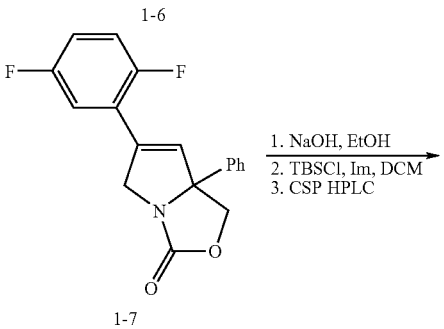
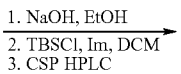

1-7

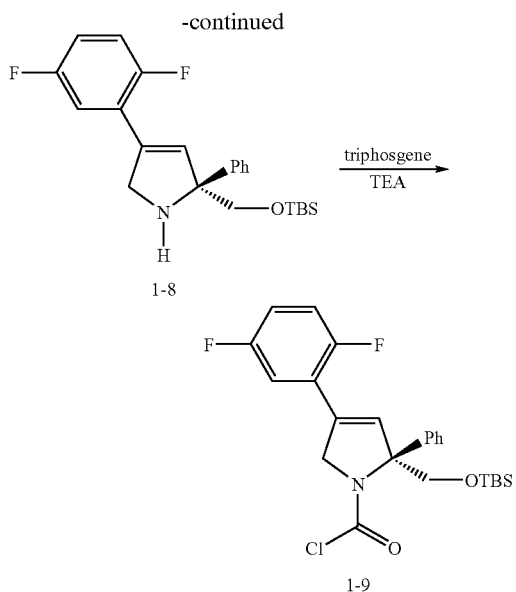

Step 1: 4-Allyl-4-phenyl-1,3-oxazolidin-2-one (1-4)

To a suspension of 15.8 g (416 mmol) of LAH powder in 600 mL of diethyl ether was added 18.3 g (90 mmol) of α-allyl-α-phenylglycine ethyl ester (1-3) (prepared according to: Van Betsbrugge et. al. *Tetrahedron*, 1997, 53, 9233-9240) in 75 mL of diethyl ether at such a rate as to maintain gentle reflux. After stirring overnight at room temperature, the reaction was carefully quenched with 27 mL of water, followed by 27 mL of 15% NaOH and finally 82 mL of water. A quantity of $Na_2SO_4$ was added, and the mixture was stirred for 1 h. The solids were then filtered off and the solution concentrated. The residue was dissolved in 300 mL of $CH_2Cl_2$, dried over $Na_2SO_4$, and concentrated to provide the amino alcohol as a colorless oil. The amino alcohol (4.5 g, 25 mmol) was dissolved in 50 mL of $CH_2Cl_2$ and cooled to 0° C. Following the addition of 5.4 mL (53 mmol) of triethylamnine and 4.5 g (28 mmol) of 1,1′-carbonyldiimidazole, the mixture was warmed to room temperature and allowed to stir for 4 h. The reaction was then dumped into a separatory funnel, washed twice with 1M HCl, water, dried over $Na_2SO_4$, and concentrated to obtain oxazolidinone 1-4 as a colorless oil. Data for 1-4: $^1$HNMR (500 MHz, $CDCl_3$) δ 7.4-7.2 (m, 5H), 6.6 (s, 1H), 5.6-5.5 (m, 1H), 5.2 (m, 2H), 4.5 (d, 1H), 4.35 (d, 1H), 2.8 (m, 1H), 2.6 (m, 1H) ppm.

Step 2: Diester (1-5)

A solution of 68 g (334.6 mmol) of 1-4 in 500 mL of $CH_2Cl_2$ was cooled to −78° C. and ozone was bubbled through the solution until a pale blue color persisted. $O_2$ was then bubbled through the solution for 15 minutes, followed by 30 minutes with $N_2$. At that time, 491 mL (6.7 moles) of dimethyl sulfide was added, and the solution was stirred overnight while slowly coming to room temperature. The volatiles were removed by rotary evaporation to provide a brown oil. This material was suspended in 1 L of tBuOH, and 200 mL (1.9 moles) of 2-methyl-2-butene was added. To this solution was then added dropwise a mixture of 160 g (1.33 moles) of $NaH_2PO_4$ and 70 g (774 mmol) of $NaClO_2$ in 800 mL of $H_2O$. After the addition was complete, the mixture was stirred for an additional 4 h. After separating the layers, the organic was concentrated by rotary evaporation, the residue was dissolved in EtOAc and placed in a separatory funnel with the aqueous phase from the reaction. After separation, the aqueous phase was extracted 3× with EtOAc, dried over $Na_2SO_4$, and concentrated to provide ~90 g of a yellow gum. This residue was suspended in 500 mL of MeOH, and HCl gas was bubbled through the solution until it was nearly refluxing. The flask was then capped and allowed to stir overnight while cooling to room temperature. The volitiles were removed by rotary evaporation, the residue was loaded onto a silica gel column in $CH_2Cl_2$, and eluted with EtOAc/hexanes to provide the methyl ester as a pale orange gum. This residue was dissolved in 500 mL of THF, cooled to 0° C., and 32.6 mL (220.5 mmol) of tert-butyl bromoacetate was added, followed by 10.6 g of NaH (264.6 mmol of a 60% suspension). After the mixture was allowed to warm to room temperature and stir overnight, it was quenched with a saturated $NH_4Cl$ solution, and extracted twice with EtOAc. The combined organic layers were then washed with brine, dried over $Na_2SO_4$, concentrated, and the residue purified by silica gel chromatography with EtOAc/hexanes to provide 1-5 as a thick pale yellow gum. Data for 1-5: $^1$HNMR (500 MHz, $CDCl_3$) δ 7.4-7.3 (m, 5H), 4.65 (d, 1H), 4.55 (d, 1H), 3.9 (d, 1H), 3.65 (s, 3H), 3.5 (d, 1H), 3.35 (d, 1H), 3.2 (d, 1H), 1.4 (s, 9H) ppm. HRMS (ES) calc'd M+Na for $C_{18}H_{23}NO_6$: 372.1423. Found: 372.1412.

Step 3: 7a-Phenyldihydro-1H-pyrrolo[1,2-c][1,3]oxazole-3,6(5H)-dione (1-6)

To a solution of 18.6 g (53 mmol) of 1-5 in 150 mL of THF at −78° C. was added dropwise 58.6 mL (58.6 mmol) of a 1M solution of LiHMDS in THF. After stirring for 1 h at that temperature, the cooling bath was removed and the reaction was allowed to warm to room temperature and stir overnight. The mixture was quenched with a saturated $NH_4Cl$ solution, extracted twice with EtOAc, washed twice with brine, dried over $Na_2SO_4$ and concentrated. The residue was dissolved in 60 mL of formic acid and heated at 100° C. for 24 h. The volatiles were removed under vacuum and the residue was triturated with $CH_2Cl_2$/hexanes/$Et_2O$ to provide 1-6 as a beige solid. Data for 1-6: $^1$HNMR (500 MHz, $CDCl_3$) δ 7.5-7.3 (mn, 5H), 4.7 (d, 1H), 4.3 (d, 1H), 4.2 (d, 1H), 3.5 (d, 1H), 3.1 (d, 1H), 2.95 (d, 1H), 2.9 (d, 1H) ppm.

Step 4: 6-(2,5-Difluorophenyl)-7a-phenyl-5,7a-dihydro-1H-pyrrolo[1,2-c][1,3]oxazol-3-one (1-7)

To a suspension of 2.2 g (10 mmol) of 1-7 in 150 mL of THF at −78° C. was added dropwise 12.2 mL (12.2 mmol) of a 1M solution of NaHMDS in THF. After stirring for 30 min, the solution was allowed to warm to 0° C. and held there for 1 h. The solution was then cooled back down to −78° C. and a solution of 4.35 g (12.2 mmol) of N-phenylbis(trifluoromethanesulphonimide) in 10 mL of THF was added. The cooling bath was removed and the mixture was allowed to warm to room temperature and stir overnight. The mixture was quenched with a saturated $NH_4Cl$ solution, extracted twice with EtOAc, washed twice with brine, dried over $Na_2SO_4$ and concentrated. The residue was dissolved in 75 mL of DME and 18 mL of water. To this mixture was added 1.29 g (30 mmol) of LiCl, 3.2 g (30 mmol) of $Na_2CO_3$, and 4.8 g (30 mmol) of 2,5-difluorophenylboronic acid. The solution was then degassed with $N_2$ for 1 minute, followed by the addition of 630 mg (0.5 mmol) of tetrakis(triphenylphosphine) palladium (0). The reaction was heated at 90° C. for 3 h, cooled to room temperature, diluted with saturated $NaHCO_3$, and extracted twice with EtOAc. The combined organic layers were washed with brine, dried over $Na_2SO_4$, concentrated, and the residue purified by silica gel chromatography with $CH_2Cl_2$/hexanes to provide 1-7 as a white solid. Data for 1-7: $^1$HNMR (500 MHz, $CDCl_3$) δ 7.5-7.3

(mn, 5H), 7.1-6.9 (m, 3H), 6.8 (s, 1H), 4.9 (d, 1H), 4.75 (d, 1H), 4.5 (d, 1H), 4.25 (d, 1H) ppm. HRMS (ES) calc'd M+H for $C_{18}H_{13}F_2NO_2$: 314.0987. Found: 314.0993.

Step 5: 2-({[tert-Butyl(dimethyl)silyl]oxy}methyl)-4-(2,5-difluorophenyl)-2-phenyl-2,5-dihydro-1H-pyrrole (1-8)

A suspension of 1.75 g (5.6 mmol) 1-7 in 15 mL of EtOH and 10 mL of 3 M NaOH was heated at 60° C. for 3 h, cooled to room temperature and dumped into a separatory funnel with EtOAc and brine. The layers were separated, the aqueous phase was extracted twice with EtOAc, the combined organic phases were washed twice with brine, dried over $Na_2SO_4$, and concentrated to provide a white solid. To this flask was added 30 mL of $CH_2Cl_2$, 1.5 g (22.3 mmol) of imidazole and 1.76 g (11.7 mmol) of TBSCl, and the resultant suspension was stirred overnight. The reaction was diluted with $CH_2Cl_2$, washed twice with water, dried over $Na_2SO_4$, concentrated, and the residue purified by silica gel chromatography with EtOAc/hexanes to provide 1-8 as a white solid. Data for 1-8: $^1$HNMR (500 MHz, $CDCl_3$) δ 7.6-7.3 (m, 5H), 7.1-6.9 (m, 3H), 6.75 (s, 1H), 4.25 (d, 1H), 4.1 (d, 1H), 3.95 (d, 1H), 3.75 (d, 1H), 0.9 (s, 9H), 0.1 (s, 3H), 0.05 (s, 3H) ppm.

Step 6: Enantiomeric resolution of Intermediate 1-8

Resolution of the enantiomers was carried out chromatographically using a Chiralpak AD© 10×50 cm column with 1% isopropanol in hexanes (with 0.1% diethylamine) at 150 mL/min. Analytical HPLC analysis of the eluent on a 4×250 mm Chiralpak AD® column with 1% isopropanol in hexanes (with 0.1% diethylamine) at 1 mL/min indicated that first eluting, active enantiomer has $R_t$=5.5 min and the second enantiomer has $R_t$=6.9 min.

Step 7: (2S)-2-{[tert-Butyl(dimethyl)silyl]oxy}methyl)-4-(2,5-difluorophenyl)-2-phenyl-2,5-dihydro-1H-pyrrole-1-carbonyl chloride 1-9

To a solution of 1.95 g (6.6 mmol) of triphosgene in 25 mL of THF at 0° C. was added a solution of 1.31 g (3.3 mmol) of the first eluting enantiomer of 1-8 and 915 μL (6.6 mmol) of triethylamine in 10 mL of THF. The ice bath was removed and the reaction was allowed to warm to room temperature and stir for 3 h. The reaction was then partitioned between water and EtOAc, the organic solution was dried over $Na_2SO_4$, and concentrated to provide 1-9 as a brown oil. Data for 1-9: HRMS (ES) calc'd M+H for $C_{24}H_{28}ClF_2NO_2Si$: 464.1619. Found: 464.1625.

Alternate Synthesis of Diester 1-5

To a biphasic mixture of 14.8 g (73 mmol) of 1-4 and 110 mL of $CH_2Cl_2$, 110 mL of $CH_3CN$, and 320 mL of water was added approximately 200 mg of ruthenium(E) chloride hydrate. Sodium periodate (85.6 g, 400 mmol) was then added portion-wise over 1 h with rapid stirring. After the addition was complete, the reaction was allowed to stir for 4 h more at room temperature. The mixture was diluted with 500 mL of water and 1.5 L of EtOAc, and the solids were removed by filtration. The filtrate was placed in a separatory funnel, the phases separated, the aqueous phase extracted twice with EtOAc, the combined organic phases washed twice with brine, and dried over $Na_2SO_4$. Following concentration, the dark brown solid was dissolved in 250 mL of MeOH and HCl(g) was slowly passed through the solution at a rate so as not to increase the temperature of the solution above 35° C. After 5 min, the reaction was capped and allowed to stir at room temperature overnight. The volatiles were then removed on a rotary evaporator, and the residue was purified by silica gel chromatography with EtOAc/hexanes to provide 13.6 g (58 mmol) of the methyl ester as a viscous oil. This residue was then dissolved in 200 mL of THF, cooled to 0° C., and 10.3 mL (70 mmol) of tert-butyl bromoacetate was added, followed by 2.8 g of NaH (70 mmol of a 60% suspension). After the mixture was allowed to warm to room temperature and stir overnight, it was quenched with a saturated $NH_4Cl$ solution, and extracted twice with EtOAc. The combined organic layers were then washed with brine, dried over $Na_2SO_4$, concentrated, and the residue purified by silica gel chromatography with EtOAc/hexanes to provide 1-5 as a colorless oil.

SCHEME 1B

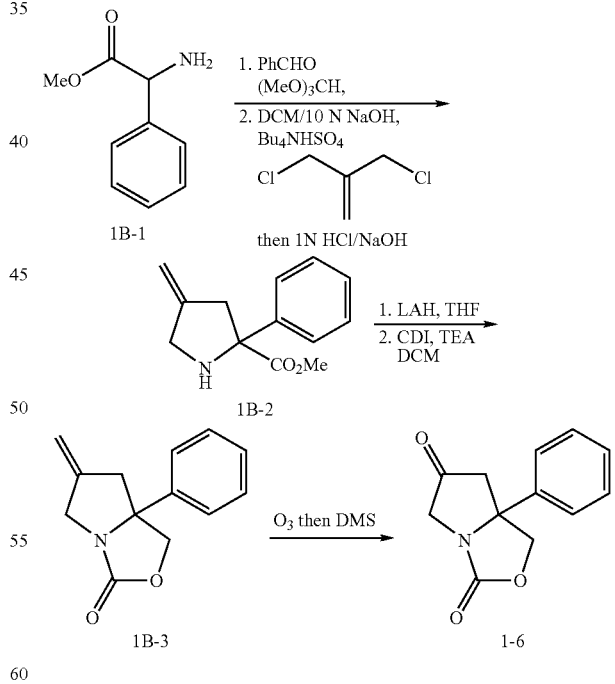

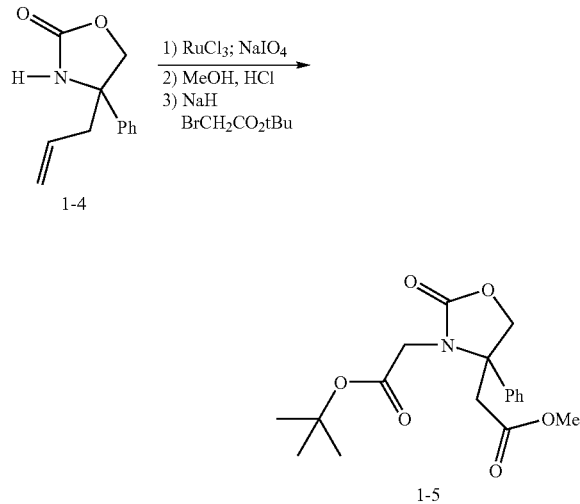

SCHEME 1A

Step 1: Methyl 4-methylene-2-phenylprolinate (1B-2)

An aqueous solution (300 mL) of phenyl glycine methyl ester-HCl (100 g) was neutralized to pH 8 with 10N NaOH. The aqueous solution was extracted with EtOAc (3×200 mL). The combined organic extracts were dried over $MgSO_4$, filtered, and concentrated. The residue (56.7 g, 344 mmol) was dissolved in trimethylorthoformate (100 mL) and treated with benzaldehyde (34.9 mL, 36.4 g, 344 mmol). After stirring for 2 h, the reaction was diluted with Et$_2$O (200 mL) and washed with water (3×50 mL). The organic solution was dried over MgSO$_4$, filtered, and concentrated. A portion of the imine residue (26.8 g, 100 mmol) was dissolved in dichloromethane (240 mL) and treated with 160 mL of 10N NaOH, methallyl dichloride (50.0 g, 400 mmol), and Bu$_4$NHSO$_4$ (3.59 g). After stirring for 10 h at rt, the reaction was diluted with dichloromethane and the organic solution separated, dried over MgSO$_4$, filtered, and concentrated. The residue was redissolved in Et$_2$O/1N HCl (200 mL/200 mL) and stirred for 2 h. The aqueous phase was separated and neutralized with iON NaOH (to pH 8). The aqueous mixture was extracted with EtOAc (3×200 mL). The combined organic solutions were dried over MgSO$_4$, filtered and concentrated. The residue was dissolved in water and neutralized (to pH 8). Extraction of this mixture with EtOAc (X 3) followed by drying over MgSO$_4$, filtratration, and concentration provided crude 1B-2. Purification of this residue by flash chromatography (SiO$_2$; 30% EtOAc/hexanes) provided pure 1B-2.

Data for 1B-2: $^1$HNMR (500 MHz, CDCl$_3$) δ 7.51 (m, 2H), 7.42 (m, 3H), 5.03 (s, 1H), 4.95 (s, 1H), 3.71 (m, 5H), 3.41 (m, 1H), 2.80 (m, 1H) ppm.

Step 2: 7a-Phenyldihydro-1H-pyrrolo[1,2-c][1,3]oxazole-3,6(5H)-dione (1-6)

A suspension of LiAlH$_4$ (7.14 g, 188 mmol) in TBF (500 mL) was cooled to 0° C. and treated with a solution of ester 1B-2 (10.2 g, 47 mmol) in THF (50 mL) over 20 min. After stirring for 30 min at 0° C., the reaction was cautiously quenched by the addition of water (7.1 mL), 15% aq NaOH (7.1 mL), and H$_2$O (21.3 mL). Solid Na$_2$SO$_4$ was added and the rmixture stirred for 40 min. The mixture was filtered and concentrated. The residue (8.2 g, 43.3 mmol) was dissolved in dichloromethane (300 mL) and treated with triethylamine (9.0 mL, 6.5 g, 65.0 mmol) and carbonyldiimidazole (9.14 g, 56.4 mmol). After stirring for 48 h at rt, the reaction was diluted with dichloromethane and washed with 1N HCl and brine. The organic solution was concentrated and not further purified. A solution of the residue 1B-3 (9.2 g, 42.8 mmol) in dichloromethane (200 mL) was cooled to −78° C. and ozone was passed through the solution until a blue color persisted. The solution was purged and treated with dimethylsulfide (35 mL). After gradual warming to rt overnight, the solution was concentrated to a yellow solid. Trituration of this solid with Et$_2$O provided pure 1-6. Data for 1-6: $^1$HNMR (500 MHz, CDCl$_3$) δ 7.5-7.3 (m, 5H), 4.7 (d, 1H), 4.3 (d, 1H), 4.2 (d, 1H), 3.5 (d, 1H), 3.1 (d, 1H), 2.95 (d, 1H), 2.9 (d, 1H) ppm.

SCHEME 1C

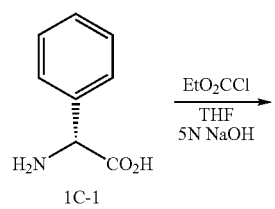

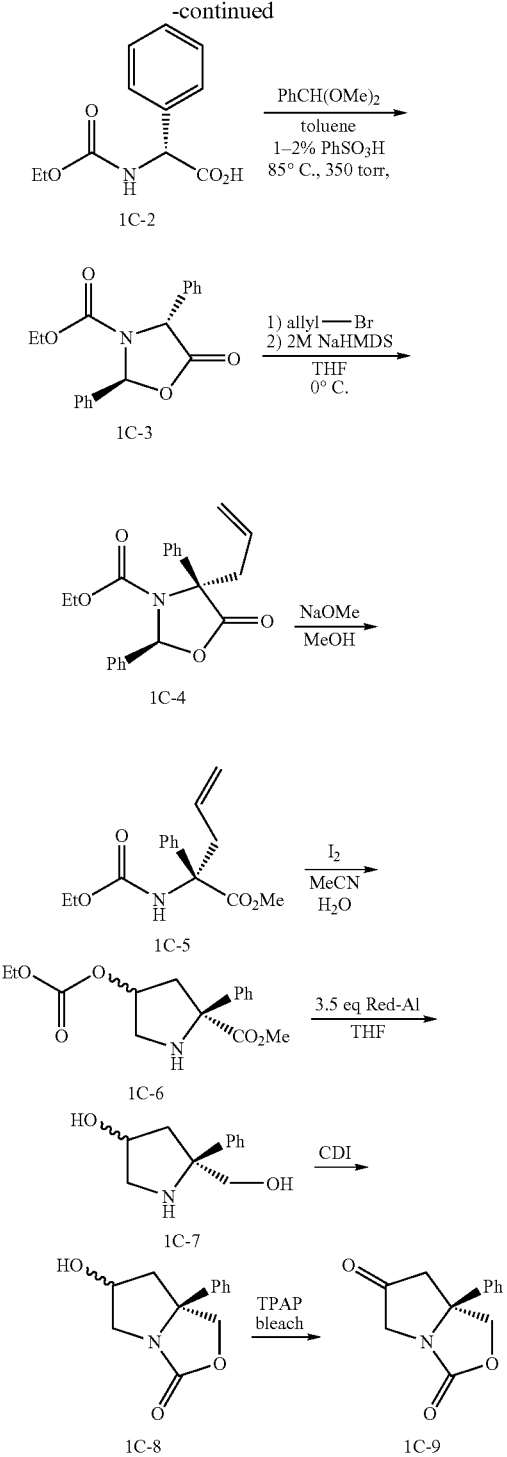

Step 1: (2R)-[(ethoxycarbonyl)amino](phenyl)acetic acid (1C-2)

To a 0 ° C. mixture of (R)-(−)-2-phenylglycine (IC-1, 4 kg) in THF and 5N NaOH (10.6 L) was added ethyl chloroformate over 1 h with the internal temperature maintained below 10 ° C. Upon completion of the addition, the reaction was aged for 15 min at 0-10 ° C. and assayed for completion. The reaction was quenched with 37% HCl (until pH =1, 2.3 L) with the internal temperature maintained <25° C. Toluene (20

L) was added and after agitation/settling, the aqueous layer was cut. The organic layer was assayed for yield and solvent switched to toluene. The slurry of 1C-2 was used directly in the next reaction. (2R)-[(ethoxycarbonyl)amino]-(phenyl)acetic acid: mp 154-156 °C.; $^1$H NMR (CDCl$_3$, 400 MHz) indicated a ~1.1:1 mixture of rotamers: δ=12.12 (bs, 2H), 7.99 (d, J=5.3 hz, 1H), 7.45-7.32 (m, 10H), 5.78 (d, J=6.2 Hz, 1H), 5.41 (d, J=7.1 Hz, 1H), 5.25 (d, J=5.7 Hz, 1H), 4.12 (m, 2H), 4.05 (mn, 2H), 1.24 (t, J=6.9 Hz, 3H), 1.06 (t, J=7.0 Hz, 3H); $^{13}$C NMR (CDCl$_3$, 100 MHz): δ =175.1, 173.6, 157.3, 155.8, 137.4, 136.1, 129.0, 128.7, 128.6, 128.2, 127.2, 127.1, 62.1, 61.5, 58.3, 57.7, 14.4, 14.1; MS m/z 224 ([M+H]$^+$, C$_{11}$H$_{14}$NO$_4$, calc'd 224.09).

Step 2: ethyl (2S,4R)-5-oxo-2,4-diphenyl-1,3-oxazolidine-3-carboxylate (1C-3)

To an 85 °C. solution of 1C-2 and PhSO$_3$H (42.7 gm) in toluene under reduced pressure (350 torr), was added a solution of benzaldehyde dimethyl acetal(3 L) in toluene (5 mL/g) over 1-2 H. Toluene/MeOH was distilled off through the course of reaction. Upon completion of the reaction, the solution was cooled to rt and diluted with THF (36 L), until homogeneous. The organic solution was washed with 10% NaHSO$_3$ (7.5 L), followed by sat'd. NaHCO$_3$ (9 L). The solvent was then switched to toluene and diluted to 7.5 mL/g total volume (vs. assay yield) with toluene upon completion. The slurry was heated to 75 °C. and aged until homogeneous. Upon slow cooling, 1C-3 crystallized. When the slurry reached 40 °C., heptane (2.5 mL/g) was added. The slurry was cooled to rt and filtered to collect the solid. The solid was washed with 1:1 toluene/heptane (5 mL/g) and dried to a constant weight under a nitrogen stream. ethyl (2S,4R)-5-oxo-2,4-diphenyl-1,3-oxazolidine-3-carboxylate: mp 197-199 °C.; $^1$H NMR (CDCl$_3$, 400 Hz) δ=7.46-7.37 (m, 10H), 6.77 (bs, 1H), 5.45 (bs, 1H), 3.96 (m, 2H), 3.86 (m, 2H), 0.84 (t, J=7.1 Hz, 3H); $^{13}$C NMR (CDCl$_3$, 100 MHz): δ=130.2, 129.1, 129.0, 218.8, 126.7, 90.3, 61.9, 60.3, 13.8; MS m/z 312 ([M+H]$^+$, C$_{18}$H$_{18}$NO$_4$, calc'd 312.12).

Step 3: ethyl (2S,4S)-4-allyl-5-oxo-2,4-diphenyl-1,3-oxazolidine-3-carboxylate (1C-4)

To an –10 °C. solution of 1C-3 and allyl-Br(1.67 L) in THF (40 L) was added a 2M solution of sodium bis(trimethylsilyl)amide in THF (7 L) over 1 h, with the temperature maintained <5° C. After 5 min, the reaction was assayed for completion. The reaction was quenched with 1N HCl (22.5 L) and diluted with heptane (20 L). The Aq. layer was cut and the organic layer was washed with sat'd. brine (12 L). The solvent was switched to MeOH and water was removed azeotropically until a KF <900 ppm was achieved. The solution of 1C-4 was used directly in the next reaction. ethyl (2S,4S)-4-allyl-5-oxo-2,4-diphenyl-1,3-oxazolidine-3-carboxylate: $^1$H NMR (CDCl$_3$, 400 Hz) δ =7.60-7.52 (m, 2H), 7.39-7.33 (m, 8H), 6.55 (m, 1H), 5.84 (m, 1H), 5.38 (m, 2H), 4.16 (m, 2H), 3.72-3.12 (m, 2H), 1.17 (t, J=7.0 Hz, 3H); $^{13}$C NMR (CDCl$_3$, 100 MHz): δ=172.5, 164.0, 137.5, 131.0, 130.5, 129.7, 128.3, 128.1, 127.4, 126.2, 122.0, 89.5, 62.0, 42.2, 40.4, 14.2; MS m/z 352 ([M +H]$^+$, C$_{21}$H$_{22}$NO$_4$, calc'd 352.15).

Step 4: methyl (2S)-2-[(ethoxycarbonyl)amino]-2-phenyl-pent-4-enoate (IC-5)

To an 23 °C. solution of 1C4 in MeOH (20 L) was added 30% NaOMe in MeOH (535 mL) over 0.25 h, with the temperature maintained <30° C. After 4 h, the reaction was assayed for completion. The reaction was quenched into 5% NaHSO$_3$ (40 L) and diluted with IPAc (20 L). The aqueous layer was cut and the organic layer was washed with 10% KH$_2$PO$_4$ (12 L). The solvent was switched to MeCN and used directly in the next reaction. methyl (2S)-2-[(ethoxycarbonyl)amino]-2-phenylpent-4-enoate: $^1$H NMR (CDCl$_3$, 400 Hz) δ=7.46-7.43 (m, 2H), 7.39-7.27 (m, 3H), 6.23 (bs, 1H), 5.76-5.66 (m, 1H), 5.20-5.14 (m, 2H), 4.10-4.00 (m, 2H), 3.68 (s, 3H), 3.53 (bs, 1H), 3.20 (dd, J=13.7, 7.6 Hz, 1H) 1.27-1.15 (m, 3H); $^{13}$C NMR (CDCl$_3$, 100 MHz): δ =172.6, 154.3, 139.8, 132.3, 128.4, 127.8, 125.9, 119.4, 65.0, 60.6, 53.1, 37.8, 14.4; MS m/z 300 ([M+Na]$^+$, C$_{15}$H$_{19}$NNaO$_4$, calc'd 300.12).

Step 5: methyl 4-[(ethoxycarbonyl)oxy]-2-phenyl-D-prolinate (1C-6)

To an 23° C. solution of 1C-5 in MeCN (42 L) was added water (12 L), followed by I$_2$ (8 kg). After 6 h, the reaction was assayed for completion. The reaction was quenched with 10% Na$_2$SO$_3$ (35 L), basified with 50wt % NaOH (4 L) and extracted with IPAc (35 L). The aqueous layer was cut and discarded and the organic layer was extracted with 6N HCl (35 L). The organic layer was discarded. The aq. layer was cooled to –10° C., IPAc (35 L) was added, and slowly neutralized with 22 L of 10N NaOH. The aqueous layer was cut and discarded and the solution of 1C-6 was stored. methyl 4-[(ethoxycarbonyl)oxy]-2-phenyl-D-prolinate: $^1$H NMR (CDCl$_3$, 400 Hz) indicated a 2:1 mixture of diastereomers: δ=7.55-7.47 (m, 5H), 7.34-7.22 (m, 5H), 5.18-5.11 (m, 2H), 4.22-4.11 (m, 4H), 3.68 (s, 6H), 3.33-3.24 (m, 4H), 3.10 (d, J=14.1 Hz, 2H), 3.05 (b, 2H), 2.34 (dd J=14.3, 5.5 Hz, 1H), 2.22 (dd J=14.3, 4.1 Hz, 1H), 1.31-1.23 (m, 6H); $^{13}$C NMR (CDCl$_3$, 100 MHz): δ=175.2, 175.1, 154.7, 154.4, 142.0, 141.5, 128.3, 128.2, 127.5, 127.4, 126.0, 125.7, 78.5, 77.6, 71.7, 71.0, 63.8, 52.9, 52.8, 52.7, 52.0, 51.8, 43.2, 42.9, 14.1, 14.0; MS m/z 294 ([M+H]$^+$, C$_{15}$H$_{20}$NO$_5$, calc'd 294.13).

Step 6: (5S)-5-(hydroxymethyl)-5-phenylpyrrolidin-3-ol (1C-7)

To a solution of carbonate 1C-6 (5.0 g, 17.0 mmol) in THF (50 mL) was added Red-Al 3.5M solution in toluene (17.0 mL, 59.7 mmol, 3.5 moleq.) at –50° C. The reaction mixture was warmed up to rt and aged for 2 h. The reaction was quenched by 2.0M Rochelle salt solution (45 mL, ca. 1.5 moleq to Red-Al) at 0° and aged vigorously over 5h at rt. After the aqueous phase was separated, the mixed organic solution was switched to n-BuOAc by azeotropic distillation under reduced pressure (ca. 20 torr, 60° C.). After 200 mL of n-BuOAc was added, THF, toluene and methoxy ethanol were detected less than 0.1% in GC and KF showed 0.11%. MS m/z 194 ([M+H]$^+$, C11H15NO2, calc'd 193.11).

Step 7: (7aS)-6-hydroxy-7a-phenyltetrahydro-1H-pyrrolo[1,2-c][1.3]oxazol-3-one (1C-8)

To the n-BuOAc solution described in Step 6 was added CDI (3.46 g, 21.3 mmol, 1.25 moleq.) portionwise and aging for 1 h at rt. 30 mL of 2N HCl solution was added to the reaction mixture and aging for 1 h. The aqueous phase was separated and extracted with 30 mL of n-BuOAc after addition of 6.0 g of NaCl. To the combined organic layer was added 150 mg of activated carbon (Darco KB) and the mixture aged overnight. The carbon was filtered through a pad of Solka-Floc. Data: $^1$H-NMR (400MHz, CDCl$_3$) δ 7.47-7.28 (m, 7H), 4.65 (d, J=8.3 Hz, 1H), 4.644.59 (m, 0.4H), 4.574.51 (m, 1H), 4.51 (d, J=8.8 Hz, 0.4H), 4.33 (d, J=8.3 Hz, 1H), 4.28 (dd, J=13.1, 6.7 Hz, 0.4H), 4.15 (d, J=8.8 Hz, 0.4H), 3.92 (d, J=12.7 Hz, 1H), 3.28 (dd, J=12.7, 3.9 Hz, 1H), 3.18 (dd, J=13.1, 2.7 Hz, 0.4H), 2.63 (d, J=13.6 Hz, 0.4H), 2.50 (dd, J=13.7, 5.1 Hz, 1H), 2.40 (brd, J=13.7 Hz, 1H), 2.25 (dd, J=13.6, 6.8 Hz, 0.4H).

Step 8: (7aS)-7a-phenyldihydro-1H-pyrrolo[1,2-c][1,3]oxazole-3,6(5H)-dione (1 C-9)

IC-8 (crude, a portion of above solution 1.40 g assay, 6.38 mmol) in n-BuOAc was concentrated under reduced pressure and 14 mL of MeCN was added to the crude crystals. The solvent ratio was n-BuOAc : MeCN=8:92 in GC. To this solution was added AcOH (1.10 mL, 19.2 mmol, 3.0 moleq.), TPAP (33.6 mg, 0.095 mmol, 1.5mol %) and 2.0M solution of NaOCl (9.5 mL, 19.2 mmol, 3.0 moleq.) dropwise over 30 min at rt. (ca. 5% of chlorinated product was seen in HPLC.) After 30 min, the reaction mixture was diluted with 12 mL of AcOEt and the aqueous phase was separated. The organic phase was washed with sat. $Na_2S_2O_3$ aq. and brine. The organic solvent was switched to MTBE and the resulted precipitate was filtered and washed with MTBE. Obtained ketone lC-9; 78% (1.08 g, 4.97 mmol, 99.4area%, 97.0 w/w %, 0.5area % of chlorinated product).

Scheme 1D (2S)-2-({[tert-Butyl(dimethyl)silyl]oxy}methyl)-4-(2,5-difluorophenyl)-2-phenyl-2,5-dihydro-1H-pyrrole-1-carbonyl chloride 1-9

In a flask equipped with overhead stirrer, thermocouple, and nitrogen/vacuum inlet was charged the S-TBS pyrroline solid 1-8 (180 gms) and IPAC added (1.26 L). Stirring was continued until the solution became homogeneous, about 30 minutes.

In a separate flask equipped with overhead stirrer, thermocouple, and nitrogen/vacuum inlet IPAC added (1.26 L) and the solution cooled to −5° C. Triphosgene was added (67 gms) and then lutidine (173 ml) slowly added. The solution of the S-TBS pyrroline was then added to this solution slowly. The reaction was monitored by HPLC and was considered complete when the conversion of the amine to the product is >99A % at 200 nm by HPLC. The reaction was quenched by adding 1.8 L of 10 wt % aq. citric acid to the reaction mixture. The layers were separated and the organic layer washed twice with water (240 mL). The organic layer was then concentrated to 900 ml (water content was 105 ug/ml) and used directly in the coupling reactions. HPLC assay showed 99.96% conversion to the carbamyl chloride.

Scheme 1E 2-({[tert-Butyl(dimethyl)silyl]oxy}methyl)-4-(2,5-difluorophenyl)-2-phenyl-2,5dihydro-1H-pyrrole (1-8)

Step 1: 6-(2.5-Difluorophenyl)-7a-phenyl-5,7a-dihydro-1H-pyrrolo[1,2-c][1,3]oxazol-3-one (1-7)

A suspension of 231 g (1.06 moles) of 1-6 in 11 L of THF in a 20 L jacketed reactor was stirred vigorously with overhead stirring for 1 h, then cooled to −70° C. To this suspension was added dropwise 1.28 L (1.28 moles) of a 1M solution of NaHMDS in THF. After stirring for 3 h, 478.9 g (1.28 moles) of solid N-phenylbis(trifluoro-methanesulphonimide) was added, followed by an additional 1.5 h of stirring, before being quenched by the addition of 2 L of a saturated aqueous $NH_4Cl$ solution. After the solution reached room temperature, 2 L of water and 2 L of EtOAc were added, the layers were separated, and the aqueous layer was extracted with 2 L of EtOAc. The combined organic layers were washed with brine, dried over $Na_2SO_4$, and concentrated by rotary evaporation. The residue was dissolved in 6 L of DME and 1.2 L of water in a 20 L jacketed reactor with overhead stirring, and the solution was degassed with a strong flow of $N_2$ for 1 h. To the reactor was then added 201.6 g (1.28 moles) of 2,5-difluorophenylboronic acid, 134 g (3.19 moles) of LiCl, 338 g (3.19 moles) of $Na_2CO_3$, and 24.6 g (21 mmol) of tetrakis (triphenylphospine)palladium(O), and the reaction was heated at 90° C. for 2 h. Following this period of time, approximately 4.5 L of DME was distilled off, the remaining solution was cooled to room temperature, and dumped into 6 L of water and 8 L of $CH_2Cl_2$. The layers were separated, the aqueous layer was extracted with 2 L of $CH_2Cl_2$, the organic layers were combined, washed with 4 L of water, dried over $Na_2SO_4$ and concentrated by rotary evaporation to provide a dark red solid mass. This residue was swished with 500 mL of $CHCl_3$, and filtered to provide a tan solid. The filtrate was concentrated to ~300 mL and a second crop of solid was collected, combined with the first crop, and the combined material was swished with 500 mL of EtOAc overnight. This suspension was filtered to provide an off-white solid, the filtrate was concentrated to ~250 mL and a second crop was collected, combined with the first crop, and the combined material (~205 g) was recrystallized from 1.6 L of EtOAc to provide 1-7 as a white solid. Data for 1-7: $^1$HNMR (500 MHz, $CDCl_3$) δ 7.5-7.3 (mn, 5H), 7.1-6.9 (m, 3H), 6.8 (s, 1H), 4.9 (d, 1H), 4.75 (d, 1H), 4.5 (d, 1H), 4.25 (d, 1H) ppm. HRMS (ES) calc'd M+H for $C_{18}H_{13}F_2NO_2$: 314.0987. Found: 314.0993.

Step 2: 2-({[tert-Butyl(dimethyl)silyl]oxy}methyl)-4-(2,5-difluorophenyl)-2-phenyl-2,5-dihydro-1H-pyrrole (1-8)

A suspension of 109.4 g (349 mmol) 1-7 in 2.2 L of EtOH and 105 mL (1.05 moles) of 10 M NaOH in a 10 L round bottom was heated at 60° C. for 4 h, cooled to room temperature and aged overnight. To this mixture was added 90.2 mL (1.08 moles) of concentrated HCl and the solvents were removed by rotary evaporation. The residue was suspended in 2 L of acetonitrile and again taken to dryness by rotary evaporation. The solids were suspended in 3.8 L of $CH_2Cl_2$ and 200 mL of DMF, 118.7 g (1.75 moles) of imidazole was added, followed by 110.5 (733 mmol) of TBSCl. After stirring for 15 h under a gentle stream of $N_2$, the reaction was dumped into 4 L of water and 2 L of $CH_2Cl_2$, the layers were separated, and the aqueous layer was extracted with 2 L of $CH_2Cl_2$. The combined organic extracts were then washed with 4×4 L of water, dried over $Na_2SO_4$, and concentrated by rotary evaporation. The residue was dissolved in 500 mL of MeOH and 500 mL of 2M $MeNH_2$ in MeOH, stirred for 4 h, and then concentrated by rotary evaporation. The residue was placed under high vacuum until a constant weight was obtained, and the material was crushed with a mortar and pestle to provide 1-8 as a beige solid. Data for 1-8: $^1$HNMR (500 MHz, $CDCl_3$) δ 7.6-7.3 (m, 5H), 7.1-6.9 (m, 3H), 6.75 (s, 1H), 4.25 (d, 1H), 4.1 (d, 1H), 3.95 (d, 1H), 3.75 (d, 1H), 0.9 (s, 9H), 0.1 (s, 3H), 0.05 (s, 3H) ppm.

SCHEME 2

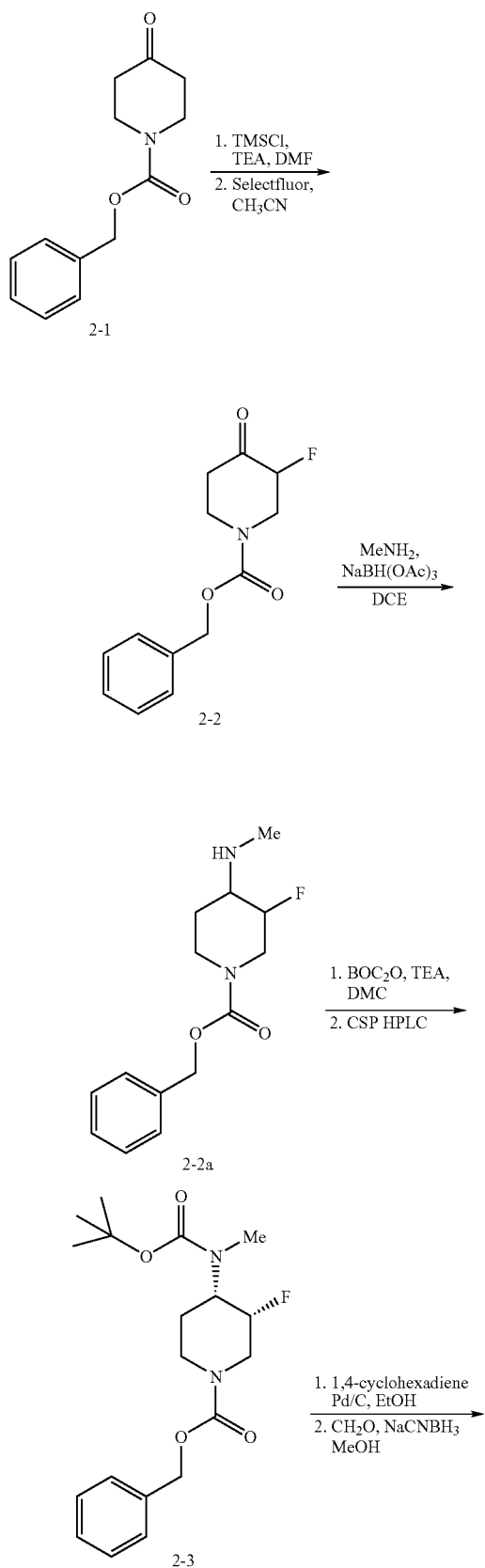

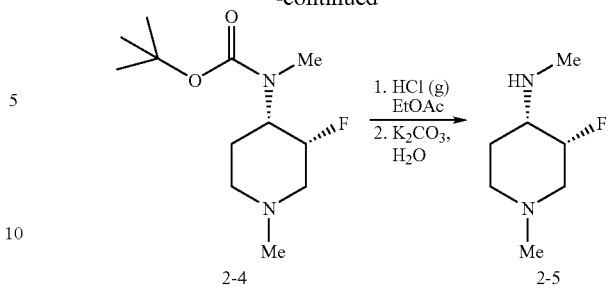

Step 1: Benzyl 3-fluoro-4-oxopiperidine-1-carboxylate (2-2)

To a solution of 10.0 g (43 mmol) of benzyl-4-oxo-1-piperidinecarboxylate in 25 mL of DMF was added 14.3 mL (103 mmol) of triethylamine and then 6.53 mL (52 mmol) of TMSCl. The reaction was heated at 80° C. overnight, cooled to room temperature, and then dumped into hexanes in a separatory funnel. The mixture was partitioned with saturated aqueous $NaHCO_3$, separated, washed with brine, dried over $MgSO_4$ and concentrated by rotary evaporation. The residue was dissolved in 500 mL of $CH_3CN$ and treated with 16.7 g (47 mmol) of Selectfluor. After 90 min the reaction was concentrated to about half the original volume, partitioned between EtOAc and brine, separated, dried over $MgSO_4$, filtered, and concentrated by rotary evaporation. The residue was loaded onto a silica gel column and eluted with EtOAc/hexanes to provide 2-2 as a colorless oil.

Step 2: Benzyl 3-fluoro4-(methylamino)piperidine-1-carboxylate (2-2a)

To a solution of 9.4 g (37.5 mmol) of 2-2 in 150 mL of 1,2-dichloroethane was added 37.5 mL (74.9 mmol) of a 2M solution of methylamine in THF and 11.9 g (56.2 mmol) of $Na(OAc)_3BH$. After stirring for 2 h, the reaction was quenched with saturated aqueous $K_2CO_3$, partitioned with EtOAc, separated, and the aqueous phase extracted 3×EtOAc. The combined organic extracts were washed with brine, dried over $MgSO_4$, filtered, and concentrated by rotary evaporation. The residue was loaded onto a silica gel column and eluted with 80:10:10 $CHCl_3$/EtOAc/MeOH to provide both the cis and trans isomers of 2-2a as colorless oils. Data for the trans isomer of 2-2a, first to elute (confirmed by NOE analysis): $^1HNMR$ (600 MHz, $CD_2Cl_2$) δ 7.4-7.3 (m, 5H), 5.1 (m, 2H), 4.4-4.1 (m, 2H), 3.9 (m, 1H), 3.15-3.05 (m, 2H), 2.75 (m, 1H), 2.4 (s, 3H), 2.0 (in, 1H), 1.25 (m, 1H) ppm. Data for the cis isomer of 2-2a, second to elute (confirmed by NOE analysis): $^1HNMR$ (600 MHz, $CD_2Cl_2$) δ 7.4-7.2 (m, 5H), 5.1 (m, 2H), 4.9-4.7 (m 1H), 4.4 (m, 1H), 4.15 (m, 1H), 3.1-2.9 (m, 2H), 2.6 (m, 1H), 2.4 (s, 3H), 1.8 (m, 1H), 1.6 (m, 1H) ppm. HRMS (ES) calc'd M+H for $C_{14}H_{19}F_1N_2O_2$: 267.1504. Found: 267.1500.

Step 3: Benzyl (3R,4S)-4-[(tert-butoxycarbonyl)(methyl)amino]-3-fluoropiperidine-1-carboxylate (2-3)

To a solution of 7.67 g (28.8 mmol) of cis-2-2a in 150 mL of $CH_2Cl_2$ was added 12.1 mL (86.5 mmol) of triethylamine and 9.44 g (43.3 mmol) of di-tert-butyl dicarbonate. After stirring for 1 h, the reaction was partitioned between $CH_2Cl_2$ and H$_2$O, the organic phase was washed with brine, dried over MgSO$_4$, filtered and concentrated by rotary evaporation. The residue was loaded onto a silica gel column and eluted with EtOAc/hexanes to provide racemic cis-2-3 as a white solid. Resolution of the enantiomers was carried out chromatographically using a Chiralpak AD© 10×50 cm column with 20% isopropanol in hexanes (with 0.1% diethylamine) at 150 mL/min. Analytical HPLC analysis of the eluent on a 4×250 mM Chiralpak AD® column with 20% isopropanol in hexanes (with 0.1% diethylamine) at 1 mL/min indicated that first eluting enantiomer (enantiomer of 2-3) has $R_t$=5.90 min and the second enantiomer (2-3) has $R_t$=6.74 min. Data for 2-3: HRMS (ES) calc'd M+Na for $C_{19}H_{27}F_1N_2O_4$: 389.1847. Found: 389.1852.

Step 4: tert-Butyl [(3R,4S)-3-fluoro-1-methylpiperidin-4-yl] methylcarbamate (24)

To a solution of 4.6 g (12.6 mmol) of the second eluting enantiomer 2-3 in 150 mL of EtOH was added 29.7 mL (314 mmol) of 1,4-cyclohexadiene and a catalytic amount of 10% Pd on carbon. After stirring overnight, the reaction was filtered through Celite, and concentrated by rotary evaporation. The residue was dissolved in 75 mL of MeOH, 2 mL of AcOH and 3.1 mL (38 mmol) of 37% aqueous formaldehyde were added, and the mixture was stirred for 1 h. At that time, 1.58 g (25.1 mmol) of NaCNBH$_3$ in 10 mL of MeOH was added and the reaction was aged for 2 h more before being dumped into saturated aqueous NaHCO$_3$. After extracting with 3×CH$_2$Cl$_2$, the organic phase was washed with water, dried over MgSO$_4$, filtered, and concentrated by rotary evaporation to provide 2-4 as a colorless oil. Data for 2-4: HRMS (ES) calc'd M+H for $C_{12}H_{23}FN_2O_2$: 247.1817. Found: 247.1810.

Step 5: (3R,4S)-3-Fluoro-N,1-dimethylpiperidin-4-amine (2-5)

To a solution of 3.0 g (12.2 mmol) of 2-4 in 100 mL of EtOAc was bubbled HCl gas until the solution was warm to the touch. The flask was then capped and stirred for 4 h. The volatiles were removed by rotary evaporation, and the residue was triturated with Et$_2$O and placed under high vacuum to provide a white solid. This material was mixed with 25 mL of 15% aqueous Na$_2$CO$_3$ and extracted with 5×50 mL 2:1 CHCl$_3$/EtOH. The organic was concentrated by rotary evaporation with very mild heating, the residue was dissolved in 200 mL of CHCl$_3$, dried over Na$_2$SO$_4$, and concentrated to provide 2-5 as a colorless oil. Data for 2-5: $^1$HNMR (500 MHz, CDCl$_3$) δ 4.8 (m, 1H), 3.15 (m, 1H), 2.85 (m, 1H), 2.5 (s, 3H), 2.45 (m, 1H), 2.3 (s, 3H), 2.2-2.0 (m, 2H), 1.9-1.7 (m, 2H) ppm. HRMS (ES) calc'd M+H for $C_7H_{15}FN_2$: 147.1292. Found: 147.1300.

Scheme 2A

Step 1: Benzyl 3-fluoro-4-oxopiperidine-1-carboxylate (2-2)

A 22-L round bottom flask with mechanical stirrer was charged with Cbz-ketone 2-1 (2.5 kg, 10.7 mol), 5.0 L of dimethylacetamide, triethylamine (3.0L, 21.5 mol). Trimethylsilylchloride (2.0 L, 15.7 mol) was added. The mixture heated to 60° C. and aged for 4 hours. After cooling to 10° C., the mixture was quenched into 10 L of 5% sodium bicarbonate and 10 L n-heptane maintaining the internal temperature at less than 20° C. The organic layer was washed twice with 10 L of 2.5% sodium bicarbonate. The final organic layer was dried over sodium sulfate, filtered, and concentrated under reduced pressure and solvent switched to 10 L MeCN.

A 50-L jacketed vessel was charged with 7.5 L of MeCN and Selectfluor (4.1 kg, 11.5 mol). The slurry was cooled to 10° C. and potassium carbonate (0.37 kg, 2.68 mol) added. The silyl ether solution in MeCN was transferred in portions maintaining the internal temperature at 10-15° C. The final slurry was aged for 2 hours at 10-15° C. The reaction was quenched into a 100 L extractor containing 20 L of 2 N hydrochloric acid and 30 L of ethyl acetate. The organic layer was washed with 20 L of 2 N hydrochloric acid, 10 L of 20 wt % sodium chloride, dried over sodium sulfate, and filtered. The filtrate was concentrated and flushed with dry EtOAc under reduced pressure to KF=16000 µg/mL and then solvent switched under reduced pressure to ~10 L THF.

Step 2: Benzyl 3-fluoro-4-(methylamino)piperidine-1-carboxylate (2-2a)

In a round-bottom flask, Cbz fluoroketone (10.3 mol) was dissolved in tetrahydrofuran (30 L). Methylamine, 2 M in tetrahydrofuran (2.00 equiv; 20.6 moles; 10.3 L) was added and the mixture stirred for 30 min at room temp. The mixture was cooled to 0° C. and acetic acid (20.6 moles; 1.17 L; 1.236 kg) added followed by stirring at 0° C. for another 30 minutes. Sodium triacetoxyborohydride (12.36 moles; 2.62 kg) was added in portions to the solution in 15 minutes and the reaction mixture was aged at 0° C. until completion as judged by HPLC analysis.

The reaction mixture was transferred slowly into a 100 L cylindrical extractor containing hydrochloric acid, 12 M in water (30.9 moles, 2.575 L), water (30 L), and toluene (140 mol, 15 L). After vigorous stirring for 15 minutes, the layers were separated and toluene layer further washed with water (10 L). The combined aqueous layer was transferred back into the extractor. Sodium hydroxide, 10 M in water (82.4 mole, 8.24 L), was added and the mixture extracted once with IPAC (30 L).

The organic layer was dried with sodium sulfate (3 kg) and concentrated. The residue was dissolved in 8:2 (vol:vol) ethanol:water (23 kg ethanol mixed with 7.2 kg water), 85% phosphoric acid (9.83 mol, 952 g, 667 mL) was added to the solution and crystal seeds were added. The mixture was stirred at room temperature overnight. Crystalline solid precipitated and was collected by filtration. The solid was washed with 8:2 ethanol:water and dried in vacuum oven to give 2.1 kg solid.

The solid was suspended in 36 L EtOH and 4 L water mixture and the mixture was heated to 70° C.-80° C. until all solid dissolved. The heat source was removed and the clear solution was seeded with the cis isomer mixture 2-2a. After stirring at room temperature overnight, a crystalline solid precipitated and was collected by filtration. The solid product was dried in vacuum oven to give white solid.

Step 3: Benzyl (3R,4S)-4-[(tert-butoxycarbonyl)(methyl)amino]-3-fluoropiperidine-1-carboxylate 2-3

In a 50 L extractor was charged 20 L water and 1.06 kg Na$_2$CO$_3$, the mixture was stirred until all solid was dissolved. IPAC (20 L) and CBZ amine carboxylate (1.85 kg, 5.3 mol) were added. The layers were cut after mixing. The aqueous layer was extracted with another 5 L EPAC. The combined organic layers were dried with sodium sulfate. After the drying agent was filtered off, the batch was charged into a 72 L round bottom flask, and Boc$_2$O solution (1.0 M, 4.8 L) was added. HPLC assay after 45 min indicated 98% conversion. Additional Boc$_2$O solution (50 mL) was added. After the batch was aged for additional 15 hours, it was concentrated under vacuum to the minimum volume, flushed with MeOH (10 L-15 L). The batch was diluted with methanol to a total weight of ca. 14.3 kg. HPLC assay indicated ca. 1.9 kg desired product.

The fluoropiperidine was resolved by chromatographic separation on 20 rmicron Chiralpak AD (Diacel Chemical Industries, Ltd.) chiral stationary phase column (30 ID×25 cm). An amount of 54 g of racemate per injection was eluted with methanol. The lowest retention time enantiomer was collected giving 45 g (85% recovery) of the desired (3R, 4S) enantiomer in 98% ee. This separation process was repeated and the desired fractions from different injections were combined and concentrated.

Step 4: tert-Butyl f(3R,4S)-3-fluoro-1-methylpiperidin-4-yl]methylcarbamate (24)

The concentrated solution (4 L) from the chiral separation step was shown to contain 489.5 g (1.3 mol) of Cbz-Boc-diamine 2-3. To this solution, formaldehyde (37% in water, 430 mL, 5.3 mol) was added and the mixture pressurized under hydrogen over 5% Pd/C (183 g) for 4 hours. The reaction mixture was filtered to remove the catalyst and partitioned between 8 L of EtOAc and 8 L of 0.5 M sodium bicarbonate. The organic layer was washed with 8 L of 0.5 M sodium bicarbonate. The combined aqueous layers were back extracted with 8 L of EtOAc. The combined organic layers were dried over sodium sulfate and filtered. The filtrate was used in the next step directly.

Step 6: (3R,4S)-3-Fluoro-N,1-dimethylpiperidin-4-amine (2-5)

The ethyl acetate solution containing the Boc protected diamine 2-4 (327 g by HPLC assay) was charged to a 12 L flask while concentrating at 28° C. When the batch had a total volume of 1.5 L, the batch was then solvent switched to ethanol by charging 8 L of ethanol while distilling at a constant volume.

To a different 12 L round bottom flask was added 1.5 L of ethanol (200 proof, punctilious). 436 mL of acetyl chloride was then added to the ethanol maintaining the temperature below 35° C. with the aid of a water bath. The solution was stirred for 1h. The ethanol solution containing 302 g of the Boc protected diamine 2-4 was then slowly added to the HCl, maintaining temp <30° C. At the point where ¾ of the addition was complete, solids began to crystallize from the solution. The reaction was monitored by GC and the slurry stirred overnight. The solids were isolated by filtration and cake washed with 2 L of 85% ethanol, 15% ethyl acetate. The filter cake was then dried under vacuum with a stream of $N_2$ overnight to yield 243 g of the desired product 2-5 as the bis hydrochloride salt. GC analysis indicated the batch to be 99.3% ee.

Approximately 200 mg of 2-5 (fluoropiperidine 2 HCl) was added to a vial and suspended in methanol (<500 µL). The sample was heated to dissolution with a heat gun. After 2 hours large 3 dimensional crystals were noted. Crystals were isolated by removal of the remaining solvent.

A single crystal was selected for single crystal x-ray data collection on a Bruker Smart Apex system. The crystal was colorless plate with dimensions of 0.24 mM×0.22 mM×0.14 mM. The unit cell was collected on 5 second scan rate and auto indexing gave the cell setting to be monoclinic. The structure was solved in the monoclinic P $2_1$ space group after a quadrant data collection using 5 second scan rate. See Tables 1-5 for tabulated information pertaining to the final specifications of the solved structure. A computer drawing of the structure of 2-5 is shown in FIG. 1.

TABLE 1

Crystal data and structure refinement for 2-5.

| | |
|---|---|
| Empirical formula | $C_8 H_{21} C_{12} F N_2 O$ |
| Formula weight | 251.17 |
| Temperature | 298(2) K |
| Wavelength | 0.71073 Å |
| Crystal system, space group | Monoclinic, P2(1) |
| Unit cell dimensions: | a = 7.286(2) Å alpha = 90 deg. |
| | b = 7.637(2) Å beta = 105.295(5) deg. |
| | c = 12.378(4) Å gamma = 90 deg. |
| Volume | 664.3(4) Å$^3$ |
| Z, Calculated density | 2, 1.256 Mg/m$^3$ |
| Absorption coefficient | 0.477 mm$^{-1}$ |
| F(000) | 268 |
| Crystal size | 0.24 × 0.22 × 0.14 mm |
| Theta range for data collection | 1.71 to 26.35 deg. |
| Limiting indices | −9 <= h <= 9, −9 <= k <= 9, −15 <= 1 <= 15 |
| Reflections collected/unique | 5309/2674 [R(int) = 0.0227] |
| Completeness to theta = 26.35 | 99.7% |
| Absorption correction | None |
| Refinement method | Full-matrix least-squares on F$^2$ |
| Data/restraints/parameters | 2674/1/135 |
| Goodness-of-fit on F$^2$ | 1.055 |
| Final R indices [I > 2sigma(I)] | R1 = 0.0383, wR2 = 0.0939 |
| R indices (all data) | R1 = 0.0409, wR2 = 0.0959 |
| Absolute structure parameter | 0.02(6) |
| Largest diff. peak and hole | 0.310 and −0.135 e.Å$^{-3}$ |

TABLE 2

Atomic coordinates (×10$^4$) and equivalent isotropic displacement parameters (Å$^2$ × 10$^3$) for 2-5.

| | x | y | z | U(eq) |
|---|---|---|---|---|
| C(1) | 10896(3) | 4999(4) | 3165(2) | 45(1) |
| C(2) | 10015(3) | 6778(3) | 2967(2) | 40(1) |
| C(3) | 7954(3) | 6708(3) | 2311(2) | 36(1) |
| C(4) | 7708(3) | 5658(3) | 1234(2) | 43(1) |
| C(5) | 8554(3) | 3861(3) | 1506(2) | 44(1) |
| C(6) | 11521(4) | 2227(3) | 2315(2) | 53(1) |
| C(7) | 5074(3) | 8626(4) | 1808(3) | 62(1) |
| C(11) | 6300(5) | 5224(6) | 4909(3) | 85(1) |
| Cl(1) | 2362(1) | 4966(1) | 194(1) | 53(1) |
| Cl(2) | 8214(1) | 1057(1) | 4028(1) | 55(1) |
| F(1) | 10991(2) | 7785(2) | 2346(1) | 55(1) |
| N(1) | 10618(3) | 3989(2) | 2104(2) | 39(1) |
| N(2) | 7187(3) | 8513(2) | 2056(2) | 39(1) |
| O(11) | 5695(3) | 4422(3) | 3856(2) | 68(1) |

U(eq) is defined as one third of the trace of the orthogonalized Uij tensor.

TABLE 3

Bond lengths [Å] and angles [deg] for 2-5.

| | | | |
|---|---|---|---|
| C(1)-N(1) | 1.491(3) | C(2)-C(1)-H(1A) | 109.2 |
| C(1)-C(2) | 1.495(3) | N(1)-C(1)-H(1B) | 109.2 |
| C(1)-H(1A) | 0.9700 | C(2)-C(1)-H(1B) | 109.2 |
| C(1)-H(1B) | 0.9700 | H(1A)-C(1)-H(1B) | 107.9 |
| C(2)-F(1) | 1.406(3) | F(1)-C(2)-C(1) | 109.28(19) |
| C(2)-C(3) | 1.508(3) | F(1)-C(2)-C(3) | 107.49(17) |
| C(2)-H(2) | 0.9800 | C(1)-C(2)-C(3) | 112.33(18) |
| C(3)-N(2) | 1.489(3) | F(1)-C(2)-H(2) | 109.2 |
| C(3)-C(4) | 1.525(3) | C(1)-C(2)-H(2) | 109.2 |
| C(3)-H(3) | 0.9800 | C(3)-C(2)-H(2) | 109.2 |
| C(4)-C(5) | 1.505(3) | N(2)-C(3)-C(2) | 110.26(17) |

TABLE 3-continued

Bond lengths [Å] and angles [deg] for 2-5.

| | | | |
|---|---|---|---|
| C(4)-H(4A) | 0.9700 | N(2)-C(3)-C(4) | 110.51(17) |
| C(4)-H(4B) | 0.9700 | C(2)-C(3)-C(4) | 111.07(18) |
| C(5)-N(1) | 1.494(3) | N(2)-C(3)-H(3) | 108.3 |
| C(5)-H(5A) | 0.9700 | C(2)-C(3)-H(3) | 108.3 |
| C(5)-H(5B) | 0.9700 | C(4)-C(3)-H(3) | 108.3 |
| C(6)-N(1) | 1.490(3) | C(5)-C(4)-C(3) | 109.71(19) |
| C(6)-H(6A) | 0.9600 | C(5)-C(4)-H(4A) | 109.7 |
| C(6)-H(6B) | 0.9600 | C(3)-C(4)-H(4A) | 109.7 |
| C(6)-H(6C) | 0.9600 | C(5)-C(4)-H(4B) | 109.7 |
| C(7)-N(2) | 1.491(3) | C(3)-C(4)-H(4B) | 109.7 |
| C(7)-H(7A) | 0.9600 | H(4A)-C(4)-H(4B) | 108.2 |
| C(7)-H(7B) | 0.9600 | N(1)-C(5)-C(4) | 110.49(18) |
| C(7)-H(7C) | 0.9600 | N(1)-C(5)-H(5A) | 109.6 |
| C(11)-O(11) | 1.402(4) | C(4)-C(5)-H(5A) | 109.6 |
| C(11)-H(11A) | 0.9600 | N(1)-C(5)-H(5B) | 109.6 |
| C(11)-H(11B) | 0.9600 | C(4)-C(5)-H(5B) | 109.6 |
| C(11)-H(11C) | 0.9600 | H(5A)-C(5)-H(5B) | 108.1 |
| N(1)-H(1) | 0.77(2) | N(1)-C(6)-H(6A) | 109.5 |
| N(2)-H(2A) | 0.9000 | N(1)-C(6)-H(6B) | 109.5 |
| N(2)-H(2B) | 0.9000 | H(6A)-C(6)-H(6B) | 109.5 |
| O(11)-H(11) | 0.8200 | N(1)-C(6)-H(6C) | 109.5 |
| N(1)-C(1)-C(2) | 111.88(18) | H(6A)-C(6)-H(6C) | 109.5 |
| N(1)-C(1)-H(1A) | 109.2 | H(6B)-C(6)-H(6C) | 109.5 |
| N(2)-C(7)-H(7A) | 109.5 | C(1)-N(1)-C(5) | 110.83(17) |
| N(2)-C(7)-H(7B) | 109.5 | C(6)-N(1)-C(5) | 111.57(19) |
| H(7A)-C(7)-H(7B) | 109.5 | C(1)-N(1)-H(1) | 107.9(17) |
| N(2)-C(7)-H(7C) | 109.5 | C(6)-N(1)-H(1) | 110.0(17) |
| H(7A)-C(7)-H(7C) | 109.5 | C(5)-N(1)-H(1) | 105.1(18) |
| H(7B)-C(7)-H(7C) | 109.5 | C(3)-N(2)-C(7) | 113.99(19) |
| O(11)-C(11)-H(11A) | 109.5 | C(3)-N(2)-H(2A) | 108.8 |
| O(11)-C(11)-H(11B) | 109.5 | C(7)-N(2)-H(2A) | 108.8 |
| H(11A)-C(11)-H(11B) | 109.5 | C(3)-N(2)-H(2B) | 108.8 |
| O(11)-C(11)-H(11C) | 109.5 | C(7)-N(2)-H(2B) | 108.8 |
| H(11A)-C(11)-H(11C) | 109.5 | H(2A)-N(2)-H(2B) | 107.6 |
| H(11B)-C(11)-H(11C) | 109.5 | C(11)-O(11)-H(11) | 109.5 |
| C(1)-N(1)-C(6) | 111.2(2) | | |

TABLE 4

Anisotropic displacement parameters (Å² × 10³) for 2-5.
The anisotropic displacement factor exponent takes the form:
$-2\pi^2 [h^2 a^{*2} U11 + \ldots + 2 h k a^* b^* U12]$

| | U11 | U22 | U33 | U23 | U13 | U12 |
|---|---|---|---|---|---|---|
| C(1) | 45(1) | 49(1) | 38(1) | 0(1) | 6(1) | 3(1) |
| C(2) | 41(1) | 41(1) | 37(1) | −6(1) | 8(1) | −5(1) |
| C(3) | 38(1) | 39(1) | 35(1) | −1(1) | 13(1) | −3(1) |
| C(4) | 43(1) | 43(1) | 40(1) | −9(1) | 4(1) | 0(1) |
| C(5) | 44(1) | 39(1) | 46(1) | −9(1) | 8(1) | −5(1) |
| C(6) | 59(2) | 40(1) | 62(2) | 7(1) | 21(1) | 12(1) |
| C(7) | 37(1) | 68(2) | 78(2) | −12(1) | 12(1) | 8(1) |
| C(11) | 69(2) | 112(3) | 77(2) | −25(2) | 21(2) | 7(2) |
| Cl(1) | 70(1) | 52(1) | 43(1) | −3(1) | 25(1) | −10(1) |
| Cl(2) | 68(1) | 58(1) | 43(1) | −10(1) | 21(1) | −3(1) |
| F(1) | 41(1) | 49(1) | 75(1) | 2(1) | 18(1) | −9(1) |
| N(1) | 47(1) | 36(1) | 40(1) | 4(1) | 18(1) | 2(1) |
| N(2) | 37(1) | 43(1) | 39(1) | −6(1) | 15(1) | 0(1) |
| O(11) | 59(1) | 80(2) | 63(1) | 0(1) | 14(1) | 5(1) |

TABLE 5

Hydrogen coordinates (×10⁴) and isotropic displacement parameters (Å² × 10³) for 2-5.

| | x | y | z | U(eq) |
|---|---|---|---|---|
| H(1A) | 12248 | 5118 | 3517 | 54 |
| H(1B) | 10335 | 4358 | 3675 | 54 |
| H(2) | 10113 | 7348 | 3689 | 48 |
| H(3) | 7231 | 6126 | 2773 | 44 |
| H(4A) | 6367 | 5558 | 853 | 52 |
| H(4B) | 8336 | 6256 | 740 | 52 |
| H(5A) | 7885 | 3246 | 1973 | 52 |
| H(5B) | 8403 | 3198 | 820 | 52 |
| H(6A) | 12857 | 2358 | 2661 | 79 |
| H(6B) | 11341 | 1615 | 1617 | 79 |
| H(6C) | 10945 | 1575 | 2802 | 79 |
| H(7A) | 4507 | 7821 | 1218 | 92 |
| H(7B) | 4671 | 9795 | 1577 | 92 |
| H(7C) | 4683 | 8333 | 2468 | 92 |
| H(11A) | 7656 | 5114 | 5184 | 128 |
| H(11B) | 5699 | 4665 | 5421 | 128 |
| H(11C) | 5960 | 6441 | 4843 | 128 |
| H(2A) | 7550 | 8924 | 1463 | 46 |
| H(2B) | 7704 | 9209 | 2644 | 46 |
| H(11) | 6251 | 3486 | 3866 | 102 |
| H(1) | 11060(30) | 4510(30) | 1710(20) | 29(6) |

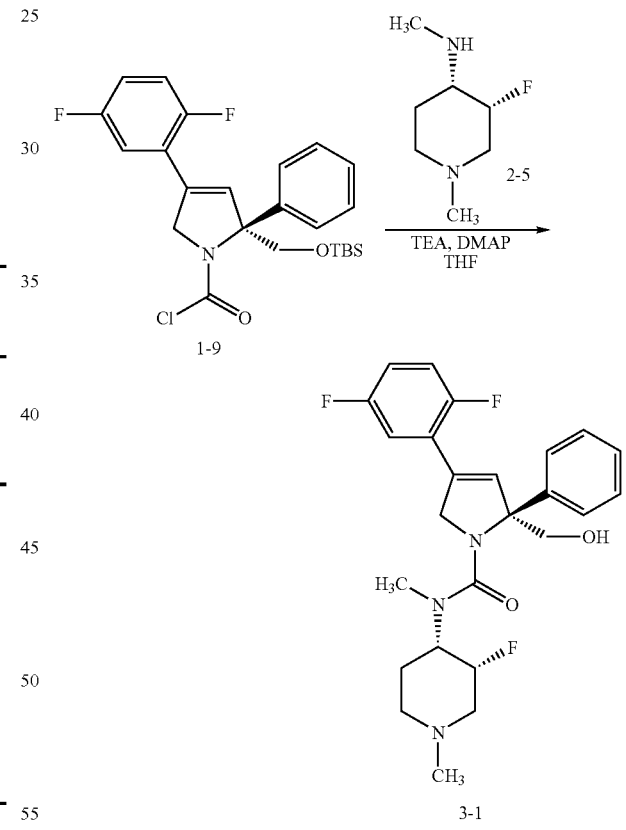

SCHEME 3

(2S)-4-(2,5-Difluorophenyl)-N-[(3R,4S)-3-fluoro-1-methylpiperidin-4-yl]-2-(hydroxymethyl)-N-methyl-2-phenyl-2,5-dihydro-1H-pyrrole-1-carboxamide (3-1)

To a solution of 1.6 g (3.45 mmol) of carbamoyl chloride 1-9 in 25 mL of THF was added 630 mg (4.31 mmol) of amine 2-5, 1.44 mL (10.3 mmol) of triethylamine, and a catalytic amount of DMAP. After stirring for 24 h at room temperature, the reaction was partitioned between EtOAc and saturated aqueous NaHCO$_3$, the organic was washed with brine, dried over Na$_2$SO$_4$, and concentrated by rotary evaporation. The residue was purified by silica gel chromatography with EtOAc/hexanes to provide 1.7 g of a pale yellow taffy. This was dissolved in 75 mL of CH$_3$CN, 3 mL of triethylamine trihydrofluoride was added, and the mixture was stirred for 24 h at room temperature. An additional 3 mL of triethylamine trihydrofluoride was added and the reaction was heated at 37° C. for an additional 24 h. The reaction was then dumped into saturated aqueous NaHCO$_3$, extracted 3× with EtOAc, washed with brine, dried over Na$_2$SO$_4$, and concentrated by rotary evaporation. The residue was purified by silica gel chromatography with EtOAc—20:1:1 EtOH/NH$_4$OH/H$_2$0 to provide 3-1 as a white solid. Data for 3-1: $^1$HNMR (500 MHz, CDCl$_3$) δ 7.4-7.2 (m, 5H), 7.1-6.9 (m, 3H), 6.3 (s, 1H), 5.25 (m, 1H), 4.9 (d, 1H), 4.8 (d, 1H), 4.6 (d, 1H), 4.45 (m, 1H), 4.1-4.0 (m, 2H), 3.2-3.1 (m, 1H), 3.1 (s, 3H), 3.0 (m, 1H), 2.4-2.3 (m, 1H), 2.3 (s, 3H), 2.3-2.2 (m, 2H), 1.7 (m, 1H) ppm. HRMS (ES) calc'd M+H for C$_{25}$H$_{28}$F$_3$N$_3$O$_2$: 460.2207. Found: 460.2213.

Scheme 3A (2S)-4-(2,5-Difluorophenyl)-N-[(3R,4S)-3-fluoro-1-methylpiperidin-4-yl]-2-(hydroxymethyl)-N-methyl-2-phenyl-2,5-dihydro-1H-pyrrole-1-carboxamide (3-1)

In a flask equipped with overhead stirrer, thermocouple, and nitrogen/vacuum inlet was charged the carbamyl chloride 1-9 in IPAC (0.9 L). To this solution was added 0.9 L DMF, 111 gms fluorodiamine 2-5 and 540 ml diisopropylethylamine. The solution was warmed to 60° C. for 15 hrs and assayed for conversion of carbamyl chloride to product. The reaction is considered complete when the conversion of carbamyl chloride to product is >98A % at 200 nm by HPLC. The reaction was cooled to 5° C. and 450 ml 6NHCl was added. The solution was aged until desilylation was complete (>99A % at 200 nm), about 2 hrs.

Isopropylacetate (3 L) and then 8wt % aqueous sodium bicarbonate was added (2 L) to the reaction mixture, which was allowed to warm to 15-20° C. The layers were separated and the aqueous layer extracted once with 3 L IPAC. The combined organic layers were washed twice with 1L water. The washed organic solution was concentrated to 5 liters and, while at 35-40° C. transferred to another flask through a 1 μm polypropylene filter. Distillation was continued until a volume of 1 L was obtained and then the reaction was cooled to room temperature over two hours. Heptane (1 L) was then slowly added over 2 hrs. The resultant slurry was filtered onto a sintered glass funnel and the crystalline product was washed 3 times with 500 mls of 2:1 heptane: isopropylacetate as displacement washes. The solid 3-1 was dried with a sweep of nitrogen overnight. $^1$HNMR and HRMS data for this solid corresponded to the data of the product from Scheme 3.

Figure 2:
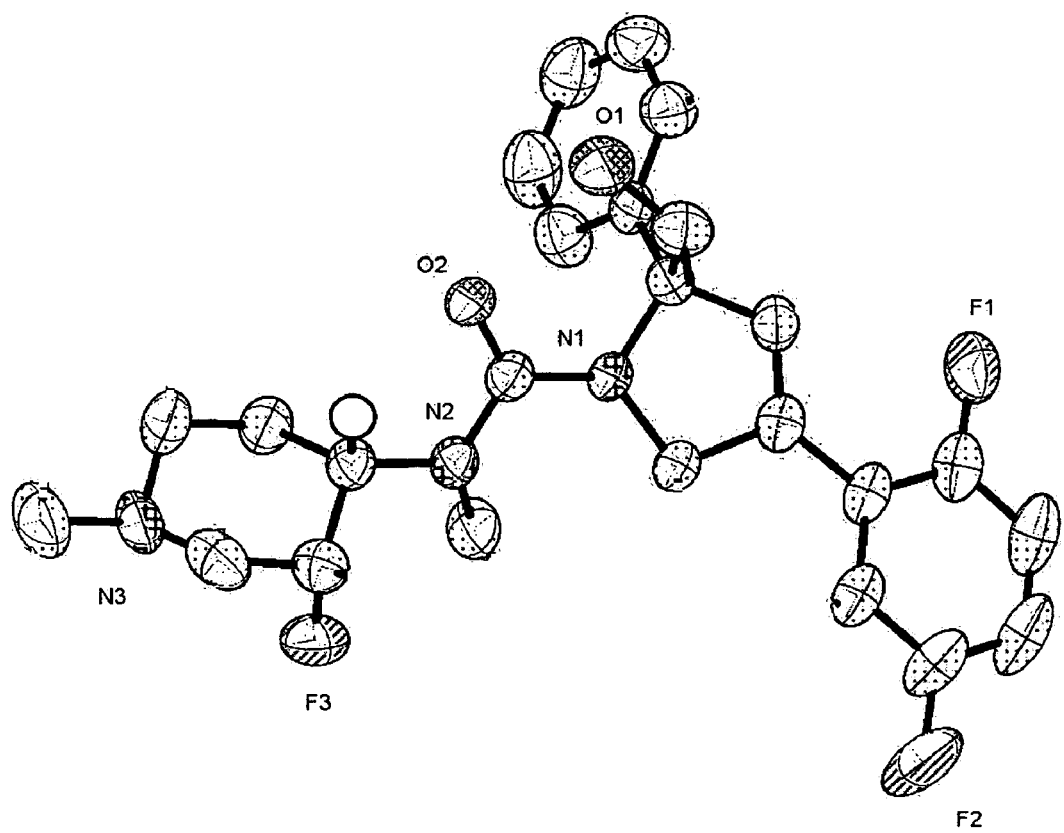
FIG. 2 An ORTEP drawing of Compound 3-1 In order to simplify the drawing most of the hydrogen atoms are not shown.

A single crystal from the above preparation was selected for single crystal x-ray data collection on a Bruker Smart Apex system. The crystal was colorless polyhedron with dimensions of 0.14 mM×0.13 mM×0.13 mM. The unit cell was collected on 30 second scan rate and auto indexing gave the cell setting to be orthorhombic. The structure was solved in the orthorhombic P 2$_1$2$_1$2$_1$ space group after a quadrant data collection using 30 second scan rate. See Tables 6-10 for tabulated information pertaining to the final specifications of the solved structure. A computer drawing of the structure of 3-1 is shown in FIG. 2.

TABLE 6

Crystal data and structure refinement for 3-1.

| | |
|---|---|
| Empirical formula | C$_{25}$ H$_{28}$ F$_3$ N$_3$ O$_2$ |
| Formula weight | 459.50 |
| Temperature | 298(2) K |
| Wavelength | 0.71073 Å |
| Crystal system, space group | Orthorhombic, P2(1)2(1)2(1) |
| Unit cell dimensions | a = 11.3916(14) Å alpha = 90 deg. |
| | b = 11.4808(14) Å beta = 90 deg. |
| | c = 17.718(2) Å gamma = 90 deg. |
| Volume | 2317.3(5) Å$^3$ |
| Z, Calculated density | 4, 1.317 Mg/m$^3$ |
| Absorption coefficient | 0.101 mm$^{-1}$ |
| F(000) | 968 |
| Crystal size | 0.14 mm × 0.13 mm × 0.13 mm |
| Theta range for data collection | 2.11 to 26.43 deg. |
| Limiting indices | −14 <= h <= 14, −14 <= k <= 14, −22 <= l <= 22 |
| Reflections collected/unique | 22539/2698 [R(int) = 0.0405] |
| Completeness to theta = 26.43 | 99.8% |
| Absorption correction | None |
| Refinement method | Full-matrix least-squares on F$^2$ |
| Data/restraints/parameters | 2698/0/301 |
| Goodness-of-fit on F^2 | 1.157 |
| Final R indices [I > 2sigma(I)] | R1 = 0.0429, wR2 = 0.0993 |
| R indices (all data) | R1 = 0.0550, wR2 = 0.1047 |
| Absolute structure parameter | 0(10) |
| Largest diff. peak and hole | 0.165 and −0.120 e.Å$^{-3}$ |

TABLE 7

Atomic coordinates (×10$^4$) and equivalent isotropic displacement parameters (Å$^2$ × 10$^3$) for Compound 3-1.

| | x | y | z | U(eq) |
|---|---|---|---|---|
| C(5) | −2267(3) | 6218(3) | 2092(2) | 53(1) |
| C(25) | 5273(3) | 3363(4) | 2054(3) | 93(1) |
| O(2) | 24(2) | 5125(1) | 1748(1) | 50(1) |
| F(3) | 4039(2) | 6650(2) | 1452(1) | 74(1) |
| F(1) | −3491(2) | 9889(2) | 691(1) | 73(1) |
| O(1) | −2142(2) | 5028(2) | 2243(1) | 63(1) |
| C(18) | 313(2) | 6092(2) | 1508(1) | 39(1) |
| C(1) | −1779(2) | 6659(2) | 1327(2) | 41(1) |
| N(1) | −501(2) | 6935(2) | 1354(1) | 41(1) |
| C(12) | −1597(2) | 9968(2) | 1225(1) | 44(1) |
| C(20) | 2315(2) | 5486(2) | 1637(1) | 40(1) |
| N(2) | 1463(2) | 6357(2) | 1377(1) | 42(1) |
| F(2) | 177(2) | 12521(2) | 1590(1) | 105(1) |
| C(4) | −303(2) | 8186(2) | 1463(2) | 50(1) |
| C(17) | −680(3) | 10679(2) | 1453(2) | 53(1) |
| C(2) | −2267(2) | 7865(2) | 1205(2) | 44(1) |
| C(11) | −3201(3) | 5372(2) | 626(2) | 53(1) |
| C(24) | 2651(3) | 4586(2) | 1056(2) | 52(1) |
| C(3) | −1487(2) | 8695(2) | 1296(1) | 42(1) |
| N(3) | 4491(2) | 4230(2) | 1726(2) | 60(1) |
| C(19) | 1830(3) | 7139(3) | 769(2) | 58(1) |
| C(15) | −1705(4) | 12401(3) | 1043(2) | 78(1) |
| C(21) | 3404(2) | 6016(2) | 1983(2) | 52(1) |
| C(16) | −754(3) | 11868(3) | 1362(2) | 68(1) |
| C(6) | −2088(2) | 5851(2) | 671(1) | 40(1) |
| C(13) | −2555(3) | 10532(3) | 918(2) | 55(1) |
| C(14) | −2613(4) | 11716(3) | 818(2) | 71(1) |
| C(7) | −1323(3) | 5615(3) | 89(2) | 57(1) |
| C(10) | −3518(3) | 4678(3) | 26(2) | 64(1) |

TABLE 7-continued

Atomic coordinates (×10⁴) and equivalent isotropic displacement parameters ($Å^2 \times 10^3$) for Compound 3-1.

|      | x       | y       | z       | U(eq) |
|------|---------|---------|---------|-------|
| C(9) | −2748(3)| 4452(3) | −544(2) | 70(1) |
| C(22)| 4183(3) | 5085(3) | 2291(2) | 64(1) |
| C(8) | −1644(3)| 4917(3) | −508(2) | 73(1) |
| C(23)| 3449(3) | 3691(2) | 1414(2) | 63(1) |

U(eq) is defined as one third of the trace of the orthogonalized Uij tensor.

TABLE 8

Bond lengths [Å] and angles [deg] for 3-1.

| | | | |
|---|---|---|---|
| C(5)-O(1) | 1.399(3) | N(2)-C(19) | 1.464(3) |
| C(5)-C(1) | 1.550(4) | F(2)-C(16) | 1.360(4) |
| C(5)-H(5A) | 0.9700 | C(4)-C(3) | 1.500(3) |
| C(5)-H(5B) | 0.9700 | C(4)-H(4A) | 0.9700 |
| C(25)-N(3) | 1.457(4) | C(4)-H(4B) | 0.9700 |
| C(25)-H(25A) | 0.9600 | C(17)-C(16) | 1.376(4) |
| C(25)-H(25B) | 0.9600 | C(17)-H(17) | 0.9300 |
| C(25)-H(25C) | 0.9600 | C(2)-C(3) | 1.313(4) |
| O(2)-C(18) | 1.233(3) | C(2)-H(2) | 0.9300 |
| F(3)-C(21) | 1.393(3) | C(11)-C(10) | 1.376(4) |
| F(1)-C(13) | 1.358(4) | C(11)-C(6) | 1.385(4) |
| O(1)-H(1) | 0.8200 | C(11)-H(11) | 0.9300 |
| C(18)-N(1) | 1.368(3) | C(24)-C(23) | 1.511(4) |
| C(18)-N(2) | 1.364(3) | C(24)-H(24A) | 0.9700 |
| C(1)-N(1) | 1.490(3) | C(24)-H(24B) | 0.9700 |
| C(1)-C(2) | 1.508(3) | N(3)-C(22) | 1.446(4) |
| C(1)-C(6) | 1.528(4) | N(3)-C(23) | 1.448(4) |
| N(1)-C(4) | 1.466(3) | C(19)-H(19A) | 0.9600 |
| C(12)-C(13) | 1.381(4) | C(19)-H(19B) | 0.9600 |
| C(12)-C(17) | 1.386(4) | C(19)-H(19C) | 0.9600 |
| C(12)-C(3) | 1.473(3) | C(15)-C(14) | 1.360(5) |
| C(20)-N(2) | 1.468(3) | C(15)-C(16) | 1.367(5) |
| C(20)-C(24) | 1.508(4) | C(15)-H(15) | 0.9300 |
| C(20)-C(21) | 1.512(4) | C(21)-C(22) | 1.492(4) |
| C(20)-H(20) | 0.9800 | C(21)-H(21) | 0.9800 |
| C(6)-C(7) | 1.377(4) | C(18)-N(1)-C(4) | 124.2(2) |
| C(13)-C(14) | 1.372(4) | C(18)-N(1)-C(1) | 121.18(19) |
| C(14)-H(14) | 0.9300 | C(4)-N(1)-C(1) | 111.32(19) |
| C(7)-C(8) | 1.377(4) | C(13)-C(12)-C(17) | 115.7(2) |
| C(7)-H(7) | 0.9300 | C(13)-C(12)-C(3) | 124.5(3) |
| C(10)-C(9) | 1.362(4) | C(17)-C(12)-C(3) | 119.7(2) |
| C(10)-H(10) | 0.9300 | N(2)-C(20)-C(24) | 114.8(2) |
| C(9)-C(8) | 1.368(5) | N(2)-C(20)-C(21) | 113.3(2) |
| C(9)-H(9) | 0.9300 | C(24)-C(20)-C(21) | 110.1(2) |
| C(22)-H(22A) | 0.9700 | N(2)-C(20)-H(20) | 105.9 |
| C(22)-H(22B) | 0.9700 | C(24)-C(20)-H(20) | 105.9 |
| C(8)-H(8) | 0.9300 | C(21)-C(20)-H(20) | 105.9 |
| C(23)-H(23A) | 0.9700 | C(18)-N(2)-C(19) | 122.5(2) |
| C(23)-H(23B) | 0.9700 | C(18)-N(2)-C(20) | 115.44(19) |
| O(1)-C(5)-C(1) | 116.7(2) | C(19)-N(2)-C(20) | 117.40(19) |
| O(1)-C(5)-H(5A) | 108.1 | N(1)-C(4)-C(3) | 102.5(2) |
| C(1)-C(5)-H(5A) | 108.1 | N(1)-C(4)-H(4A) | 111.3 |
| O(1)-C(5)-H(5B) | 108.1 | C(3)-C(4)-H(4A) | 111.3 |
| C(1)-C(5)-H(5B) | 108.1 | N(1)-C(4)-H(4B) | 111.3 |
| H(5A)-C(5)-H(5B) | 107.3 | C(3)-C(4)-H(4B) | 111.3 |
| N(3)-C(25)-H(25A) | 109.5 | H(4A)-C(4)-H(4B) | 109.2 |
| N(3)-C(25)-H(25B) | 109.5 | C(16)-C(17)-C(12) | 120.3(3) |
| H(25A)-C(25)-H(25B) | 109.5 | C(16)-C(17)-H(17) | 119.9 |
| N(3)-C(25)-H(25C) | 109.5 | C(12)-C(17)-H(17) | 119.9 |
| H(25A)-C(25)-H(25C) | 109.5 | C(3)-C(2)-C(1) | 113.6(2) |
| H(25B)-C(25)-H(25C) | 109.5 | C(3)-C(2)-H(2) | 123.2 |
| C(5)-O(1)-H(1) | 109.5 | C(1)-C(2)-H(2) | 123.2 |
| O(2)-C(18)-N(1) | 121.6(2) | C(10)-C(11)-C(6) | 121.0(3) |
| O(2)-C(18)-N(2) | 121.0(2) | C(10)-C(11)-H(11) | 119.5 |
| N(1)-C(18)-N(2) | 117.3(2) | C(6)-C(11)-H(11) | 119.5 |
| N(1)-C(1)-C(2) | 99.73(19) | C(20)-C(24)-C(23) | 109.4(2) |
| N(1)-C(1)-C(6) | 112.2(2) | C(20)-C(24)-H(24A) | 109.8 |
| C(2)-C(1)-C(6) | 111.3(2) | C(23)-C(24)-H(24A) | 109.8 |
| N(1)-C(1)-C(5) | 113.1(2) | C(20)-C(24)-H(24B) | 109.8 |
| C(2)-C(1)-C(5) | 107.1(2) | C(23)-C(24)-H(24B) | 109.8 |

TABLE 8-continued

Bond lengths [Å] and angles [deg] for 3-1.

| | | | |
|---|---|---|---|
| C(6)-C(1)-C(5) | 112.6(2) | H(24A)-C(24)-H(24B) | 108.2 |
| C(2)-C(3)-C(12) | 130.7(2) | C(9)-C(10)-C(11) | 120.9(3) |
| C(2)-C(3)-C(4) | 110.5(2) | C(9)-C(10)-H(10) | 119.5 |
| C(12)-C(3)-C(4) | 118.7(2) | C(11)-C(10)-H(10) | 119.5 |
| C(22)-N(3)-C(23) | 110.8(2) | C(10)-C(9)-C(8) | 118.9(3) |
| C(22)-N(3)-C(25) | 109.7(3) | C(10)-C(9)-H(9) | 120.5 |
| C(23)-N(3)-C(25) | 111.2(3) | C(8)-C(9)-H(9) | 120.5 |
| N(2)-C(19)-H(19A) | 109.5 | N(3)-C(22)-C(21) | 112.1(2) |
| N(2)-C(19)-H(19B) | 109.5 | N(3)-C(22)-H(22A) | 109.2 |
| H(19A)-C(19)-H(19B) | 109.5 | C(21)-C(22)-H(22A) | 109.2 |
| N(2)-C(19)-H(19C) | 109.5 | N(3)-C(22)-H(22B) | 109.2 |
| H(19A)-C(19)-H(19C) | 109.5 | C(21)-C(22)-H(22B) | 109.2 |
| H(19B)-C(19)-H(19C) | 109.5 | H(22A)-C(22)-H(22B) | 107.9 |
| C(14)-C(15)-C(16) | 117.7(3) | C(9)-C(8)-C(7) | 120.4(3) |
| C(14)-C(15)-H(15) | 121.1 | C(9)-C(8)-H(8) | 119.8 |
| C(16)-C(15)-H(15) | 121.1 | C(7)-C(8)-H(8) | 119.8 |
| F(3)-C(21)-C(22) | 108.3(2) | N(3)-C(23)-C(24) | 111.3(2) |
| F(3)-C(21)-C(20) | 111.3(2) | N(3)-C(23)-H(23A) | 109.4 |
| C(22)-C(21)-C(20) | 110.4(2) | C(24)-C(23)-H(23A) | 109.4 |
| F(3)-C(21)-H(21) | 109.0 | N(3)-C(23)-H(23B) | 109.4 |
| C(22)-C(21)-H(21) | 109.0 | C(24)-C(23)-H(23B) | 109.4 |
| C(20)-C(21)-H(21) | 109.0 | H(23A)-C(23)-H(23B) | 108.0 |
| F(2)-C(16)-C(15) | 119.6(3) | | |
| F(2)-C(16)-C(17) | 117.7(3) | | |
| C(15)-C(16)-C(17) | 122.8(3) | | |
| C(7)-C(6)-C(11) | 117.3(3) | | |
| C(7)-C(6)-C(1) | 122.9(2) | | |
| C(11)-C(6)-C(1) | 119.7(2) | | |
| F(1)-C(13)-C(14) | 117.6(3) | | |
| F(1)-C(13)-C(12) | 118.8(3) | | |
| C(14)-C(13)-C(12) | 123.6(3) | | |
| C(15)-C(14)-C(13) | 119.9(3) | | |
| C(15)-C(14)-H(14) | 120.0 | | |
| C(13)-C(14)-H(14) | 120.0 | | |
| C(6)-C(7)-C(8) | 121.5(3) | | |
| C(6)-C(7)-H(7) | 119.3 | | |
| C(8)-C(7)-H(7) | 119.3 | | |

TABLE 9

Anisotropic displacement parameters ($Å^2 \times 10^3$) for 3-1.
The anisotropic displacement factor exponent takes the form:
$-2\pi^2 [ h^2 a^{*2} U11 + \ldots + 2 h k a^* b^* U12 ]$

| | U11 | U22 | U33 | U23 | U13 | U12 |
|---|---|---|---|---|---|---|
| C(5) | 52(2) | 57(2) | 50(2) | 2(1) | 4(1) | −5(1) |
| C(25) | 53(2) | 89(3) | 136(3) | 38(3) | 3(2) | 21(2) |
| O(2) | 43(1) | 33(1) | 75(1) | 13(1) | −4(1) | 0(1) |
| F(3) | 58(1) | 57(1) | 109(1) | 18(1) | −2(1) | −15(1) |
| F(1) | 65(1) | 68(1) | 86(1) | 5(1) | −14(1) | 19(1) |
| O(1) | 63(1) | 58(1) | 69(1) | 21(1) | 9(1) | −6(1) |
| C(18) | 42(1) | 32(1) | 42(1) | 1(1) | −2(1) | 2(1) |
| C(1) | 35(1) | 38(1) | 50(1) | 4(1) | 2(1) | 1(1) |
| N(1) | 39(1) | 28(1) | 55(1) | 4(1) | −2(1) | 3(1) |
| C(12) | 60(2) | 35(1) | 36(1) | 2(1) | 6(1) | 12(1) |
| C(20) | 41(1) | 36(1) | 43(1) | 8(1) | 2(1) | 4(1) |
| N(2) | 41(1) | 35(1) | 50(1) | 9(1) | 4(1) | 4(1) |
| F(2) | 144(2) | 40(1) | 131(2) | −4(1) | −27(2) | −12(1) |
| C(4) | 45(1) | 30(1) | 74(2) | 6(1) | −6(1) | 3(1) |
| C(17) | 69(2) | 37(1) | 53(2) | 2(1) | 3(2) | 9(1) |
| C(2) | 41(1) | 41(1) | 50(1) | −2(1) | −1(1) | 9(1) |
| C(11) | 49(2) | 51(2) | 58(2) | 5(1) | −6(1) | 0(1) |
| C(24) | 55(2) | 44(1) | 58(2) | −3(1) | −2(1) | 5(1) |
| C(3) | 49(1) | 39(1) | 38(1) | 2(1) | 5(1) | 9(1) |
| N(3) | 40(1) | 58(1) | 82(2) | 20(1) | 9(1) | 13(1) |
| C(19) | 53(2) | 49(2) | 73(2) | 24(1) | 10(2) | 7(1) |
| C(15) | 127(3) | 38(2) | 68(2) | 1(2) | −3(2) | 25(2) |
| C(21) | 46(2) | 51(2) | 58(2) | −6(1) | −1(1) | −1(1) |
| C(16) | 105(3) | 35(1) | 65(2) | −2(1) | −5(2) | 3(1) |
| C(6) | 40(1) | 33(1) | 48(1) | 7(1) | −2(1) | 6(1) |
| C(13) | 67(2) | 53(2) | 47(2) | 0(1) | 4(1) | 19(2) |
| C(14) | 99(3) | 53(2) | 62(2) | 4(2) | −6(2) | 35(2) |
| C(7) | 51(2) | 66(2) | 56(2) | −8(2) | 1(1) | 5(2) |
| C(10) | 61(2) | 55(2) | 75(2) | 0(2) | −21(2) | −6(2) |
| C(9) | 82(2) | 61(2) | 67(2) | −18(2) | −23(2) | 14(2) |
| C(22) | 43(2) | 81(2) | 67(2) | 12(2) | −6(1) | −3(2) |
| C(8) | 75(2) | 83(2) | 63(2) | −19(2) | 0(2) | 21(2) |
| C(23) | 65(2) | 42(1) | 83(2) | 3(2) | 8(2) | 12(2) |

TABLE 10

Hydrogen coordinates ($\times 10^4$) and isotropic displacement parameters ($Å^2 \times 10^3$) for 3-1.

| | x | y | z | U(eq) |
|---|---|---|---|---|
| H(5A) | −1881 | 6648 | 2493 | 64 |
| H(5B) | −3096 | 6408 | 2114 | 64 |
| H(25A) | 4878 | 2968 | 2458 | 139 |
| H(25B) | 5963 | 3742 | 2246 | 139 |
| H(25C) | 5495 | 2810 | 1674 | 139 |
| H(1) | −1483 | 4815 | 2120 | 95 |
| H(20) | 1926 | 5057 | 2045 | 48 |
| H(4A) | 287 | 8479 | 1116 | 60 |
| H(4B) | −61 | 8355 | 1977 | 60 |
| H(17) | −13 | 10353 | 1669 | 64 |
| H(2) | −3046 | 8007 | 1077 | 53 |

TABLE 10-continued

Hydrogen coordinates (×10⁴) and isotropic displacement parameters ($Å^2 \times 10^3$) for 3-1.

| | x | y | z | U(eq) |
|---|---|---|---|---|
| H(11) | −3743 | 5520 | 1006 | 63 |
| H(24A) | 3051 | 4959 | 637 | 62 |
| H(24B) | 1951 | 4208 | 863 | 62 |
| H(19A) | 1181 | 7275 | 435 | 88 |
| H(19B) | 2463 | 6789 | 492 | 88 |
| H(19C) | 2087 | 7865 | 980 | 88 |
| H(15) | −1730 | 13206 | 983 | 93 |
| H(21) | 3171 | 6536 | 2395 | 62 |
| H(14) | −3273 | 12049 | 597 | 85 |
| H(7) | −572 | 5933 | 100 | 69 |
| H(10) | −4268 | 4360 | 9 | 76 |
| H(9) | −2970 | 3989 | −950 | 84 |
| H(22A) | 4894 | 5438 | 2487 | 77 |
| H(22B) | 3787 | 4700 | 2707 | 77 |
| H(8) | −1106 | 4760 | −890 | 88 |
| H(23A) | 3028 | 3288 | 1812 | 76 |
| H(23B) | 3677 | 3120 | 1038 | 76 |

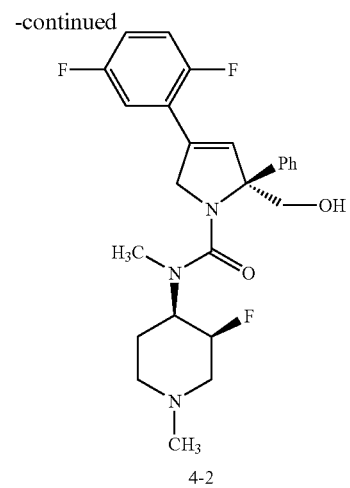

4-2

(2S)-4-(2,5-Difluorophenyl)-N-[(3S,4R)-3-fluoro-1-methylpiperidin-4-yl]-2-(hydroxymethyl)-N-methyl-2-phenyl-2,5-dihydro-1H-pyrrole-1-carboxamide (4-2)

This compound was made in a manner identical to that for 3-1, with the exception of incorporation of the first eluting enantiomer of 2-3 from the chiral column described in Scheme 2, Step 3. Data for 4-2: ¹HNMR (500 MHz, CDCl₃) δ 7.4-7.2 (m, 5H), 7.1-6.9 (m, 3H), 6.3 (s, 1H), 5.4 (bs, 1H), 5.2 (d, 1H), 4.9 (m, 1H), 4.6 (m, 1H), 4.4 (m, 1H), 4.0 (m, 1H), 3.8 (m, 1H), 3.2 (s, 3H), 3.0 (m, 1H), 2.5-2.2 (m, 3H), 2.4 (s, 3H), 1.8-1.6 (m, 2H) ppm. HRMS (ES) calc'd M+H for $C_{25}H_{28}F_3N_3O_2$: 460.2207. Found: 460.2229.

SCHEME 4

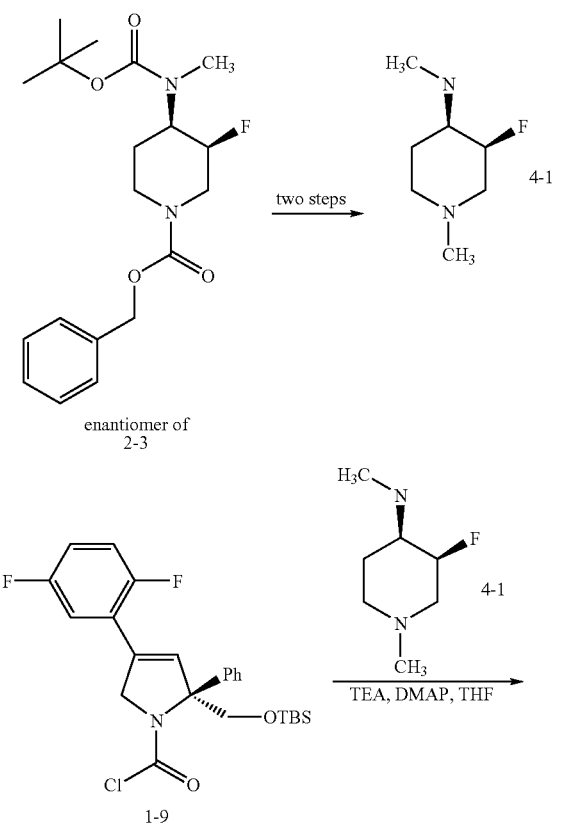

SCHEME 5

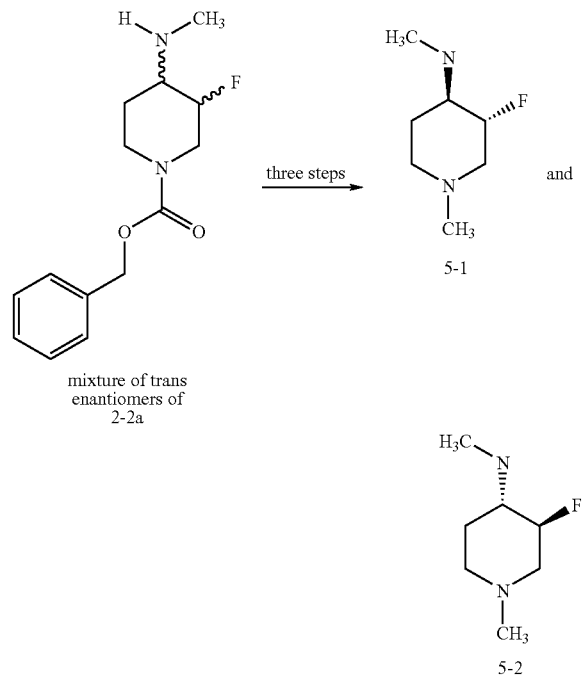

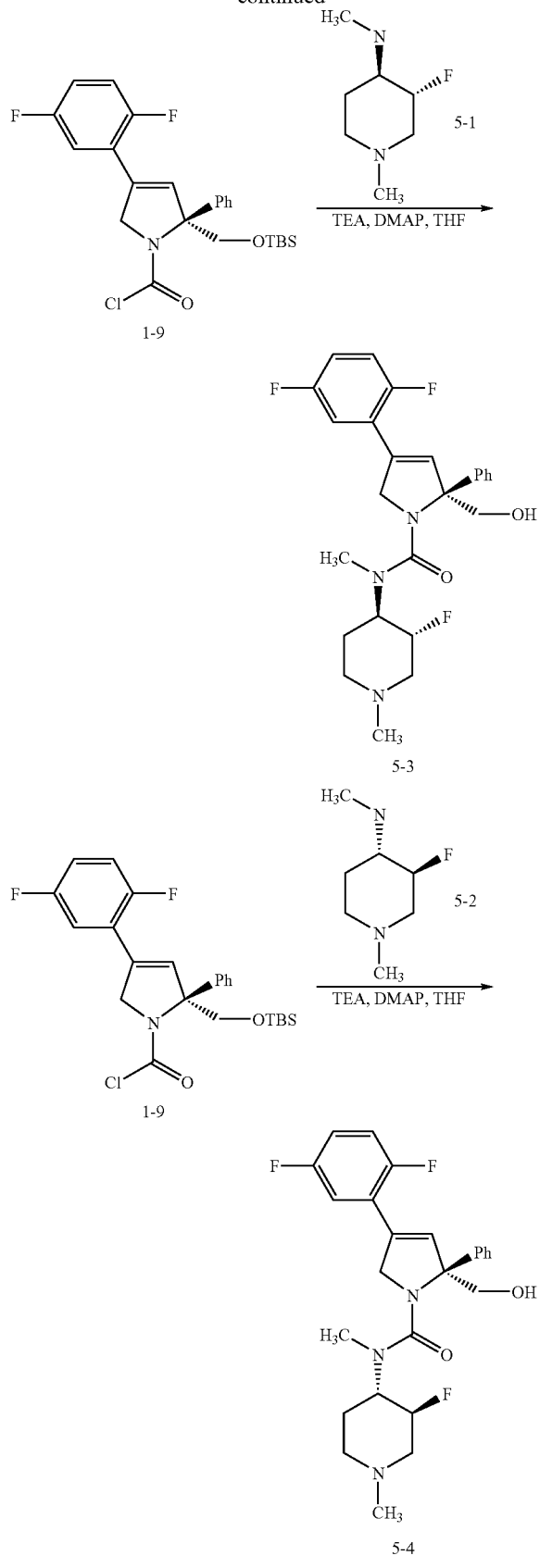

(2S)-4-(2,5-Difluorophenyl)-N-[(3R,4R)-3-fluoro-1-methylpiperidin-4-yl]-2-(hydroxymethyl)-N-methyl-2-phenyl-2,5-dihydro-1H-pyrrole-1-carboxamide (5-3)

This compound was made in a manner identical to that for 3-1, with the exception that the trans isomer of 2-2a was incorporated into the synthesis. Resolution of the enantiomers of "trans-2-3" was carried out chromatographically using a Chiralpak AD© 10×50 cm column with 15% EtOH in hexanes (with 0.1% diethylamine) at 150 mL/min. Analytical HPLC analysis of the eluent on a 4×250 mM Chiralpak AD® column with 15% EtOH in hexanes (with 0.1% diethylamine) at 1 mL/min indicated that first eluting enantiomer has $R_t$=7.30 min and the second enantiomer has $R_t$=11.59 min. The first eluting enantiomer (having unknown absolute stereochemistry) was further processed to provide trans-amine 5-1, which was incorporated into the synthesis of 5-3 following a route identical to that explained in Scheme 2. Data for 5-3: $^1$HNMR (500 MHz, CDCl$_3$) δ 7.4-7.2 (m, 5H), 7.1-6.9 (m, 3H), 6.3 (s, 1H), 5.0-4.7 (m, 4H), 4.5 (m, 1H), 4.0 (m, 1H), 3.8 (m, 1H), 3.3 (m, 1H), 2.9 (s, 3H), 2.85 (m, 1H), 2.35 (s, 3H), 2.2-1.9 (m, 3H), 1.7 (m, 1H) ppm. HRMS (ES) calc'd M+H for $C_{25}H_{28}F_3N_3O_2$: 460.2207. Found: 460.2231. The absolute stereochemistry on the piperidine of compounds 5-3 and 5-4 has not been determined and stereochemistry indicated has been tentatively assigned.

(2S)-4-(2,5-Difluorophenyl)-N-[(3S,4S)-3-fluoro-1-methylpiperidin-4-yl]-2-(hydroxymethyl)-N-methyl-2-phenyl-2,5-dihydro-1H-pyrrole-1-carboxamide (5-4)

This compound was made in a manner identical to that for 5-3, with the exception of incorporation of the second eluting isomer of trans-2-3 from the chiral column. Data for 5-4: $^1$HNMR (500 MHz, CDCl$_3$) δ 7.4-7.2 (m, 5H), 7.1-6.9 (m, 3H), 6.3 (s, 1H), 5.4 (m, 1H), 4.9-4.6 (m, 3H), 4.4 (m, 1H), 4.0 (m, 1H), 3.85 (m, 1H), 3.25 (m, 1H), 3.0 (s, 3H), 2.85 (m, 1H), 2.35 (s, 3H), 2.2-1.9 (m, 4H) ppm. HRMS (ES) calc'd M+H for $C_{25}H_{28}F_3N_3O_2$: 460.2207. Found: 460.2229.

SCHEME 6

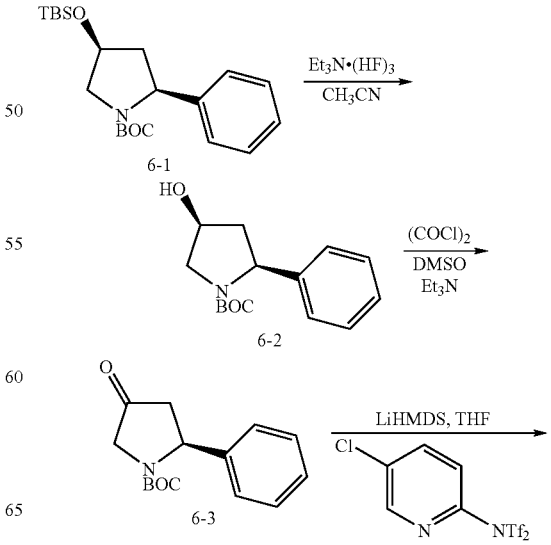

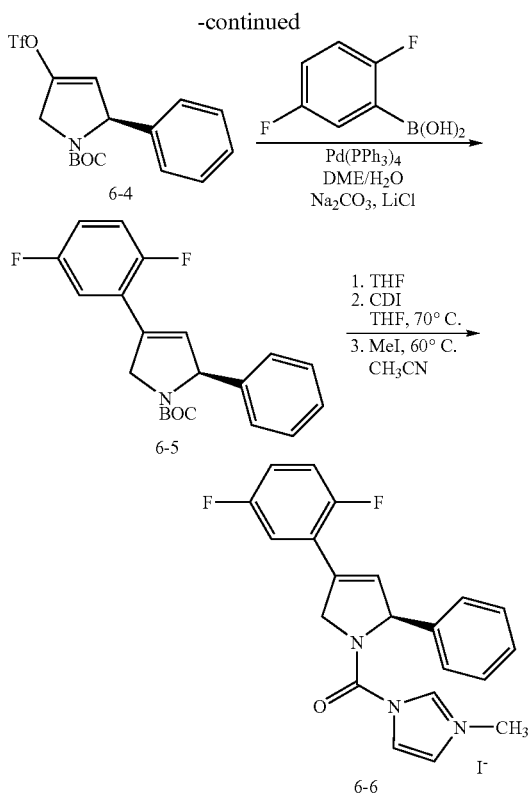

Step 1: (2S,4S)-tert-Butyl 4-hydroxy-2-phenylpyrrolidine-1-carboxylate (6-2)

To a flame dried flask equipped with stir bar was added tert-butyl (2S,4S)-4-{[tert-5 butyl(dimethyl)silyl]oxy}-2-phenylpyrrolidine-1-carboxylate (6-1, prepared from (S)-(−) 4-chloro-3-hydroxybutyronotrile by the method of Maeda, et al *Synlett* 2001, 1808-1810, 7.8 g, 20.7 mmol) and anhydrous acetonitrile (20.0 mL). The resulting solution was treated with triethylamine trihydrofluoride (10.1 mL, 62.0 mmol) while stirring under $N_2$. The reaction stirred 12 hours at 40° C. The reaction was then diluted with EtOAc (100 mL) and poured into 5% aq. $NaHCO_3$. Following cessation of gas evolution, the organic layer was washed three additional times with 5% aq. $NaHCO_3$. The organic layer was dried over magnesium sulfate, filtered and concentrated to provide crude product. Recrystallization was effected from EtOAc/hexanes to provide (2S,4S)-tert-butyl 4-hydroxy-2-phenylpyrrolidine-1-carboxylate (6-2) as a white crystalline solid. $^1$H NMR (300 MHz, $CDCl_3$) rotamers δ 7.38-7.18 (m, 5H), 4.90 (m, 1H), 4.42 (m, 1H), 3.88 (m, 1H), 3.56 (dd, J=11.5, 4.0 Hz, 1H), 2.60 (m, 1H), 2.03 (m, 1H), 1.50 and 1.20 (br s, 9H); MS 208.0 found, 208.1 (M−C($CH_3$)$_3$) required.

Step 2: (2S)-tert-Butyl 4-oxo-2-phenylpyrrolidine-1-carboxylate (6-3)

To a flame dried flask equipped with stir bar was added 150 mL anhydrous dichloromethane which was cooled to −78° C. Oxalyl chloride (3.8 mL, 44 mmol) and DMSO (4.8 mL, 61 mmol) were added sequentially and the reaction stirred for 10 minutes. (2S,4S)-tert-Butyl 4-hydroxy-2-phenylpyrrolidine-1-carboxylate (6-2, 2.28 g, 8.73 mmol) in 10 mL anhydrous dichloromethane was added dropwise and stirred 1 hour at −78° C. Triethylamine (12 mL, 87 mmol) was added and the reaction was warmed to 0° C. over 1 hour. Upon completion, the reaction was washed with 5% $NaHCO_3$, brine and dried over $MgSO_4$. The organic layer was concentrated to provide crude (2S)-tert-butyl 4-oxo-2-phenylpyrrolidine-1-carboxylate (6-3). Recrystallization was effected with EtOAc/hexanes. $^1$H NMR (300 MHz, $CDCl_3$) δ 7.35 (m, 3H), 7.17 (m, 2H), 5.38 (m, 1H), 4.08 (d, J=19.5 Hz, 1H), 3.90 (d, J=19.3 Hz, 1H), 3.13 (dd, J=18.8, 9.8 Hz, 1H), 2.58 (dd, J=18.6, 2.4 Hz, 1H), 1.40 (br s, 9H); MS 206.0 found, 206.1 (M−C($CH_3$)$_3$) required.

Step 3: (2S)-tert-Butyl 2-phenyl-4-{[(trifluoromethyl)sulfonyl]oxy}-2,5-dihydro-1H-pyrrole-1-carboxylate (6-4)

To a flame dried flask equipped with stir bar was added ketone (2S)-tert-butyl 4-oxo-2-phenylpyrrolidine-1-carboxylate (6-3, 0.16 g, 0.62 mmol) and anhydrous THF (2 mL). The resulting solution was cooled to −78° C., and treated dropwise with lithium hexamethyldisilylamide (LHMDS, 0.68 mL, 1M in THF, 0.68 mmoL). The reaction stirred 1 hour at −78° C., and N-(5-chloropyridin-2-yl)-1,1,1-trifluoro-N-[(trifluoromethyl)sulfonyl]methanesulfonamide (0.27 g, 068 mmol) was added neat in one portion. The reaction was allowed to warm to 0° C. and stirred 4 hours total. The reaction was diluted with $Et_2O$ (10 mL) and washed successively with $H_2O$ (10 mL) and brine (10 mL). The organic layer was dried over $MgSO_4$, filtered and concentrated. The crude residue was purified by flash column choromatography (0-20% EtOAc/hexanes gradient, 15 min) to provide (2S)-tert-butyl 2-phenyl4-{[(trifluoromethyl)sulfonyl]oxy}-2,5-dihydro-1H-pyrrole-1-carboxylate (6-4). $^1$H NMR (300 MHz, $CDCl_3$) major rotamer: δ 7.30 (m, 5H), 5.72 (m, 1H), 5.48 (m, 1H), 4.42 (m, 2H), 1.18 (s, 9H); MS 379.0 found 379.1 (M−$CH_3$) required.

Step 4: (2S)-4-(2,5-Difluorophenyl)-2-phenyl-N,N-dimethyl-2,5-dihydro-1H-pyrrole-1-carboxamide (6-5)

To a flame dried flask equipped with stir bar was added (2S)-tert-butyl 2-phenyl-4-{[(trifluoromethyl)sulfonyl]oxy}-2,5-dihydro-1H-pyrrole-1-carboxylate (6-4, 0.250 g, 0.636 mmol), 2,5-difluorophenyl boronic acid (0.251 g, 1.59 mmol), $Na_2CO_3$ (0.202 g, 1.91 mmol), and LiCl (0.081 g, 1.91 mmol). The solids were dissolved in 20 mL 4:1 DME/$H_2O$ and degassed with nitrogen. Pd(PPh$_3$)$_4$ (0.037 g, 0.032 mmol) was added and the reaction was sealed under nitrogen and heated to 90° C. for 2 hours. Upon completion, the reaction was partitioned between 5% aq. $NaHCO_3$ and EtOAc (3×50 mL), and the combined organic layers were dried over $MgSO_4$. Following filtration, the organic layer was concentrated and purified via flash column chromatography ($SiO_2$, 0-20% EtOAc/hexanes gradient) to provide (2S)-tert-butyl 4-(2,5-difluorophenyl)-2-phenyl-2,5-dihydro-1H-pyrrole-1-carboxylate (6-5).

Step 5: 1-{[(2S)-4-(2,5-Difluorophenyl)-2-phenyl-2,5-dihydro-1H-pyrrol-1-yl]carbonyl}-3-methyl-1H-imidazol-3-ium (6-6)

To a flame-dried flask equipped with stir bar under nitrogen was charged 6-5 (0.63 g, 1.75 mmol) and anhydrous $CH_2CL_2$ (10 mL). The resulting solution was treated with trifluoroacetic acid (5 mL) and stirred 1.5 hours at 25° C. Upon completion, the reaction was concentrated, taken up in $CH_2Cl_2$ (50 mL) and washed with 5% $NaHCO_3$ (50 mL). The organic layer was dried ($MgSO_4$), filtered and concentrated under reduced pressure. The resulting free-amine was dissolved in anhydrous THF (10 mL) and treated with carbonyl diimidazole (0.31 g, 1.93 mmol). The resulting solution was refluxed for 4 hours until completion. The reaction was concentrated, taken up in EtOAc (50 mL) and washed with $H_2O$ and brine.

The combined organic layers were dried (MgSO$_4$) and concentrated. The crude acyl imidazole was dissolved in anhydrous CH$_3$CN and treated with MeI (2.2 mL, 36 mmol). The resulting solution was stirred at 25° C. overnight. Upon completion, the reaction was concentrated to give 6-6 as an orange colored solid: LRMS m/z (M+H) 365.9 found, 366.1 required.

SCHEME 7

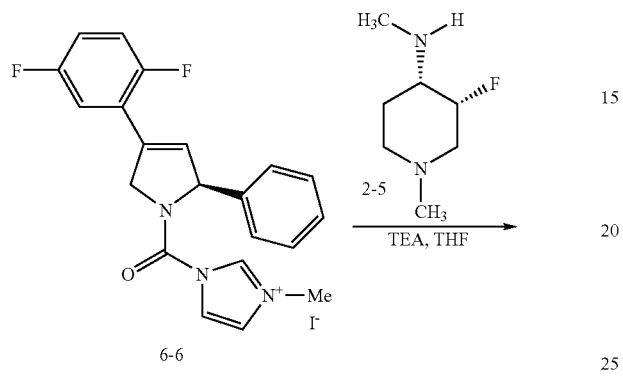

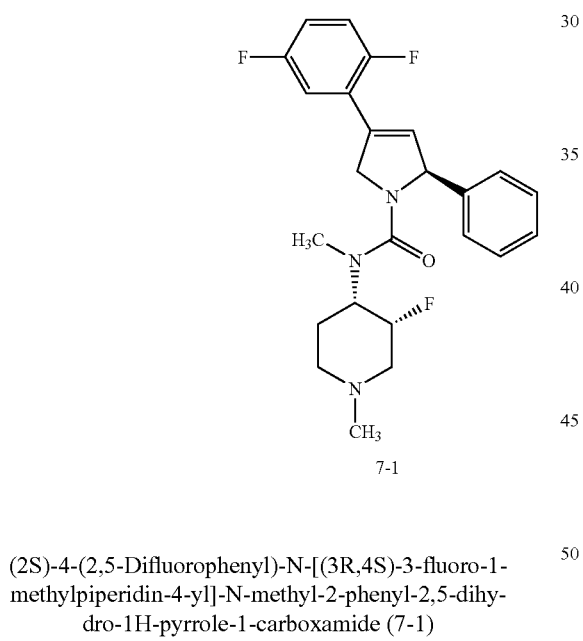

(2S)-4-(2,5-Difluorophenyl)-N-[(3R,4S)-3-fluoro-1-methylpiperidin-4-yl]-N-methyl-2-phenyl-2,5-dihydro-1H-pyrrole-1-carboxamide (7-1)

To a solution of 75 mg (0.15 mmol) of 6-6 in 1 mL of THF was added 40 mg (0.18 mmol) of the bis-HCl salt of amine 2-5 and 106 µL (0.76 mmol) of triethylamine. After stirring for 72 h at room temperature, the reaction was partitioned between CH$_2$Cl$_2$ and saturated aqueous NaHCO$_3$, the organic was washed with brine, dried over MgSO$_4$, and concentrated by rotary evaporation. The residue was purified by silica gel chromatography with 80:10:10 CHCl$_3$/EtOAc/MeOH to provide 7-1 as a white solid. Data for 7-1: HRMS (ES) calc'd M+H for C$_{24}$H$_{26}$F$_3$N$_3$O: 430.2101. Found: 430.2116.

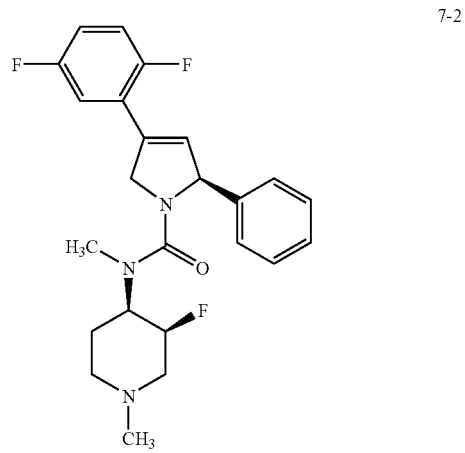

(2S)-4-(2,5-Difluorophenyl)-N-[(3S,4R)-3-fluoro-1-methylpiperidin-4-yl]-N-methyl-2-phenyl-2,5-dihydro-1H-pyrrole-1-carboxamide (7-2)

This compound was made in an analogous way as was 7-1, substituting 4-1 as starting material. Data for 7-2: HRMS (ES) calc'd M+H for C$_{24}$H$_{26}$F$_3$N$_3$O: 430.2101. Found: 430.2119.

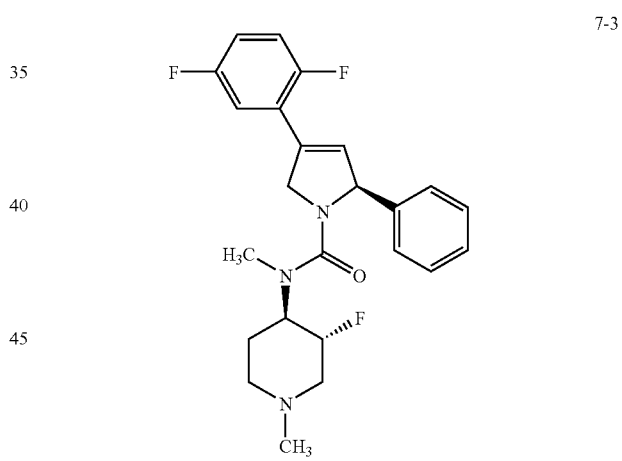

(2S)-4-(2,5-Difluorophenyl)-N-[(3R,4R)-3-fluoro-1-methylpiperidin-4-yl]-N-methyl-2-phenyl-2,5-dihydro-1H-pyrrole-1-carboxamide (7-3)

This compound was made in an analogous way as was 7-1, substituting 5-1 as starting material. Data for 7-3: HRMS (ES) calc'd M+H for C$_{24}$H$_{26}$F$_3$N$_3$O: 430.2101. Found: 430.2115. The absolute stereochemistry on the piperidine of compound 7-3 has not been determined and stereochemistry indicated has been tentatively assigned.

The following compounds are prepared by simple modifications of the procedures illustrated in Schemes 1-7 and Schemes G-N, but substituting the appropriately substituted reagents for those utilized in the Schemes.

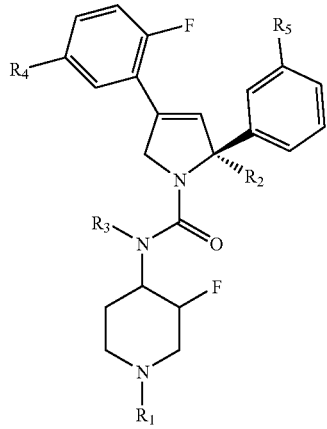
| R₁ | R₂ | R₃ | R₄ | R₅ |
|---|---|---|---|---|
| propyl | CH₂OH | Me | F | H |
| butyl | CH₂OH | Me | F | H |
| CH₂CH₂-phenyl | CH₂OH | Me | F | H |
| CH₂CH₂-(4-pyridyl) | CH₂OH | Me | F | H |
| CH₂CH₂-(3-pyridyl) | CH₂OH | Me | F | H |
| CH₂CH₂-(2-pyridyl) | CH₂OH | Me | F | H |
| CH₂CH₂-(5-pyrimidinyl) | CH₂OH | Me | F | H |
| CH₂CH₂-(2-pyrimidinyl) | CH₂OH | Me | F | H |
| CH₂CH₂-(2-pyrazinyl) | CH₂OH | Me | F | H |
| CH₂-phenyl | CH₂OH | Me | F | H |
| CH₂CH₂-(4-imidazolyl) | CH₂OH | Me | F | H |

-continued
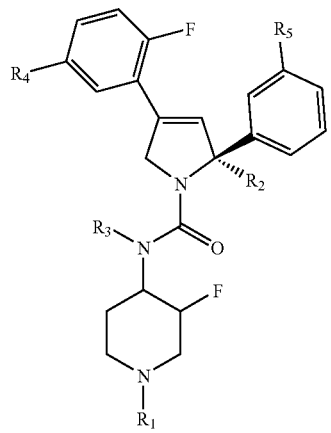
| R₁ | R₂ | R₃ | R₄ | R₅ |
|---|---|---|---|---|
| ethyl-pyrazole | CH₂OH | Me | F | H |
| ethyl-oxazole | CH₂OH | Me | F | H |
| ethyl-isoxazole | CH₂OH | Me | F | H |
| ethyl-thiazole | CH₂OH | Me | F | H |
| ethyl-(2-methyl)pyridine | CH₂OH | Me | F | H |
| ethyl-(2-methoxy)pyridine | CH₂OH | Me | F | H |
| ethyl-(6-methyl)pyridine | CH₂OH | Me | F | H |
| ethyl-(6-methoxy)pyridine | CH₂OH | Me | F | H |
| Me | Me | Me | F | H |
| Me | propyl | Me | F | H |
| Me | propyl-OH | Me | F | H |
| Me | CH(Ph)CH(NH₂)- | Me | F | H |

-continued
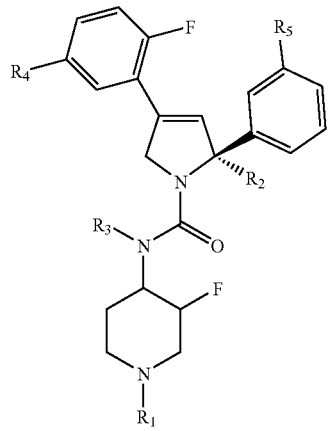
| R₁ | R₂ | R₃ | R₄ | R₅ |
|---|---|---|---|---|
| Me | ~~~OH | Me | F | H |
| Me | ~~~NH₂ | Me | F | H |
| Me | ~~(Ph)NH₂ | Me | F | H |
| Me | ~~~~OH | Me | F | H |
| Me | ~~~~NH₂ | Me | F | H |
| Me | ~~~(NH₂)(Ph) | Me | F | H |
| Me | ~(NH₂)(CHF₂) | Me | F | H |
| Me | ~~(CHF₂)(NH₂) | Me | F | H |
| Me | ~~~(NH₂)(CHF₂) | Me | F | H |
| Me | ~~~NHMe | Me | F | H |
| Me | ~~~NHPh | Me | F | H |
| Me | ~~~NHC(O)Me | Me | F | H |

-continued
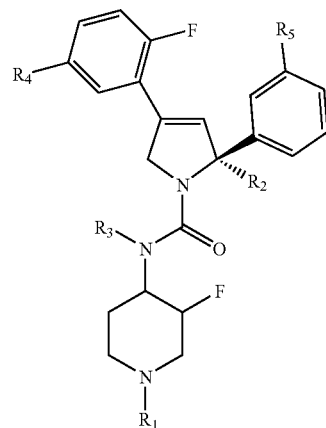
| R₁ | R₂ | R₃ | R₄ | R₅ |
|---|---|---|---|---|
| Me | butyl-NH-C(O)-OMe | Me | F | H |
| Me | butyl-NH-C(O)-NH₂ | Me | F | H |
| Me | butyl-pyrrole | Me | F | H |
| Me | propyl-pyrazole | Me | F | H |
| Me | propyl-isoxazole | Me | F | H |
| Me | propyl-imidazole | Me | F | H |
| Me | propyl-thiazole | Me | F | H |
| Me | CH₂OH | ethyl | F | H |
| Me | CH₂OH | propyl | F | H |
| Me | CH₂OH | isobutyl | F | H |

-continued
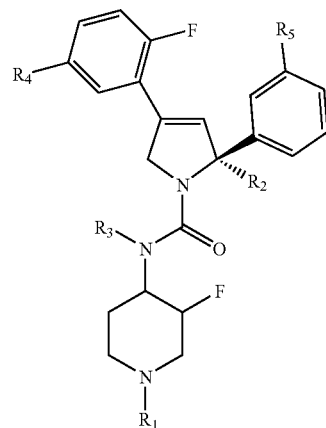
| R₁ | R₂ | R₃ | R₄ | R₅ |
|---|---|---|---|---|
| Me | CH₂OH |  | F | H |
| Me | CH₂OH | 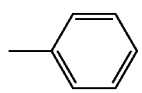 | F | H |
| Me | CH₂OH | 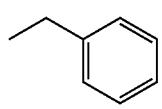 | F | H |
| Me | CH₂OH |  | F | H |
| Me | CH₂OH | 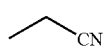 | F | H |
| Me | CH₂OH | 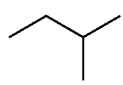 | F | H |
| Me | CH₂OH | 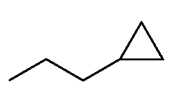 | F | H |
| Me | CH₂OH | Me | Cl | H |
| Me | CH₂OH | Me | Br | H |
| Me | CH₂OH | Me | CN | H |
| Me | CH₂OH | Me | Me | H |
| Me | CH₂OH | Me | CF₃ | H |
| Me | CH₂OH | Me | NO₂ | H |
| Me | CH₂OH | Me | F | OH |
| Me | CH₂OH | Me | F | NH₂ |
| Me | CH₂OH | Me | F | F |
| Me | CH₂OH | Me | F | SH |

SCHEME 8

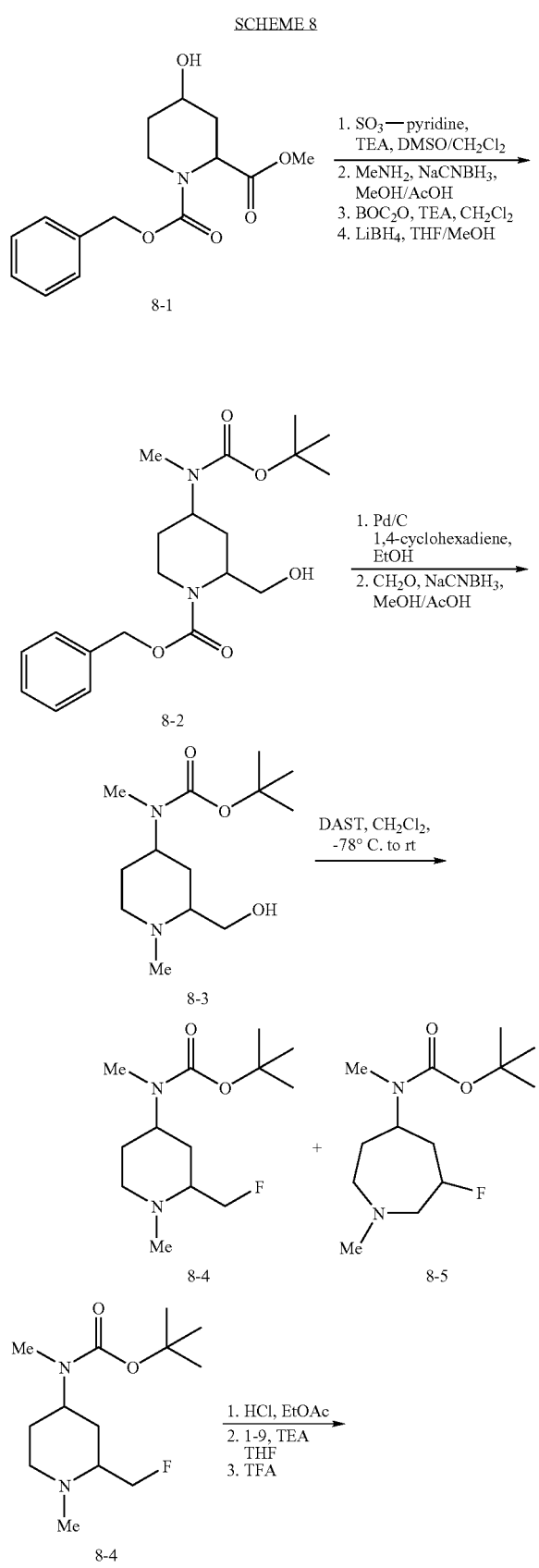

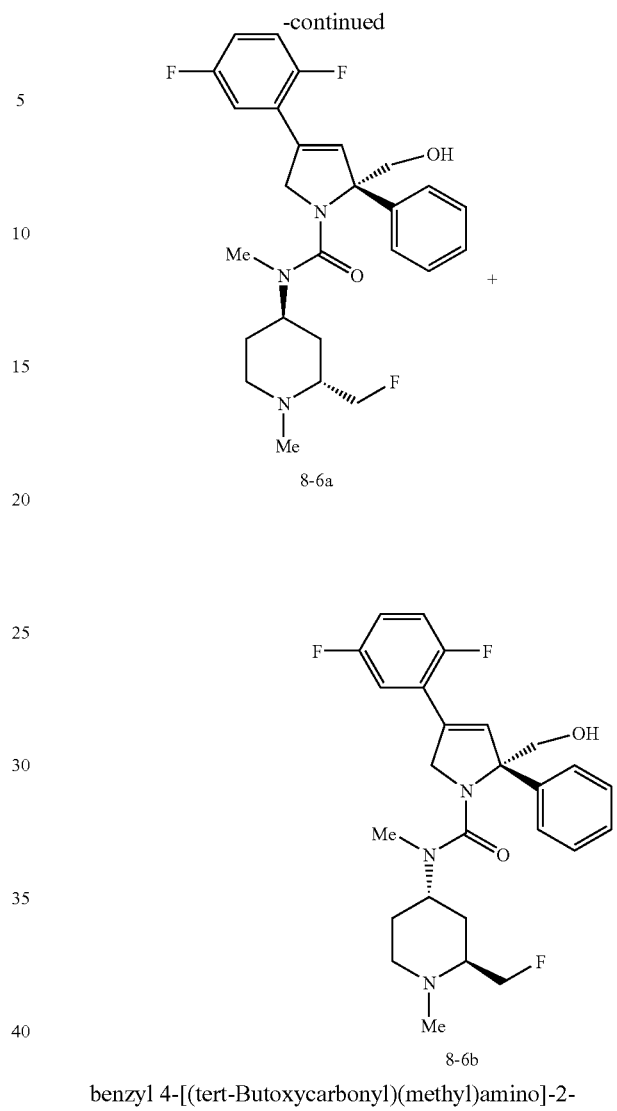

benzyl 4-[(tert-Butoxycarbonyl)(methyl)amino]-2-(hydroxymethyl)piperidine-1-carboxylate (8-2)

To a solution of 2.0 g (6.8 mmol) of 8-1 (reported in: S. J. Hayes, T. C. Malone, G. Johnson *J. Org. Chem.* 1991, 56, 4084-4086) in 100 mL of $CH_2Cl_2$ was added 3.33 mL (23.9 mmol) of triethylamine, followed by dropwise addition of 2.44 g (15.4 mmol) of $SO_3$-pyridine in 50 mL of DMSO. After stirring for 5 h at room temperature, the mixture was partitioned between $CH_2Cl_2$ and $H_2O$, the phases were separated, washed with 2×1M HCl, saturated aqueous $NaHCO_3$, brine, dried over $MgSO_4$, and concentrated to provide the ketone. To 2.1 g (7.2 mmol) of this ketone dissolved in 35 mL of MeOH was added 1 mL of AcOH and 14.4 mL (28.9 mmol) of a 2M solution of $MeNH_2$ in MeOH. After stirring for 1 h, 910 mg (14.4 mmol) of $NaCNBH_3$ in 5 mL of MeOH was added and the reaction was stirred overnight. The reaction was quenched with saturated aqueous $NH_4Cl$, extracted with $CH_2Cl_2$, washed with $NaHCO_3$, $H_2O$, brine, dried over $MgSO_4$, and concentrated to provide 2.0 g (7.2 mmol) of the amine. This material was dissolved in 25 mL of $CH_2Cl_2$, 1.78 g (8.2 mmol) of di-tert-butyl dicarbonate and 1.8 mL (12.9 mmol) of triethylamine were added, and the resultant mixture was stirred for 72 h. The reaction was then partitioned between $CH_2Cl_2$ and saturated aqueous $NaHCO_3$, separated, washed with $H_2O$, brine, dried over $MgSO_4$, and concentrated. The residue was purified by silica gel chromatography with EtOAc/hexanes to provide 1.85 g (4.6 mmol) of a mixture of diastereomers. This was dissolved in 20 mL of THF and 1 mL of MeOH, cooled to 0° C., and 496 mg (22.8 mmol) of LiBH$_4$ was added. After warming to room temperature and stirring overnight, the reaction was quenched with saturated aqueous NH$_4$Cl, extracted with EtOAc, washed with H$_2$O, brine, dried over MgSO$_4$, and concentrated to provide 8-2 as a colorless gum. Data for 8-2: LRMS (ES) calc'd M+H for C$_{20}$H$_{30}$N$_2$O$_5$: 379. Found: 379.

tert-Butyl [2-(hydroxymethyl)-1-methylpiperidin-4-yl]methylcarbamate (8-3)

To 1.08 g (2.9 mmol) of 8-2 in 30 mL of EtOH was added 7 mL (74 mmol) of 1,4-cyclohexadiene and a catalytic amount of 10% Pd on carbon. After stirring overnight, the reaction was filtered through Celite, concentrated by rotary evaporation, and dissolved in 25 mL of MeOH. To this was added 2 mL of AcOH, and 700 µL (8.6 mmol) of 37% aqueous formaldehyde. After stirring overnight, 540 mg (8.6 mmol) of NaCNBH$_3$ in 5 mL of MeOH was added and the reaction was stirred for 1 h more. The solvents were removed by rotary evaporation, the residue was partitioned between EtOAc and aqueous NaHCO$_3$, the organic phase was washed with brine, dried over Na$_2$SO$_4$, and concentrated: The residue was taken up in CH$_2$Cl$_2$, filtered and concentrated to provide 8-3 as a colorless oil. Data for 8-3: LRMS (ES) calc'd M+H for C$_{13}$H$_{26}$N2O$_3$: 259. Found: 259.

tert-Butyl [2-(fluoromethyl)-1-methylpiperidin-4-yl] methylcarbamate (8-4) and tert-butyl (6-fluoro-1-methylazepan-4-yl)methylcarbamate (8-5)

To a solution of 350 µL (2.6 mmol) of (diethylamino)sulfur trifluoride (DAST) in 15 mL of CH$_2$Cl$_2$ at −78° C. was added 520 mg (2.0 mmol) of 8-3 in 5 mL of CH$_2$Cl$_2$. The reaction was allowed to slowly warm to room temperature with stirring overnight, and was then quenched with ice water. The mixture was partitioned with additional CH$_2$Cl$_2$ and a small amount of 3M KOH, the organic phase was washed with water, dried over Na$_2$SO$_4$, and concentrated. The residue was loaded onto a silica gel column and eluted with EtOAc—20:1:1 EtOH/NH$_4$OH/H$_2$O. The first product to elute was the ring enlarged product 8-5 as a colorless oil, and the second to elute was 8-4 as a colorless oil. Both 8-5 and 8-4 were isolated as enantiomeric mixtures of the trans diastereomer. The structures were confirmed by extensive 1D and 2D NMR spectroscopy. Data for 8-5: $^1$HNMR (600 MHz, CD$_2$Cl$_2$) δ 4.75 (m, 1H), 4.1-3.9 (m, 1H), 2.9-2.7 (m, 3H), 2.75 (s, 3H), 2.4 (s, 3H), 2.35 (m, 1H), 2.1-1.7 (m, 4H), 1.4 (s, 9H) ppm. Data for 8-4: $^1$HNMR (500 MHz, CD$_2$Cl$_2$) δ 4.8-4.5 (m, 2H), 4.1-4.0 (m, 1H), 3.2 (m, 1H), 2.75 (m, 2H), 2.7 (s, 3H), 2.45 (s, 3H), 1.9-1.5 (m, 4H), 1.45 (s, 9H) ppm.

(2S)-4-(2,5-Difluorophenyl)-N-[(2R,4R)-2-(fluoromethyl)-1-methylpiperidin-4-yl]-2-(hydroxymethyl)-N-methyl-2-phenyl-2,5-dihydro-1H-pyrrole-1-carboxamide (8-6a) and (2S)-4-(2,5-Difluorophenyl)-N-[(2S,4S)-2-(fluoromethyl)-1-methylpiperidin-4-yl]-2-(hydroxymethyl)-N-methyl-2-phenyl-2,5-dihydro-1H-pyrrole-1-carboxamide (8-6b)

A solution of 80 mg (0.31 mmol) of 8-4 in 30 mL of EtOAc was saturated with HCl gas and allowed to stir 1 h at room temperature. The reaction was then concentrated by rotary evaporation and the resulting white solid was suspended in 1 mL of THF. To this was added 156 mg (0.34 mmol) of 1-9, 268 µL (1.54 mmol) of diisopropylethylamine and a catalytic amount of DMAP. After heating at 50° C. overnight, 500 µL of trifluoroacetic acid was added and stirring was continued an additional 1 h at room temperature before being quenched with saturated aqueous NaHCO$_3$. The mixture was partitioned with CH$_2$Cl$_2$, the organic phase was washed with brine, dried over MgSO$_4$, and concentrated. The residue was loaded onto a silica gel column and eluted with CHCl$_3$—80:10:10 CHCl$_3$/EtOAc/MeOH to provide 8-6a and 8-6b as an inseparable mixture—a colorless gum. Data for 8-6a/8-6b: HRMS (ES) calc'd M+H for C$_{26}$H$_{30}$F$_3$N$_3$O$_2$: 474.2363. Found: 474.2374.

The following compounds are prepared by simple modifications of the procedures illustrated in Schemes 1-8 and Schemes G-N, but substituting the appropriately substituted reagents for those utilized in the Schemes.

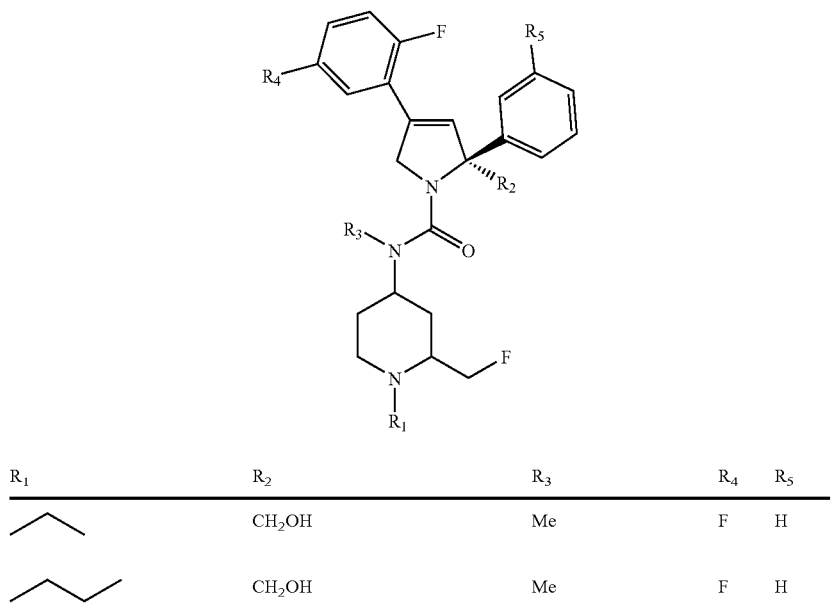

| R$_1$ | R$_2$ | R$_3$ | R$_4$ | R$_5$ |
|---|---|---|---|---|
| ∧ | CH$_2$OH | Me | F | H |
| ∧/ | CH$_2$OH | Me | F | H |

-continued
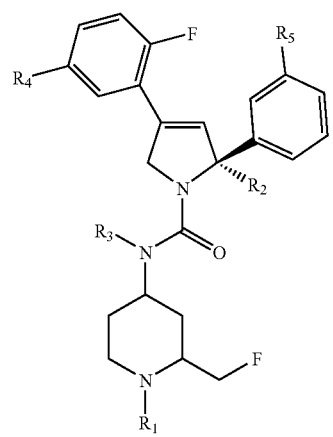
| R₁ | R₂ | R₃ | R₄ | R₅ |
|---|---|---|---|---|
| 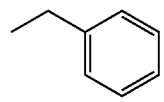 | CH₂OH | Me | F | H |
| 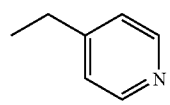 | CH₂OH | Me | F | H |
| 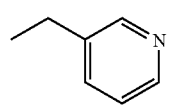 | CH₂OH | Me | F | H |
| 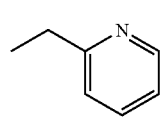 | CH₂OH | Me | F | H |
| 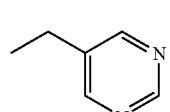 | CH₂OH | Me | F | H |
| 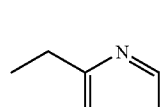 | CH₂OH | Me | F | H |
| 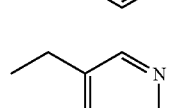 | CH₂OH | Me | F | H |
| 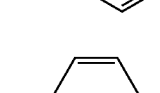 | CH₂OH | Me | F | H |
| 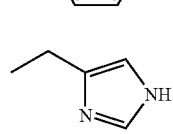 | CH₂OH | Me | F | H |

-continued
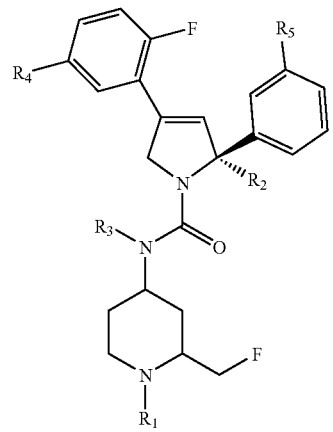
| R₁ | R₂ | R₃ | R₄ | R₅ |
|---|---|---|---|---|
| 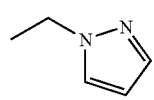 | CH₂OH | Me | F | H |
| 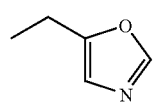 | CH₂OH | Me | F | H |
| 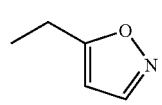 | CH₂OH | Me | F | H |
| 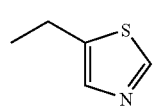 | CH₂OH | Me | F | H |
| 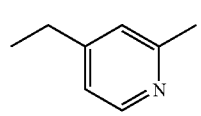 | CH₂OH | Me | F | H |
| 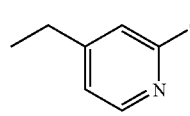 | CH₂OH | Me | F | H |
| 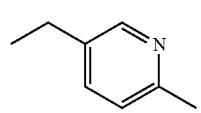 | CH₂OH | Me | F | H |
| 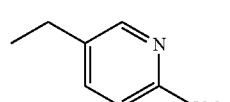 | CH₂OH | Me | F | H |
| Me | Me | Me | F | H |

-continued
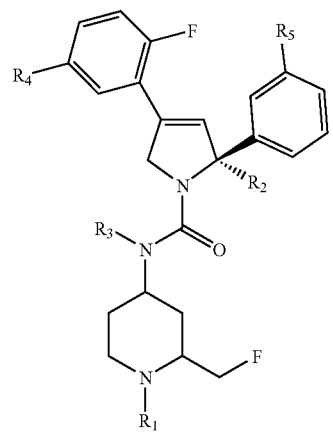
| R₁ | R₂ | R₃ | R₄ | R₅ |
|---|---|---|---|---|
| Me | propyl | Me | F | H |
| Me | CH₂CH₂CH₂OH | Me | F | H |
| Me | CH₂CH(Ph)NH₂ | Me | F | H |
| Me | (CH₂)₃OH | Me | F | H |
| Me | (CH₂)₃NH₂ | Me | F | H |
| Me | CH₂CH₂CH(Ph)NH₂ | Me | F | H |
| Me | (CH₂)₄OH | Me | F | H |
| Me | (CH₂)₄NH₂ | Me | F | H |
| Me | (CH₂)₃CH(Ph)NH₂ | Me | F | H |
| Me | CH₂CH(NH₂)CH₂CHF₂ | Me | F | H |
| Me | CH₂CH₂CH(NH₂)CH₂F... (CHF₂ branch) | Me | F | H |
| Me | (CH₂)₃CH(NH₂)CH₂F (CHF₂) | Me | F | H |
| Me | (CH₂)₃NHMe | Me | F | H |

-continued
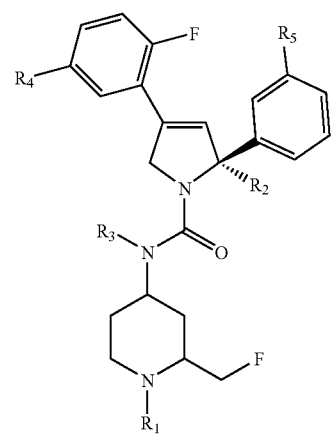
| R₁ | R₂ | R₃ | R₄ | R₅ |
|---|---|---|---|---|
| Me | 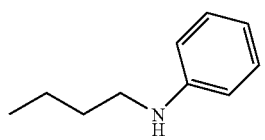 | Me | F | H |
| Me | 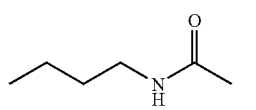 | Me | F | H |
| Me | 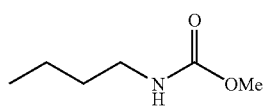 | Me | F | H |
| Me | 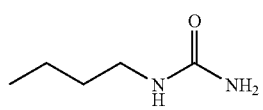 | Me | F | H |
| Me | 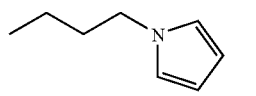 | Me | F | H |
| Me | 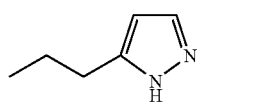 | Me | F | H |
| Me | 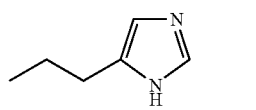 | Me | F | H |
| Me | 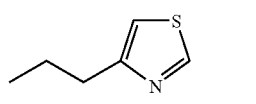 | Me | F | H |
| Me |  | Me | F | H |

-continued

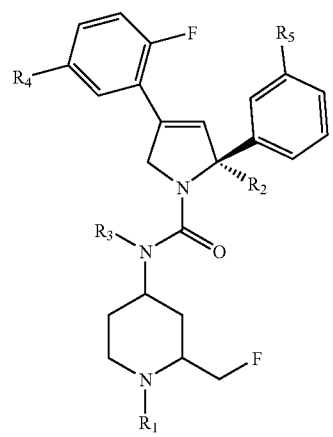

| R₁ | R₂ | R₃ | R₄ | R₅ |
|---|---|---|---|---|
| Me | CH₂OH | ethyl | F | H |
| Me | CH₂OH | propyl | F | H |
| Me | CH₂OH | isobutyl | F | H |
| Me | CH₂OH | cyclopropylmethyl | F | H |
| Me | CH₂OH | benzyl | F | H |
| Me | CH₂OH | phenethyl | F | H |
| Me | CH₂OH | cyclobutylmethyl | F | H |
| Me | CH₂OH | CH₂CH₂CN | F | H |
| Me | CH₂OH | sec-butyl | F | H |
| Me | CH₂OH | cyclopropylethyl | F | H |
| Me | CH₂OH | Me | Cl | H |
| Me | CH₂OH | Me | Br | H |
| Me | CH₂OH | Me | CN | H |
| Me | CH₂OH | Me | Me | H |
| Me | CH₂OH | Me | CF₃ | H |
| Me | CH₂OH | Me | NO₂ | H |
| Me | CH₂OH | Me | F | OH |
| Me | CH₂OH | Me | F | NH₂ |
| Me | CH₂OH | Me | F | F |
| Me | CH₂OH | Me | F | SH |

SCHEME 9

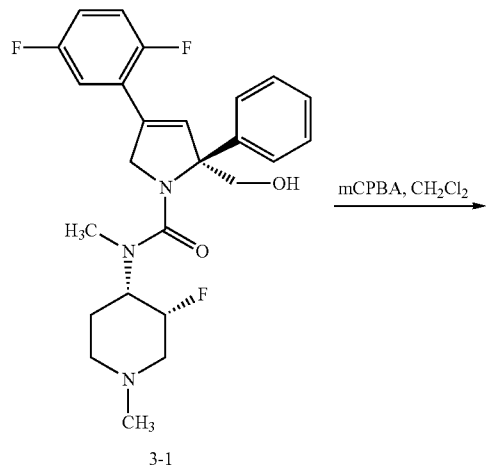

SCHEME 10

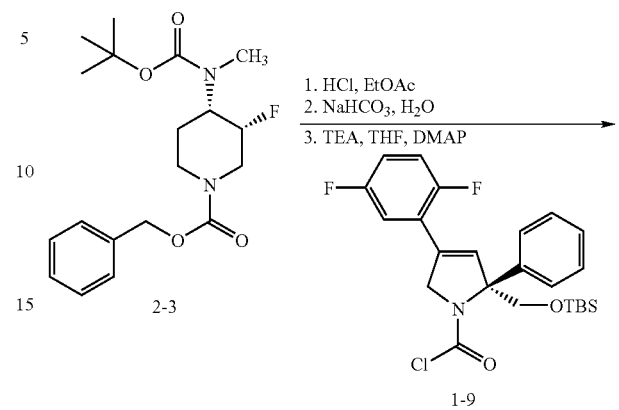

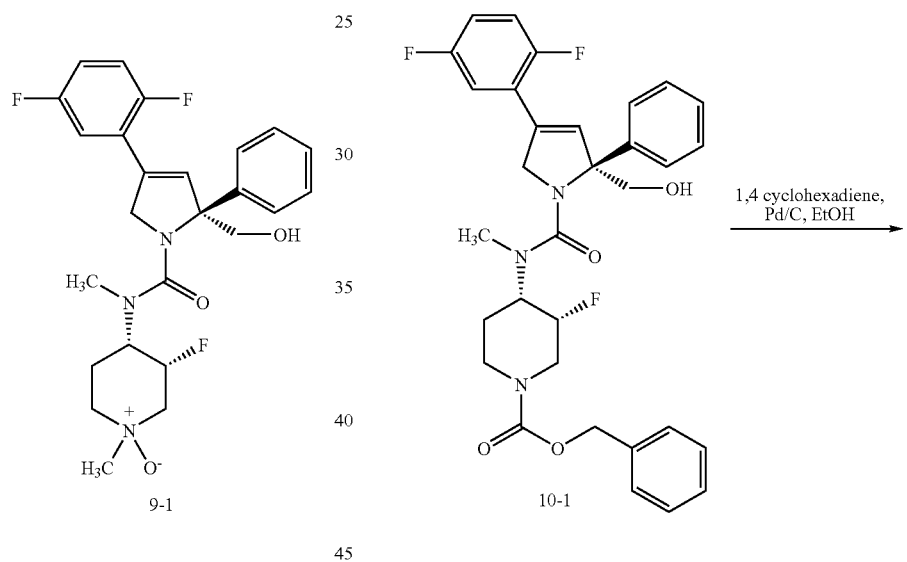

(2S)-4-(2,5-Difluorophenyl)-N-[(3R,4S)-3-fluoro-1-methyl-1-oxidopiperidin-4-yl]-2-(hydroxymethyl)-N-methyl-2-phenyl-2,5-dihydro-1H-pyrrole-1-carboxamide (9-1)

To a solution of 20 mg (0.044 mmol) of 3-1 in 1 mL of CH$_2$Cl$_2$ at 0° C. was added 11 g (~0.048 mmol) of mCPBA. The ice-bath was removed and the reaction was stirred for 30 min. The mixture was partitioned with EtOAc and saturated aqueous NaHCO$_3$, separated, washed with H$_2$O, brine, dried over Na$_2$SO$_4$ and concentrated by rotary evaporation. The residue was loaded onto a silica gel column and eluted with EtOAc—20:1:1 EtOH/NH$_4$OH/H$_2$O to provide 9-1 as a white foam. Data for 9-1: $^1$HNMR (500 MHz, CDCl$_3$) δ 7.4-7.2 (m, 5H), 7.1-6.9 (nm, 3H), 6.25 (s, 1H), 5.0-4.9 (m, 2H), 4.7. (m, 1H), 4.5 (m, 1H), 4.3-4.2 (m, 1H), 4.0 (m, 2H), 3.7 (m, 1H), 3.4-3.3 (m, 2H), 3.3 (s, 3H), 3.2 (s, 3H), 2.5-1.9 (bs, 2H), 1.8 (m, 1H) ppm. HRMS (ES) calc'd M+H for C$_{25}$H$_{28}$F$_3$N$_3$O$_3$: 476.2156. Found: 476.2165.

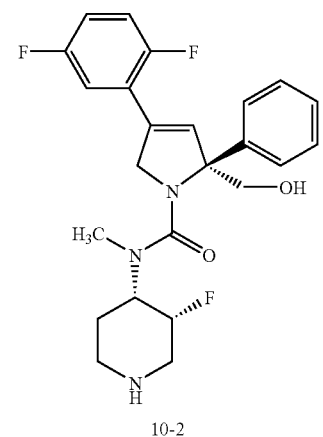

Step 1: Benzyl (3R,4S)-4-[{[(2S)-4-(2,5-difluorophenyl)-2-(hydroxymethyl)-2-phenyl-2,5-dihydro-1H-pyrrol-1-yl]carbonyl}(methyl)amino]-3-fluoropiperidine-1-carboxylate (10-1):

To a solution of 885 mg (2.4 mmol) of 2-3 (first isomer to elute from the chromnatography) in 12 mL of EtOAc at 0° C. was added 12 mL (48 mmol) of a 4M solution of HCl in dioxane. The ice-bath was removed, stirring was continued for 2 h, and then the volitiles were removed by rotary evaporation. The residue was partitioned between EtOAc and saturated aqueoeus $NaHCO_3$ with 5 mL of 1M NaOH, separated, and the aqueous phase extracted 2×EtOAc. The combined organic extracts were washed again with $NaHCO_3$, brine, dried over $Na_2SO_4$, and concentrated to provide 590 mg (2.2 mmol) of the amine. To 215 mg (0.81 mmol) of this material in 5 mL of THF was added 340 mg (0.73 mmol) of 1-9, 306 μL (2.2 mmol) of triethylamine, and a catalytic amount of DMAP. After stirring overnight, the reaction was judged only ~40% complete by LC/MS, so an additional portion of DMAP was added and stirring was continued overnight. The reaction was then partitioned between EtOAc and saturated aqueous $NaHCO_3$, the organic phase was washed with $NaHCO_3$, $H_2O$, brine, dried over $Na_2SO_4$, and concentrated. The residue was purified by silica gel chromatography with EtOAc/hexanes to provide 10-1 as a colorless oil. Data for 10-1: LRMS (ES) calc'd M+H for $C_{38}H_{46}F_3N_3O_4Si$: 694.4. Found: 694.3.

Step 2: (2S)-4-(2,5-Difluorophenyl)-N-[(3R,4S)-3-fluoropiperidin-4-yl]-2-(hydroxymethyl)-N-methyl-2-phenyl-2,5-dihydro-1H-pyrrole-1-carboxamide (10-2):

To a solution of 405 mg (0.58 mmol) of 10-1 in 4 mL of EtOH was added 1.38 mL (14.6 mmol) of 1,4-cyclohexadiene, 100 mg of 10% palladium on carbon, and then stirred overnight. The reaction was filtered through Celite, concentrated, and the residue was dissolved in 3 mL of $CH_2Cl_2$. To this was added 3 mL of trifluoroacetic acid, stirring was maintained for 1 h, and then the mixture was partitioned between EtOAc and saturated aqueous $NaHCO_3$ plus 25 mL of 5% aqueous $Na_2CO_3$, the organic phase was washed with $NaHCO_3$ again, $H_2O$, brine, dried over $Na_2SO_4$, and concentrated by rotary evaporation. The residue was loaded onto a silica gel column and eluted with EtOAc—20:1:1 EtOH/$NH_4OH/H_2O$ to provide 10-2 as a white solid. There was an impurity of 5% subsequently removed by reverse phase chromatography with 95:5 to 5:95 $H_2O/CH_3CN$ (both with 0.1% TFA). The fractions were basified with $NaHCO_3$ to provide pure B-2 as a white solid. Data for 10-2: $^1$HNMR (500 MHz, $CDCl_3$) δ 7.4-7.2 (m, 5H), 7.1-6.9 (mn, 3H), 6.3 (s, 1H), 5.2 (bs, 1H), 4.9 (m, 1H), 4.8-4.6 (m, 2H), 4.45 (m, 1H), 4.2-4.1 (m, 1H), 4.0 (m, 1H), 3.3-3.2 (mn, 2H), 3.1 (s, 3H), 2.85-2.7 (m, 2H), 2.1 (m, 1H), 1.7 (m, 2H) ppm. HRMS (ES) calc'd M+H for $C_{24}H_{26}F_3N_3O_2$: 446.2050. Found: 446.2059.

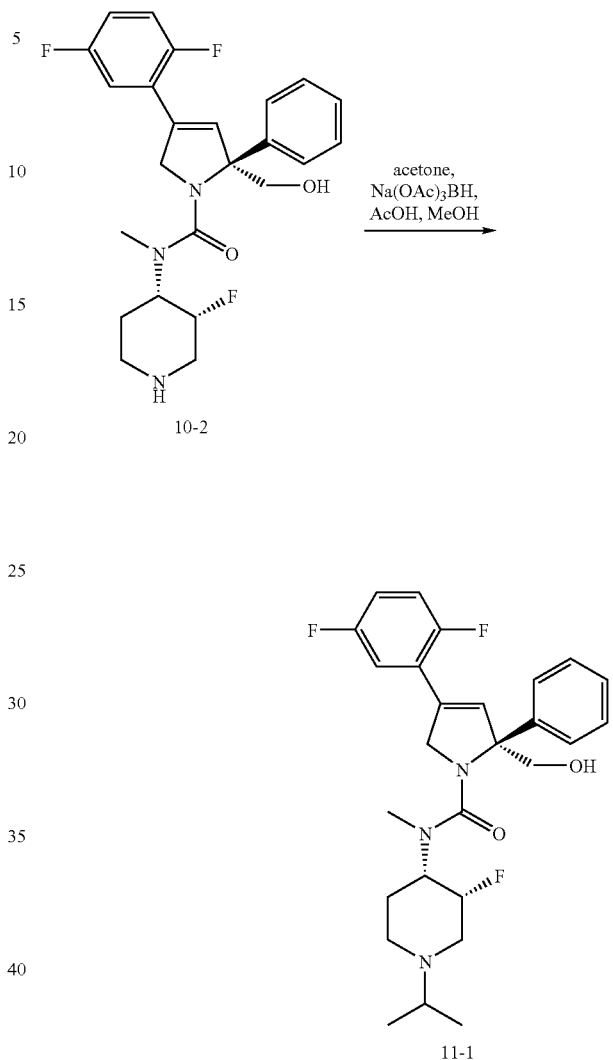

SCHEME 11

(2S)-4-(2,5-Difluorophenyl)-N-[(3R,4S)-3-fluoro-1-isopropylpiperidin-4-yl]-2-(hydroxymethyl)-N-methyl-2-phenyl-2,5-dihydro-1H-pyrrole-1-carboxamide (11-1)

To a solution of 38 mg (0.085 mmol) of 10-2 in 1 mL of 1,2-dichloroethane was added 20 μL (0.34 mmol) of acetic acid, 25 μL (0.34 mmol) of acetone, and 27 mg (0.13 mmol) of $Na(OAc)_3BH$. After stirring overnight, the reaction was partitioned between EtOAc and saturated aqueous $NaHCO_3$, the organic phase was washed again with $NaHCO_3$, $H_2O$, brine, dried over $Na_2SO_4$, and concentrated by rotary evaporation. The residue was purified by reverse phase chromatography with 95:5 to 5:95 $H_2O/CH_3CN$ (both with 0.1% TFA). The fractions were basified with $NaHCO_3$ to provide 11-1 as a colorless film. Data for 11-1: $^1$HNMR (500 MHz, $CDCl_3$) δ 7.4-7.2 (m, 5H), 7.1-6.9 (m, 3H), 6.3 (s, 1H), 5.3 (m, 1H), 4.95-4.8 (m, 2H), 4.6 (m, 1H), 4.45 (m, 1H), 4.1-4.0 (m, 2H), 3.2 (m, 1H), 3.15 (s, 3H), 3.0 (m, 1H), 2.8 (m, 1H), 2.45-2.25 (m, 3H), 1.75 (m, 1H), 1.1-1.0 (m, 6H) ppm. HRMS (ES) calc'd M+H for $C_{27}H_{32}F_3N_3O_2$: 488.2519. Found: 488.2517.

SCHEME 12

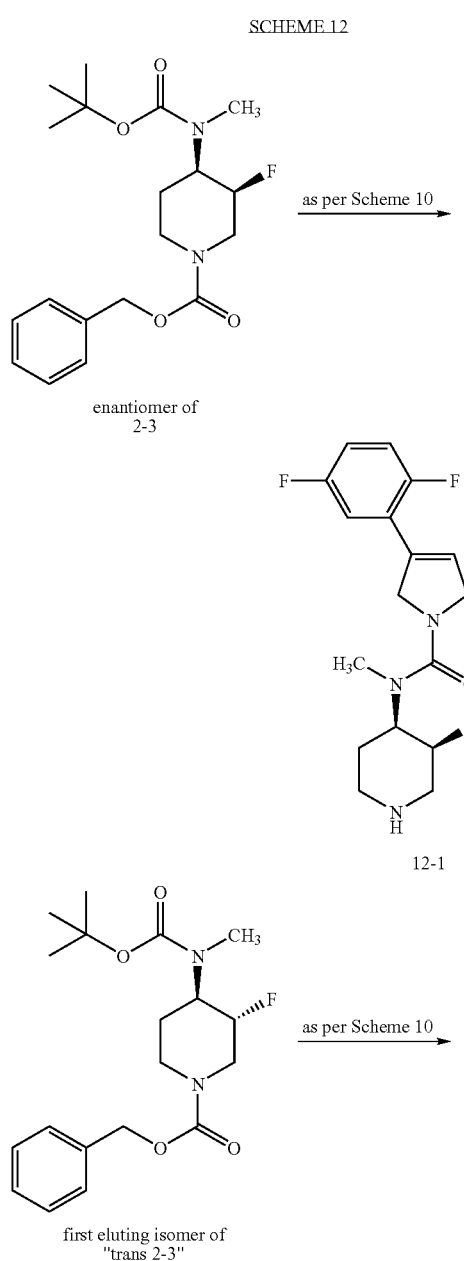

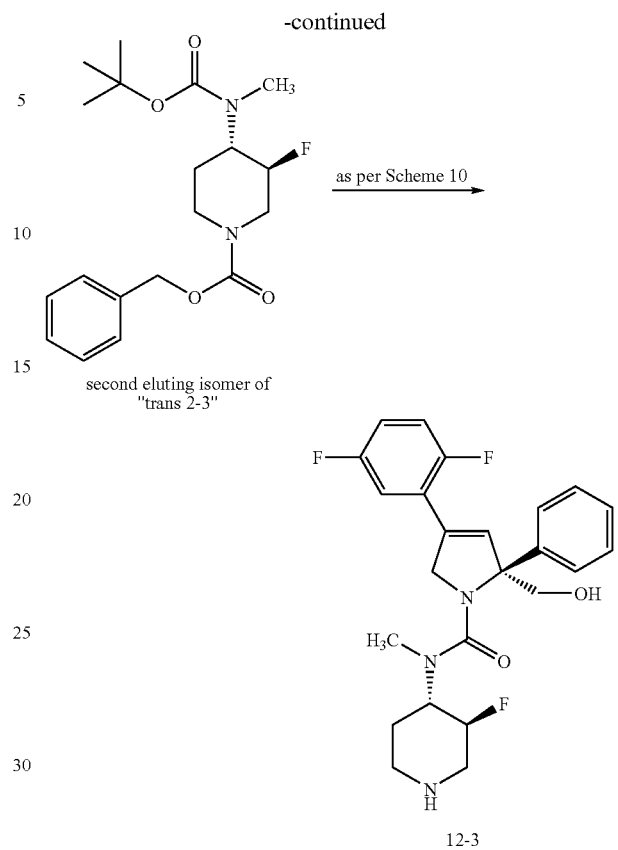

(2S)-4-(2,5-Difluorophenyl)-N-[(3S,4R)-3-fluoropiperidin-4-yl]-2-(hydroxymethyl)-N-methyl-2-phenyl-2,5-dihydro-1H-pyrrole-1-carboxamnide (12-1)

This compound was made in a manner identical to that for 10-2, with the exception of incorporation of the enantiomer of 2-3. Data for 12-1: HRMS (ES) calc'd M+H for $C_{24}H_{26}F_3N_3O_2$: 446.2050. Found: 446.2069.

(2S)-4-(2,5-Difluorophenyl)-N-[(3R,4R)-3-fluoropiperidin-4-yl]-2-(hydroxymethyl)-N-methyl-2-phenyl-2,5-dihydro-1H-pyrrole-1-carboxamide (12-2)

This compound was made in a manner identical to that for 10-2, with the exception that the trans isomer of 2-2a was incorporated into the synthesis. Resolution of the enantiomers of "trans-2-3" was carried out chromatographically using a Chiralpak AD© 10×50 cm column with 15% EtOH in hexanes (with 0.1% diethylamine) at 150 mL/min. Analytical HPLC analysis of the eluent on a 4×250 mM Chiralpak AD® column with 15% EtOH in hexanes (with 0.1% diethylamine) at 1 mL/min indicated that first eluting enantiomer has $R_t$=7.30 min and the second enantiomer has $R_t$=11.59 min. The first eluting enantiomer (having unknown absolute stereochemistry) was further processed to provide the trans amine, which was incorporated into the synthesis of 12-2 following a route identical to that explained in Scheme 10. Data for 12-2: HRMS (ES) calc'd M+H for $C_{24}H_{26}F_3N_3O_2$: 446.2050. Found: 446.2069. The absolute stereochemistry on the piperidine of compounds 12-2 and 12-3 has not ben determined and stereochemistry indicated has been tentatively assigned.

(2S)-4-(2,5-Difluorophenyl)-N-[(3S,4S)-3-fluoropiperidin-4-yl]-2-(hydroxymethyl)-N-methyl-2-phenyl-2,5-dihydro-1H-pyrrole-1-carboxamide (12-3)

This compound was made in a manner identical to that for 10-2, with the exception of incorporation of the second eluting isomer of "trans-2-3" from the chiral column. Data for 12-3: HRMS (ES) calc'd M+H for $C_{24}H_{26}F_3N_3O_2$: 446.2050. Found: 446.2068.

---

---

What is claimed is:

1. The compound of Formula II:

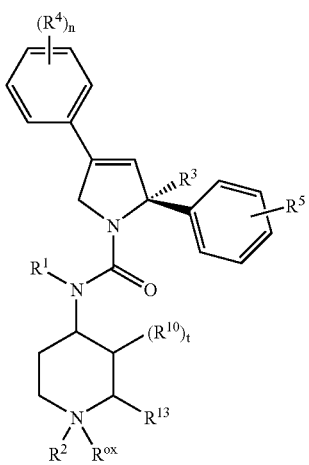

II or a pharmaceutically acceptable salt or stereoisomer thereof,
wherein:
b is 0 or 1;
m is 0, 1, or 2;
n is 0, 1, 2 or 3;
r is 0 or 1;
s is 0 or 1;
t is 0 or 1;
$R^1$ and $R^2$ are independently selected from: H or $(C_1$-$C_6)$ alkyl, optionally substituted with one, two or three substituents selected from R7;
$R^3$ is selected from:
  1) hydrogen; or
  3) $CH_2$—O—$R^d$,
$R^4$ is independently selected from:
  1) halo,
  2) OH, and
  3) $O_bC_1$-$C_6$ perfluoroalkyl;
$R^5$ is selected from:
  1) hydrogen and
  2) halo,
$R^7$ is selected from:
  1) (C=O)$_r$O$_s$($C_1$-$C_{10}$)alkyl,
  2) O$_r$($C_1$-$C_3$)perfluoroalkyl,
  3) oxo,
  4) OH,
  5) halo,
  6) CN,
  7) $(C_2$-$C_{10})$alkenyl,
  8) $(C_2$-$C_{10})$alkynyl,
  13) C(O)$R^a$,
  14) $(C_0$-$C_6)$alkylene-CO$_2R^a$,
  15) C(O)H,
  16) $(C_0$-$C_6)$alkylene-CO$_2$H,
  17) C(O)N($R^b$)$_2$,
  18) S(O)$_mR^a$,
  19) S(O)$_2$N($R^b$)$_2$; and
  20) —OPO(OH)$_2$;
said alkyl, alkenyl, alkynyl, and alkylene is optionally substituted with up to three substituents selected from $R^b$, OH, $(C_1$-$C_6)$alkoxy, halogen, CO$_2$H, CN, O(C=O)$C_1$-$C_6$ alkyl, oxo, NO$_2$ and N($R^b$)$_2$;

$R^{10}$ is selected from: F and —$CH_2F$;
$R^{13}$ is selected from: H and $CH_2F$, provided that if t is 1, $R^{13}$ is H, and if t is 0, $R^{13}$ is —$CH_2F$;
$R^{ox}$ is absent or is oxo;
$R^a$ is ($C_1$-$C_6$)alkyl;
$R^b$ H or ($C_1$-$C_6$)alkyl;
$R^d$ is selected from: H or (C1-C6)alkyl.

2. The compound according to claim 1 of the Formula III:

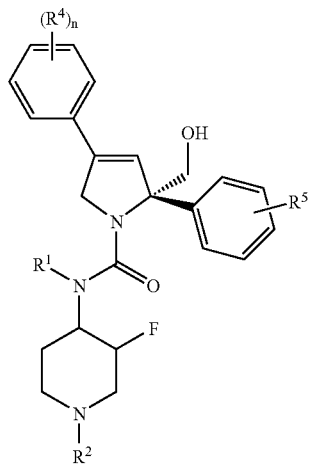

III or a pharmaceutically acceptable salt or stereoisomer thereof, wherein:
b is 0 or 1;
m is 0, 1, or 2;
n is 0, 1 or 2;
r is 0 or 1;
s is 0 or 1;
$R^1$ and $R^2$ are independently selected from: H or ($C_1$-$C_6$) alkyl, optionally substituted with one, two or three substituents selected from $R^7$;
$R^4$ is independently selected from:
  1) halo,
  2) OH,
  3) $O_bC_1$-$C_6$ perfluoroalkyl,
$R^5$ is selected from:
  1) hydrogen, or
  2) halo,
$R^7$ is selected from:
  1) (C=O)$_r$O$_s$($C_1$-$C_{10}$)alkyl,
  2) O$_r$($C_1$-$C_3$)perfluoroalkyl,
  3) oxo,
  4) OH,
  5) halo,
  6) CN,
  7) ($C_2$-$C_{10}$)alkenyl,
  8) ($C_2$-$C_{10}$)alkynyl,
  13) C(O)$R^a$,
  14) ($C_0$-$C_6$)alkylene-CO$_2R^a$,
  15) C(O)H,
  16) ($C_0$-$C_6$)alkylene-CO$_2$H, and
  17) C(O)N($R^b$)$_2$,
  18) S(O)$_m R^a$, and
  19) S(O)$_2$N($R^b$)$_2$;
said alkyl, alkenyl, alkynyl and alkylene are optionally substituted with up to three substituents selected from $R^b$, OH, ($C_1$-$C_6$)alkoxy, halogen, CO$_2$H, CN, O(C=O)$C_1$-$C_6$ alkyl, oxo, NO$_2$ and N($R^b$)$_2$;

$R^a$ is independently selected from: ($C_1$-$C_6$)alkyl;
$R^b$ is H or ($C_1$-$C_6$)alkyl.

3. The compound according to claim 2 of the Formula IV:

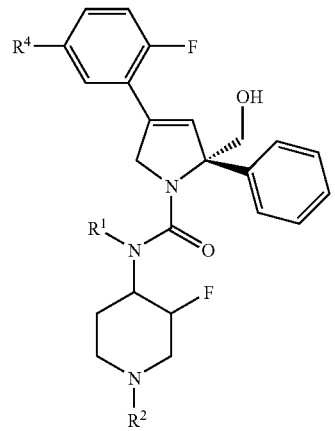

IV or a pharmaceutically acceptable salt or stereoisomer thereof, wherein:
b is
m is 0, 1, or 2;
r is 0 or 1;
s is 0 or 1;
$R^1$ and $R^2$ are independently selected from: H and ($C_1$-$C_6$) alkyl, optionally substituted with one, two or three substituents selected from $R^7$;
$R^4$ is independently selected from:
  1) halo,
  2) OH,
  3) $O_bC_1$-$C_6$ perfluoroalkyl,
R7 is selected from:
  1) (C=O)$_r$O$_s$($C_1$-$C_{10}$)alkyl,
  2) O$_r$($C_1$-$C_3$)perfluoroalkyl,
  3) oxo,
  4) OH,
  5) halo,
  6) CN,
  7) ($C_2$-$C_{10}$)alkenyl,
  8) ($C_2$-$C_{10}$)alkynyl,
  13) C(O)$R^a$,
  14) ($C_0$-$C_6$)alkylene-CO$_2R^a$,
  15) C(O)H,
  16) ($C_0$-$C_6$)alkylene-CO$_2$H, and
  17) C(O)N($R^b$)$_2$,
  18) S(O)$_m R^a$, and
  19) S(O)$_2$N($R^b$)$_2$;
said alkyl, alkenyl, alkynyl, and alkylene is optionally substituted with up to three substituents selected from $R^b$, OH, ($C_1$-$C_6$)alkoxy, halogen, CO$_2$H, CN, O(C=O)$C_1$-$C_6$ alkyl, oxo, NO$_2$ and N($R^b$)$_2$;
$R^a$ is ($C_1$-$C_6$)alkyl;
$R^b$ is H or ($C_1$-$C_6$)alkyl.

4. The compound according to claim 3 of the Formula V:

V

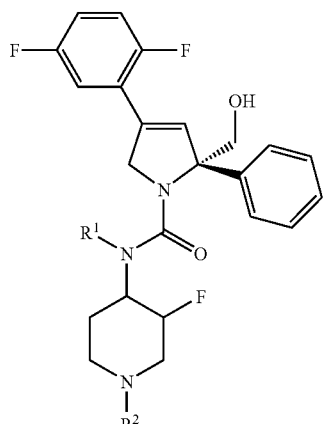

or a pharmaceutically acceptable salt or stereoisomer thereof, wherein:
R$^1$ and R$^2$ are independently selected from: H and (C$_1$-C$_6$) alkyl.

5. The compound according to claim 1 of the formula VI:

VI

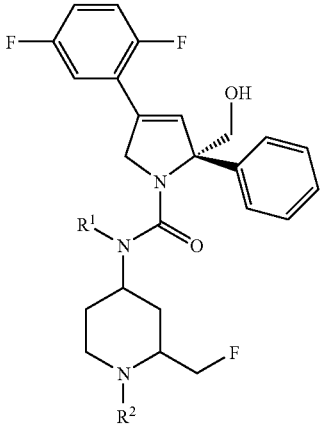

or a pharmaceutically acceptable salt or stereoisomer thereof, wherein:
R$^1$ and R$^2$ are independently selected from: H and (C$_1$-C$_6$) alkyl.

6. A compound according to claim 1 selected from:
(2S)-4-(2,5-Difluorophenyl)-N-[(3S,4R)-3-fluoro-1-methylpiperidin-4-yf]-2-(hydroxymethyl)-N-methyl-2-phenyl-2,5-dihydro-1H-pyrrole-1-carboxamide
(2S)-4-(2,5-Difluorophenyl)-N-[(3R,4S)-3-fluoro-1-methylpiperidin-4-yl]-2-(hydroxymethyl)-N-methyl-2-phenyl-2,5-dihydro-1H-pyrrole-1-carboxamide
(2S)-4-(2,5-Difluorophenyl)-N-[(3R,4R)-3-fluoro-1-methylpiperidin-4-yl]-2-(hydroxymethyl)-N-methyl-2-phenyl-2,5-dihydro-1H-pyrrole-1-carboxamide
(2S)-4-(2,5-Difluorophenyl)-N-[(3S,4S)-3-fluoro-1-methylpiperidin-4-yl]-2-(hydroxymethyl)-N-methyl-2-phenyl-2,5-dihydro-1H-pyrrole-1-carboxamide
(2S)-4-(2,5-Difluorophenyl)-N-[(3S,4R)-3-fluoro-1-methylpiperidin-4-yl]-N-methyl-2-phenyl-2,5-dihydro-1H-pyrrole-1-carboxamide
(2S)-4-(2,5-Difluorophenyl)-N-[(3R,4S)-3-fluoro-1-methylpiperidin-4-yl]-N-methyl-2-phenyl-2,5-dihydro-1H-pyrrole-1-carboxamide
(2S)-4-(2,5-Difluorophenyl)-N-[(3R,4R)-3-fluoro-1-methylpiperidin-4-yl]-N-methyl-2-phenyl-2,5-dihydro-1H-pyrrole-1-carboxamide
(2S)-4-(2,5-Difluorophenyl)-N-[(2R,4R)-2-(fluoromethyl)-1-methylpiperidin-4-yl]-2-(hydromethyl)-N-methyl-2-phenyl-2,5-dihydro-1H-pyrrole-1-carboxamide
(2S)-4-(2,5-Difluorophenyl)-N-[(2S,4S)-2-(fluoromethyl)-1-methylpiperidin-4-yl]-2-(hydroxymethyl)-N-methyl-2-phenyl-2,5-dihydro-1H-pyrrole-1-carboxamide
(2S)-4-(2,5-Difluorophenyl)-N-[(3S,4R)-3-fluoro-1-methyl-1-oxidopiperidin-4-yl]-2-(hydroxymethyl)-N-methyl-2-phenyl-2,5-dihydro-1H-pyrrole-1-carboxamide
(2S)-4-(2,5-Difluorophenyl)-N-[(3S,4R)-3-fluoropiperidin-4-yl]-2-(hydroxymethyl)-N-methyl-2-phenyl-2,5-dihydro-1H-pyrrole-1-carboxamide
(2S)-4-(2,5-Difluorophenyl)-N-[(3S,4R)-3-fluoro-1-isopropylpiperidin-4-yl]-2-(hydroxymethyl)-N-methyl-2-phenyl-2,5-dihydro-1H-pyrrole-1-carboxamide
(2S)-4-(2,5-Difluorophenyl)-N-[(3S,4S)-3-fluoropiperidin-4-yl]-2-(hydroxymethyl)-N-methyl-2-methyl-2,5-dihydro-1H-pyrrole-1-carboxamide or a pharmaceutically acceptable salt thereof.

7. The compound of claim 1 which is:

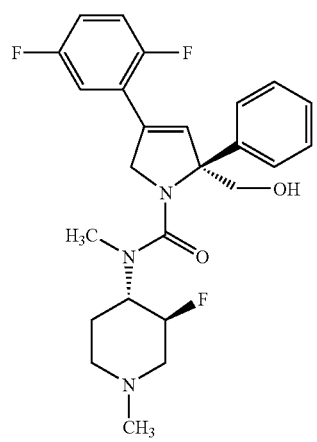

(2S)-4-(2,5-Difluorophenyl)-N-[(3S,4S)-3-fluoro-1-methylpiperidin-4-yl]-2-(hydroxymethyl)-N-methyl-2-phenyl-2,5-dihydro-1H-pyrrole-1-carboxamide
or a pharmaceutically acceptable salt thereof.

8. The compound of claim 1 which is:

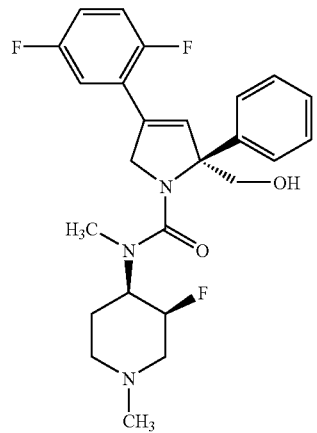

(2S)-4-(2,5-Difluorophenyl)-N-[(3S,4R)-3-fluoro-1-methylpiperidin-4-yl]-2-(hydroxymethyl)-N-methyl-2-phenyl-2,5-dihydro-1H-pyrrole-1-carboxamide
or a pharmaceutically acceptable salt thereof.

9. The compound of claim 1 which is:

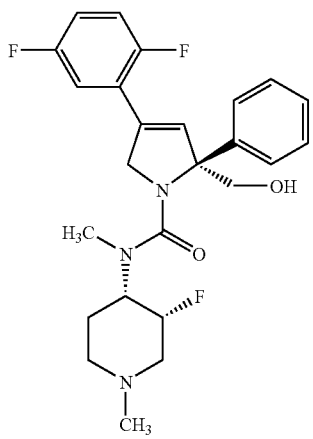

(2S)-4-(2,5-Difluorophenyl)-N-[(3R,4S)-3-fluoro-1-methylpiperidin-4-yl]-2-(hydroxymethyl)-N-methyl-2-phenyl-2,5-dihydro-1H-pyrrole-1-carboxamide
or a pharmaceutically acceptable salt thereof.

10. The compound of claim 1 which is:

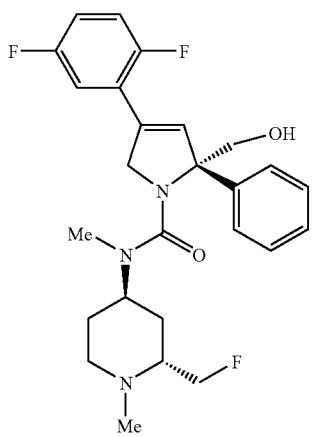

(2S)-4-(2,5-Difluorophenyl)-N-[(2R,4R)-2-(fluoromethyl)-1-methylpiperidin-4-yl]-2-(hydromethoxy)-N-methyl-2-phenyl-2,5-dihydro-1H-pyrrole-1-carboxamide
or a pharmaceutically acceptable salt thereof.

11. The compound of claim 1 which is:

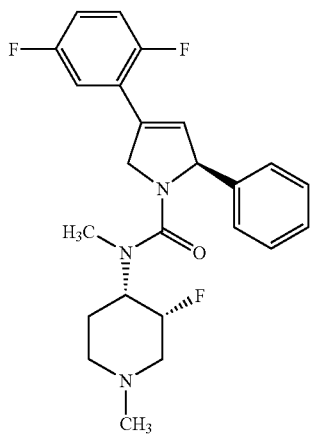

(2S)-4-(2,5-Difluorophenyl)-N-[(3R,4S)-3-fluoro-1-methylpiperidin-4-yl]-N-methyl-2-phenyl-2,5-dihydro-1H-pyrrole-1-carboxamide or a pharmaceutically acceptable salt thereof.

12. The compound selected from:

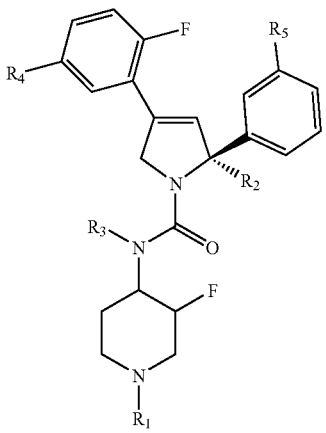

| $R_1$ | $R_2$ | $R_3$ | $R_4$ | $R_5$ |
|---|---|---|---|---|
| ∧ | $CH_2OH$ | Me | F | H |
| ∧∧ | $CH_2OH$ | Me | F | H |

-continued
| | | | | |
|---|---|---|---|---|
| 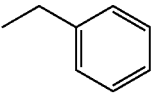 | CH₂OH | Me | F | H |
| 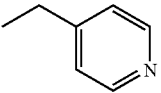 | CH₂OH | Me | F | H |
| 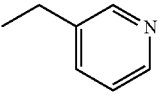 | CH₂OH | Me | F | H |
| 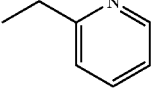 | CH₂OH | Me | F | H |
| 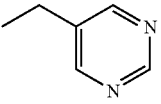 | CH₂OH | Me | F | H |
| 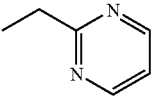 | CH₂OH | Me | F | H |
| 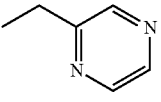 | CH₂OH | Me | F | H |
| 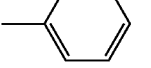 | CH₂OH | Me | F | H |
| 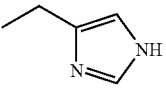 | CH₂OH | Me | F | H |
| 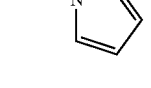 | CH₂OH | Me | F | H |
| 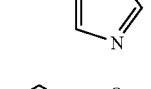 | CH₂OH | Me | F | H |
| 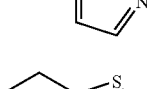 | CH₂OH | Me | F | H |
| 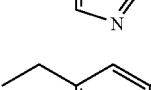 | CH₂OH | Me | F | H |
| 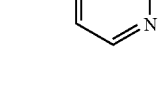 | CH₂OH | Me | F | H |

-continued
| | | | | |
|---|---|---|---|---|
| 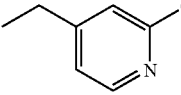 | CH$_2$OH | Me | F | H |
| 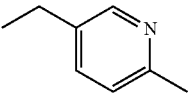 | CH$_2$OH | Me | F | H |
| 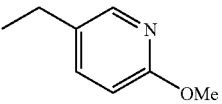 | CH$_2$OH | Me | F | H |
| Me | Me | Me | F | H |
| Me |  | Me | F | H |
| Me | 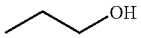 | Me | F | H |
| Me | 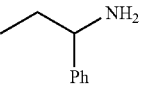 | Me | F | H |
| Me |  | Me | F | H |
| Me |  | Me | F | H |
| Me | 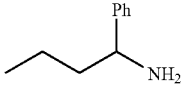 | Me | F | H |
| Me |  | Me | F | H |
| Me | 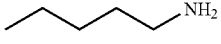 | Me | F | H |
| Me | 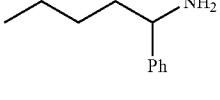 | Me | F | H |
| Me | 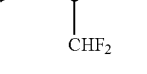 | Me | F | H |
| Me | 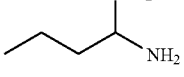 | Me | F | H |
| Me | 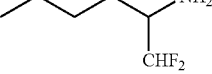 | Me | F | H |
| Me | 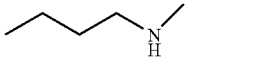 | Me | F | H |
| Me | 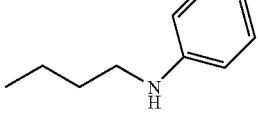 | Me | F | H |

-continued

| | | | | |
|---|---|---|---|---|
| Me | *N-butylacetamide* | Me | F | H |
| Me | *methyl butylcarbamate* | Me | F | H |
| Me | *butylurea* | Me | F | H |
| Me | *1-butylpyrrole* | Me | F | H |
| Me | *3-propyl-1H-pyrazole* | Me | F | H |
| Me | *3-propylisoxazole* | Me | F | H |
| Me | *4-propyl-1H-imidazole* | Me | F | H |
| Me | *4-propylthiazole* | Me | F | H |
| Me | CH₂OH | *propyl* | F | H |
| Me | CH₂OH | *butyl* | F | H |
| Me | CH₂OH | *isobutyl* | F | H |
| Me | CH₂OH | *cyclopropylmethyl* | F | H |
| Me | CH₂OH | *benzyl* | F | H |
| Me | CH₂OH | *phenethyl* | F | H |
| Me | CH₂OH | *cyclobutylmethyl* | F | H |
| Me | CH₂OH | *CH₂CH₂CN* | F | H |
| Me | CH₂OH | *isopentyl* | F | H |

| | | | | |
|---|---|---|---|---|
| Me | CH$_2$OH | 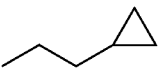 | F | H |
| Me | CH$_2$OH | Me | Cl | H |
| Me | CH$_2$OH | Me | Br | H |
| Me | CH$_2$OH | Me | CN | H |
| Me | CH$_2$OH | Me | Me | H |
| Me | CH$_2$OH | Me | CF$_3$ | H |
| Me | CH$_2$OH | Me | NO$_2$ | H |
| Me | CH$_2$OH | Me | F | OH |
| Me | CH$_2$OH | Me | F | NH$_2$ |
| Me | CH$_2$OH | Me | F | F |
| Me | CH$_2$OH | Me | F | SH |
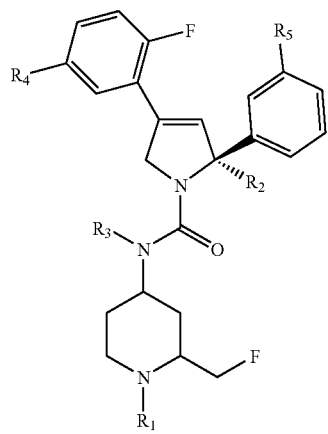
| R$_1$ | R$_2$ | R$_3$ | R$_4$ | R$_5$ |
|---|---|---|---|---|
|  | CH$_2$OH | Me | F | H |
| 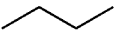 | CH$_2$OH | Me | F | H |
| 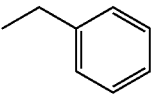 | CH$_2$OH | Me | F | H |
| 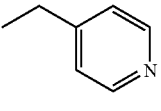 | CH$_2$OH | Me | F | H |
| 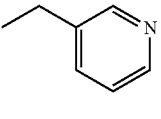 | CH$_2$OH | Me | F | H |
| 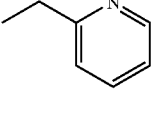 | CH$_2$OH | Me | F | H |
| 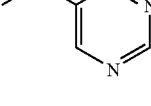 | CH$_2$OH | Me | F | H |
| 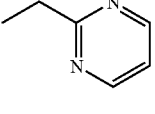 | CH$_2$OH | Me | F | H |

-continued
| | | | | |
|---|---|---|---|---|
| 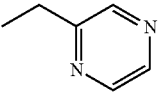 | CH₂OH | Me | F | H |
| 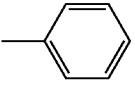 | CH₂OH | Me | F | H |
| 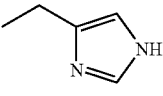 | CH₂OH | Me | F | H |
| 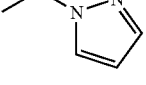 | CH₂OH | Me | F | H |
| 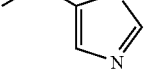 | CH₂OH | Me | F | H |
| 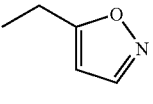 | CH₂OH | Me | F | H |
| 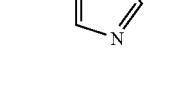 | CH₂OH | Me | F | H |
| 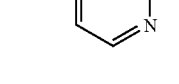 | CH₂OH | Me | F | H |
| 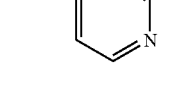 | CH₂OH | Me | F | H |
| 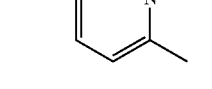 | CH₂OH | Me | F | H |
|  | CH₂OH | Me | F | H |
| Me | Me | Me | F | H |
| Me | 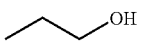 | Me | F | H |
| Me | 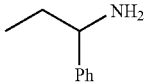 | Me | F | H |
| Me |  | Me | F | H |

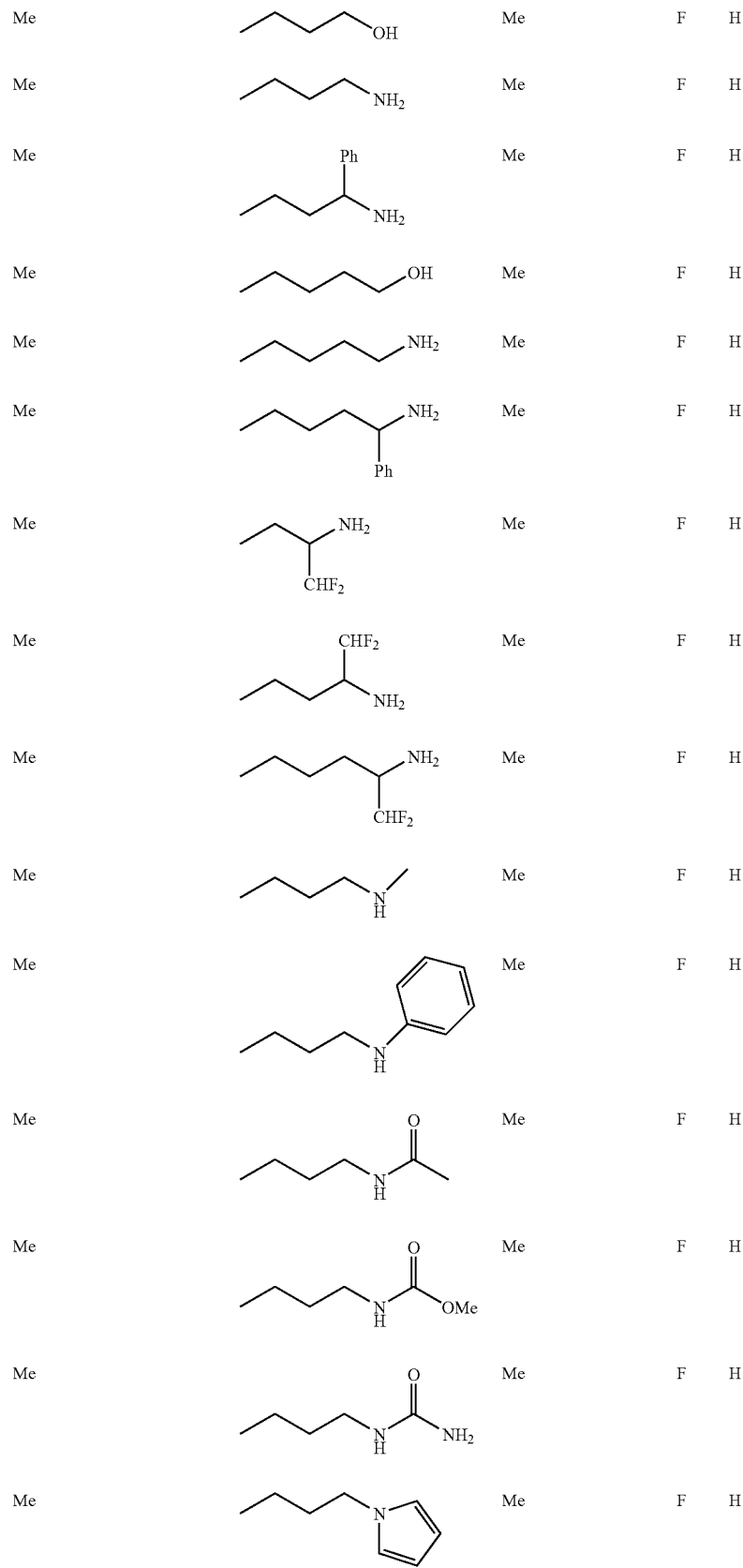

-continued

| | | | | |
|---|---|---|---|---|
| Me | (propyl-pyrazole) | Me | F | H |
| Me | (propyl-isoxazole) | Me | F | H |
| Me | (propyl-imidazole) | Me | F | H |
| Me | (propyl-thiazole) | Me | F | H |
| Me | CH$_2$OH | ethyl | F | H |
| Me | CH$_2$OH | propyl | F | H |
| Me | CH$_2$OH | isopropyl | F | H |
| Me | CH$_2$OH | cyclopropylmethyl | F | H |
| Me | CH$_2$OH | benzyl | F | H |
| Me | CH$_2$OH | phenethyl | F | H |
| Me | CH$_2$OH | cyclobutylmethyl | F | H |
| Me | CH$_2$OH | CH$_2$CH$_2$CN | F | H |
| Me | CH$_2$OH | isobutyl | F | H |
| Me | CH$_2$OH | (cyclopropyl-ethyl) | F | H |
| Me | CH$_2$OH | Me | Cl | H |
| Me | CH$_2$OH | Me | Br | H |
| Me | CH$_2$OH | Me | CN | H |
| Me | CH$_2$OH | Me | Me | H |
| Me | CH$_2$OH | Me | CF$_3$ | H |
| Me | CH$_2$OH | Me | NO$_2$ | H |
| Me | CH$_2$OH | Me | F | OH |
| Me | CH$_2$OH | Me | F | NH$_2$ |
| Me | CH$_2$OH | Me | F | F |
| Me | CH$_2$OH | Me | F | SH | or a pharmaceutically acceptable salt or stereoisomer thereof.

13. A pharmaceutical composition that is comprised of a compound in accordance with claim 1 and a pharmaceutically acceptable carrier.

14. A process for making a pharmaceutical composition which comprises combining a compound of claim 1 with a pharmaceutically acceptable carrier.

* * * * *

SEQUENCE LISTING

<160> NUMBER OF SEQ ID NOS: 2

<210> SEQ ID NO 1
<211> LENGTH: 42
<212> TYPE: DNA
<213> ORGANISM: Artificial Sequence
<220> FEATURE:
<223> OTHER INFORMATION: Completely Synthetic Nucleotide Sequence

<400> SEQUENCE: 1
gcaacgatta atatggcgtc gcagccaaat tcgtctgcga ag                42

<210> SEQ ID NO 2
<211> LENGTH: 60
<212> TYPE: DNA
<213> ORGANISM: Artificial Sequence
<220> FEATURE:
<223> OTHER INFORMATION: Completely Synthetic Nucleotide Sequence

<400> SEQUENCE: 2
gcaacgctcg agtcagtgat gatggtggtg atgctgattc acttcaggct tattcaatat    60